US008431551B2

(12) United States Patent
Duoibes et al.

(10) Patent No.: US 8,431,551 B2
(45) Date of Patent: Apr. 30, 2013

(54) NUTRITIONAL COMPOSITION MADE USING ISOLATED ORGANIC MATTER

(76) Inventors: Albert Duoibes, East Grand Rapids, MI (US); Carl Nannini, Grand Rapids, MI (US)

(*) Notice: Subject to any disclaimer, the term of this patent is extended or adjusted under 35 U.S.C. 154(b) by 206 days.

(21) Appl. No.: 12/941,844

(22) Filed: Nov. 8, 2010

(65) Prior Publication Data

US 2011/0171319 A1 Jul. 14, 2011

Related U.S. Application Data

(60) Provisional application No. 61/294,469, filed on Jan. 12, 2010.

(51) Int. Cl.
| C07H 1/06 | (2006.01) |
| C07H 1/08 | (2006.01) |
| A01N 43/04 | (2006.01) |
| A61K 31/70 | (2006.01) |

(52) U.S. Cl.
USPC ............................................ 514/62; 536/127

(58) Field of Classification Search .................. None
See application file for complete search history.

(56) References Cited

U.S. PATENT DOCUMENTS

| 4,752,579 A | 6/1988 | Arena et al. |
| 4,956,291 A | 9/1990 | Yamanobe et al. |
| 5,071,750 A | 12/1991 | Kragl et al. |
| 5,268,288 A | 12/1993 | Pharr et al. |
| 6,156,544 A | 12/2000 | Dawson et al. |
| 6,444,614 B2 | 9/2002 | Dean |
| 6,703,056 B2 | 3/2004 | Mehansho et al. |
| 6,706,295 B2 | 3/2004 | Mehansho et al. |
| 6,929,807 B1 | 8/2005 | McAnalley et al. |
| 7,109,005 B2 | 9/2006 | Eroma et al. |
| 7,132,296 B2 | 11/2006 | Ou et al. |
| 7,157,431 B2 | 1/2007 | McAnalley et al. |
| 7,196,064 B2 | 3/2007 | McAnalley et al. |
| 7,199,104 B2 | 4/2007 | McAnalley et al. |
| 7,202,220 B2 | 4/2007 | McAnalley et al. |
| 2004/0091976 A1 | 5/2004 | Deng et al. |
| 2005/0085454 A1* | 4/2005 | Ghosal .......................... 514/185 |
| 2005/0181107 A1 | 8/2005 | Naef et al. |
| 2006/0062863 A1 | 3/2006 | Ghosal |
| 2006/0246563 A1 | 11/2006 | Eroma et al. |
| 2007/0148750 A1 | 6/2007 | Hoshino et al. |
| 2008/0213425 A1 | 9/2008 | Asano et al. |
| 2009/0010904 A1 | 1/2009 | Iwai et al. |
| 2009/0123638 A1 | 5/2009 | Eyal |

OTHER PUBLICATIONS

Sobieraj, Glycemic Index, Sobieraj.com, 2000.*
Jay et al. Modern Food Microbiology, Food Science Text Series, 2005, Chapter 3, pp. 39-59.*
T. Appel et al., "Amino acids and amino sugars extracted by EUF from a sandy soil incubated with green manure, bacterial biomass or cellulose," Journal of Plant Nutrition and Soil Science, 2000, pp. 615-622, vol. 162, No. 6. Wiley-VCH Verlag GmbH & Co., Germany.
M.D. Bednarski et al., "Aldolase-Catalyzed Synthesis of Complex C8 and C9 Monosaccharides," Tetrahedron Letters, 1986, pp. 5807-5810, vol. 27, No. 48, Elsevier, England.
K. Izumori, "Izumoring: A Strategy for Bioproduction of all Hexoses," Journal of Biotechnology, 2006, pp. 717-722, vol. 124, No. 4, Elsevier Science Publishers, Netherlands.
D. Solomon et al., "Soil Organic Matter Composition in the Subhumid Ethiopian Highlands as Influenced by Deforestation and Agricultural Management," Soil Science Society of America Journal, 2002, pp. 68-82, vol. 66, The Soil Science Society of America, U.S.
T. Miano, "Fractionation of Water-Soluble Sugars in Two Humus Profiles by Thin-Layer Chromatography," Zeitschrift fur Pflanzenernahrung und Bodenkunde, 2007, English Abstract Only, vol. 153, No. 4, WILEY-VCH Verlag GmbH & Co. Germany.
AOAC Official Method 990.12, "Aerobic Plate Count in Foods" in AOAC Official Methods of Analysis (2005), AOAC International, Gaithersburg, MD.
AOAC Official Method 991.14, "Coliform and *Escherichia coli* Counts in Foods" in AOAC Official Methods of Analysis (2005), Chapter 17, p. 32, AOAC International, Gaithersburg, MD.
V. Tournas, et al., "Yeasts, Molds and Mycotoxins" in Bacteriological Analytical Manual, 8th Edition, Revision A (2001), Chapter 18, Food and Drug Administration, Center for Food Safety and Applied Nutrition, College Park, MD.
C.A. Browne, "Galactomannan" in a Handbook of Sugar Analysis, 2nd Edition, p. 600, John Wiley & Sons, New York, 1912.
3M Petrifilm TM Aerobic Count Plate Interpretation Guide, 2005, 3M Microbiology Products, St. Paul, MN.
3M Petrifilm TM Coliform Count Plate Interpretation Guide, 1999, 3M Microbiology Products, St. Paul, MN.
3M Petrifilm TM Yeast and Mold Count Plate Interpretation Guide, 2004, 3M Microbiology Products, St. Paul, MN.
3M Petrifilm TM Plates & Plate Reader Brochure, 2008, 3M Microbiology Products, St. Paul, MN.
AOAC Official Method 997.02, "Yeast and Mold Counts in Foods" in AOAC Official Methods of Analysis (2005), Chapter 17.2.09, AOAC International, Gaithersburg, MD.

* cited by examiner

*Primary Examiner* — Layla Bland
(74) *Attorney, Agent, or Firm* — Amin Talati, LLC; Janine A. Moderson; George M. Carrera, Jr.

(57) ABSTRACT

Nutritional compositions, formulations, and intermediates are provided which may be utilized to formulate various sweeteners and other products. The formulations described herein are made from constituents found in soils or fossilized soils.

31 Claims, 6 Drawing Sheets

NUTRITIONAL COMPOSITION MADE USING ISOLATED ORGANIC MATTER

This application claims the benefit of earlier filed U.S. patent application Ser. No. 61/294,469 filed on Jan. 12, 2010.

FIELD

In connection with the embodiments of the presently claimed invention, selected compositional embodiments, formulational embodiments, intermediates, and/or products thereof may contain organic matter. The organic matter may be derived from certain soils rich in plant material and/or plant derived materials. These materials may include plant breakdown products and/or plant breakdown byproducts.

Other selected compositional embodiments, formulational embodiments, and/or intermediates thereof may contain organic matter derived from fossilized soil (FS) rich in plant material and/or plant derived materials. The fossilized soil (FS) may contain one or more of fossilized soil constituents (FS-CNs) and non-fossilized soil constituents (N-FS-CNs), or combinations thereof.

Some of the (FS-CNs) may be plant materials, plant derived materials or combinations thereof. Likewise, some of the (N-FS-CNs) may be from plant materials, plant derived materials, or combinations thereof. Other (FS-CNs) may be from non-plant materials and/or from non-plant derived materials. Selected compositional embodiments, formulational embodiments, intermediates, and/or products thereof may include N-acetylglucosamine (NAG), which has the structure of Formula 1 recited below:

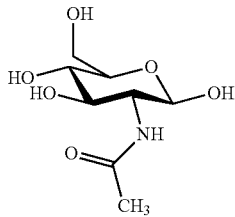

(Formula 1)

Fossilized soils (FS) may provide certain benefits. The fossilization itself may have preserved some of the FS-CNs' desirable properties of certain plant materials, plant derived materials and/or materials not from plants. Various compositions, formulations, intermediates, and products containing (FS-CNs) and/or the (N-FS-CNs) may be useful for their desirable properties. Some of the desirable properties may be attributable to the FS-CNs. The (FS-CNs) and (N-FS-CNs) may include, one or more of certain monosaccharides (MS), certain amino acids (AA), certain elements and minerals (MINS), certain antioxidants (AO), certain oligosaccharides (OS), and/or certain acids (e.g., fulvic acid (FA), humic acid (HA) and/or humifulvic acid (HFA)) in a number of possible combinations and/or permutations, as described herein.

Illustrative embodiments of the claimed invention may include formulations of one or more of foods, sweeteners, sugar substitutes, vitamin supplements, nutritional supplements (e.g., fossilized nutrition (FN)), dietary supplements, medicaments, homeopathic formulations, cosmetics, and/or one or more additives or constituents thereof, respectively.

Certain compositional embodiments, formulational embodiments, intermediates, and/or products thereof (in whole or in part) may be constituents of one or more of: selected foods, sweeteners, sugar substitutes, taste modifiers, vitamin supplements, nutritional supplements, dietary supplements, medicaments, homeopathic formulations, cosmetics, other formulations, other products described herein, and/or combinations thereof, respectively.

One or more of the herein described compositional embodiments, formulational embodiments, and/or other products may be or may contain one or more of Formulation I and Formulation II in varying amounts as preferred. The Formulation I and/or Formulation II may be used in varying amounts as taste modifiers, taste enhancers, and/or sweeteners. Formulation I and/or Formulation II could be used in coffee, tea, other beverage, food, etc. to modify, enhance and/or sweeten the relevant coffee, tea, beverage or other product. Though typically used separately, Formulation I and/or Formulation II could be used in some combination(s) as desired to obtain a specific taste or sweetness profile or to enhance the same.

Other embodiments may include one or more compositional intermediates (e.g., fossilized nutrition (FN) with or without iron (Fe)). If the iron (Fe) present in (FN) is removed to a suitable level, the (FN) may be converted to its (Fe)-less form denoted herein as "fossilized nutrition clear" (designated as either (FNC) or (Fe-less FNC)). Thus, when the iron is removed from the (FN), it is converted to (FNC). The (FNC) may be used as an intermediate for the production of various sweeteners such as Formulation II. Likewise, the (FN) together with its iron (Fe) may be used for the production of sweeteners such as Formulation I, or the (FN) may be used for the production of one or more of the formulations and products such as selected foods, selected sweeteners, selected sugar substitutes, selected taste modifiers, selected nutritional supplements, selected dietary supplements, and/or any of the formulations or compositional embodiments described herein unless expressly indicated otherwise.

Particular compositional or formulational embodiments useful in connection with the claimed invention may include N-acetylglucosamine (NAG), which has the structure of Formula 1 recited above.

Selected intermediates may be useful for the production of any of the herein-described compositional embodiments, formulational embodiments, and/or other intermediates thereof. Some intermediates may be optional or preferred intermediates for use in connection with the claimed invention. Some of the intermediates may be suitable for the production of selected sweeteners, taste modifiers, sugar substitutes, nutritional supplements, dietary supplements, cosmetics, other compositions, other formulations, and/or other products described herein.

Pursuant to one or more process embodiments, one or more of the foregoing compositional embodiments, formulations and/or intermediates may be cost-effectively and/or efficiently made by the inclusion (or addition) of certain organic matter derived from selected soils and/or with other non-soil derived ingredients in various combinations as needed, desired, or described herein. One permutation may be devoid of non-soil derived ingredients or constituents. Another permutation may include non-soil derived ingredients or constituent(s).

In connection with various embodiments, certain organic matter may be obtained from the soils described herein. The organic matter obtained from these soils may be used "as is" or may be converted into other forms suitable for use in connection with embodiments of the claimed invention. Such organic matter may itself have been derived from plant materials found in certain soils such as in fossilized soils (FSs') noted herein. Selected organic matter may be utilized in connection with one or more of the aforementioned formulations, compositional embodiments and/or intermediates, as described herein.

Obtaining the organic matter from certain selected soils (e.g., FN) may require the process steps described herein. The selected soils may be rich in plant matter, plant breakdown products and/or plant breakdown byproducts. The organic matter may be removed from the selected soil and may be accomplished by various separation techniques including extraction. Removing selected organic matter from selected soils may be accomplished using certain extraction procedures together with commensurate equipment, techniques and solvents, as needed. The separation of selected organic matter may be conducted according to the details described herein. Suitable materials and methods for removing sought organic matter from selected soils (or selected FSs) may involve extraction with particular solvents as described herein. After removing the organic matter from the selected soil, the separated organic material can be further used, treated, added, supplemented, and/or converted to formulate one or more of the compositional embodiments, formulational embodiments and/or intermediates as described herein.

In view of considerations regarding safety due to the fact that "soil" naturally contains microflora and microfauna together with other microbes which may, if left untreated, be unsafe, it is prudent to treat "soils" or products, or intermediates derived from them to render them safe. Accordingly, proper implementation of testing protocols and procedures to adequately treat and test the "soil" samples and "soil derived products" described herein should be addressed. By doing so, undesirable and potentially dangerous health consequences can be avoided. Additionally, the compositions, formulations, intermediates, and/or products described herein can be ensured to be safe for use in humans and/or animals (e.g., cat, dog, other household pet or animal, etc.). As such, any concern as to health hazards upon ingestion, handling and/or topical application can be appropriately addressed and removed. Thus, to ensure the safety of the relevant compositional embodiments (also denoted as "composition(s)" or "compositions" within this application), formulational embodiments (also denoted as "formulation(s)" or "formulations" within this application), intermediate embodiments (also denoted as "intermediate(s)" or "intermediates" within this application), and/or "products" as described herein, may require sufficient sterilization may be required, together with sufficient testing to ensure safety for use in humans and/or animals.

Thus, the use of aseptic technique, proper equipment and procedures, and sufficient training of personnel, in connection with embodiments of the claimed invention may be essential if the contemplated embodiment would otherwise represent a health hazard. In some instances, the sterilization should be such that it ensures safety, while using appropriate sterile packaging without defeating the desirable use of the composition, formulation, intermediate, product and/or processing involved. Some techniques may require sterilization via passing through a 0.22 micron filter to remove microbial and other health contaminants such as viruses and/or bacteria. Additionally, aseptic technique and processing should be used and applied by a qualified technician to maintain safety. If, for example, a particular contaminant were detected, then that contaminant would need to be removed or its associated hazard would need to be properly, safely and adequately nullified.

Accordingly, proper aseptic procedures, quality control measures and safety checks may need to be updated, implemented and followed by qualified personnel, as needed to ensure the requisite safety. To do so, one could hire outside experts to assist in implementing and complying with necessary safety and quality measures, or one could set up the same in-house. Also, appropriate equipment, packaging, execution, manufacturing considerations, manufacturing processes, design, and/or other relevant considerations may be needed.

With respect to safety and quality control testing, samples will need to be prepared and tested to confirm safety as applicable to "soil" derived materials, FN—CNs, N—FN—CNs, FS, etc. used with equipment coming in contact with the compositions, formulations, intermediates and/or products described herein. Considerations regarding handling, processing, or adding plant materials, plant derived materials, organic or non-organic matter, etc. derived from the "soils" noted herein may require following certain safety testing as needed (e.g., procedures relating to preparation of test samples, testing equipment and reagents, aseptic technique, testing protocols, testing standards, testing measurements, record keeping of lot numbers, etc.) to ensure that safe product(s) are provided.

An example of a product suitable for use in connection with the claimed invention, or embodiments thereof, may be a composition denoted herein as "sterile fossilized soil organic matter" (SFSOM), optionally containing one or more of certain monosaccharides (MS), certain amino acids (AA), certain elements and minerals (MINs), certain oligosaccharides (OS), certain antioxidants (AO), and certain acids (e.g., fulvic acid (FA), humic acid (HA) and/or humifulvic acid (HFA), together with certain additional ingredient(s) (as described herein) in a number of possible combinations and/or permutations thereof (as described herein).

Additional ingredients may include, but are not limited to, sucrose, a source of glucose/fructose, raw arabica from the coffee plant *Coffea arabica* L. (optionally or preferably providing a significant quantity of glucose and xylose), a source of glucose/xylose, fibersol, mangosteen, acai berry, and other beneficial carbohydrates or other nutrients of interest, optionally combined at various process stages including, but not limited to, before formation of the fossilized nutrition (FN), after formation of the fossilized nutrition (FN), and during or after crystallization of certain formulations (e.g., Formulation II).

One embodiment of the presently claimed invention is a composition comprising sterile fossilized soil organic matter (SFSOM). Another embodiment of the presently claimed invention provides a method for preparing sterile fossilized soil organic matter (SFSOM) by a reaction between the (SFSOM) and a disaccharide.

In order to prepare sterile fossilized soil organic matter (SFSOM) compositional embodiments, formulational embodiments, and/or intermediates, a preferred source of monosaccharides (MS) and other desirable constituents may be used as described herein.

BACKGROUND

A variety of multi-monosaccharides such as glycoproteins, glycolipids, glycosaminoglycans, and polysaccharides are composed of varying amounts of different monosaccharide units chemically linked together as constituent building blocks. The knowledge of their composition (e.g., the identity of the constituent monosaccharide building blocks coupled with their frequency of occurrence) appeared to provide a roadmap to break the chemical links between the constituent monosaccharide units to harvest them—hopefully in yields near the frequency of their occurrence. By using such a "Decoupling Approach," one might recover sought after monosaccharides in sufficient yields at a low cost, and at high production throughput levels with less complexity, for various uses.

Monosaccharides are carbohydrates that cannot by hydrolyzed into simpler carbohydrates. Of all the monosaccharides, glucose is the most important due to its use as the major metabolic fuel of mammals and as an energy source for plants. There are also eight commonly recognized essential monosaccharides: mannose, xylose, galactose, fucose, arabinose, N-acetylneuraminic acid, N-acetylgalactosamine, and N-acetylglucosamine. Of these monosaccharides, only glucose and galactose are found in a typical diet.

Because of the importance of saccharides in biological systems, methods for the synthesis of monosaccharides are of considerable utility. Monosaccharide units are essential for practical synthesis of all glycoproteins, glycolipids, glycosaminoglycans, and polysaccharides. However, monosaccharide synthesis is typically performed using classical organic synthesis methodologies, many of which are labor intensive and require multiple steps, or via enzymatic breakdown of polysaccharides.

N-acetylglucosamine is a valuable pharmacological agent in the treatment of a wide variety of ailments. N-acetylglucosamine does not have any established negative side effects. Since N-acetylglucosamine is a valuable and important component of protein synthesis in the animal body, it has a positive effect on tissue regeneration. N-acetylglucosamine also has therapeutic potential in the prevention and/or treatment of a wide variety of diseases such as gastritis, food allergies, inflammatory bowel disease (IBD), diverticulitis, acute and chronic forms of rheumatoid arthritis and osteoarthritis, as well as the pathological conditions arising from metabolic disorders of the osteoarticular tissues.

N-acetylglucosamine is not widely available in the marketplace. It is currently produced by the acetylation of glucosamine using an organic acetylating reagent such as acetic anhydride, an expensive and difficult step. These processes suffer from poor product yields (in the range of 50% conversion of substrate to glucosamine). Another currently available process to synthesize N-acetylglucosamine includes fermentation and isolation from several products.

Decoupling Approach as Hypothetical

Though the past tense is used herein, it is to be understood that the "Decoupling Approach" described herein is a hypothetical depiction provided to illustrate and analyze certain difficulties and problems that may be encountered with such approach. Having provided such qualification, it is to be understood that this illustration recites hypothetical multi-monosaccharide compounds with hypothetical monosaccharide labels in varying hypothetical amounts of the same, as set forth in connection with hypothetical recovery values presented together with a generic decoupling procedure to provide a better understanding of certain problems and difficulties that may be encountered with such approach.

Additionally, the qualifier "Without being bound by theory" is applicable to statements in this application where there is any particular causal link discussed or put forth as to cause and effect, as to cause and result, or as to any theory of causation or theory of operation described or addressed herein in any fashion. Such qualifier is made as to each such statement, whether made expressly or by implication in view of this paragraph and its applicability to this entire application, wherever appropriate.

Having made the foregoing qualifications, it was expected that when the strategy of decoupling constituent monosaccharide units by breaking the chemical links between them would be tried, certain sought monosaccharides (and sought monosaccharide combinations) in desired yields could be successfully acquired at low cost, and at high production throughput levels with low complexity. Unfortunately, such expectations remained unfulfilled for quite some time as these types of problems are further described below. Without being bound by theory, it is believed that the sought constituent monosaccharides (and sought monosaccharide combinations) may not have been recovered in the expected yields, in part, because during the decoupling process, the original constituent monosaccharide chemical structures were not sufficiently conserved/preserved.

Without being bound by theory, it is believed that the sought monosaccharides (and sought combinations thereof) were not acquired as expected or desired because some monosaccharides (and monosaccharide combinations) were converted into unwanted compounds or into other unwanted monosaccharides so that the sought-after monosaccharides in the desired yields could not be easily recovered. Accordingly, this approach was deemed too cumbersome to execute due to such problems and difficulties.

Further, small scale bench processing is typically deemed too inefficient when scaled up to satisfy high throughput levels at a low cost with less complexity.

Illustration of Decoupling Approach With More Specific Hypothetical Labels and Values Consider, for example, a particular multi-monosaccharide (←continued—A-B-C-D—continued→) containing monosaccharides hypothetically labeled as A, B, C and D to convey that they are not identical monosaccharides. Accordingly, it is to be understood that the monosaccharides so labeled with different letters are monosaccharides of different chemical structures represented by the notation: $A \neq B \neq C \neq D$. With that understanding, now consider that a generic procedure is implemented to decouple and to recover the constituent monosaccharides A, B, C, and D originally present in the multi-monosaccharide of the structure (←continued—A-B-C-D—continued→). The plan is to recover the original amounts of A, B, C, and D present in the starting multi-monosaccharide structure (←continued—A-B-C-D—continued→) using the decoupling procedure implemented, as to each of A, B, C, and D originally present.

In this context, consider a breakdown hydrolysis process to decouple the links between A, B, C, and/or D while preserving or substantially preserving the original (or nearly original) content levels of A, B, C, and D originally present in (←continued—A-B-C-D—continued→) at post breakdown and subsequent recovery of the constituent A, B, C, and D monosaccharide units.

Now further consider that the monosaccharide B is of particular interest because hypothetically it is considered difficult to obtain in desired sufficient yields, at low cost, at high throughput production levels and with low complexity, etc.

In such hypothetical illustration herein below, consider the aforementioned multi-monosaccharide compound (←continued—A-B-C-D—continued→) originally containing:

20% monosaccharide units A;
40% monosaccharide units B;
20% monosaccharide units C; and
20% monosaccharide units D.
(TOTAL=100% before attempted breakdown of constituent monosaccharides.).

However, pursuant to this hypothetical, after being subjected to decoupling and upon breakdown, the yields of the constituent monosaccharides (A, B, C and D) originally present in (←continued—A-B-C-D—continued→) were quite disappointing with respect to recovery of monosaccharide B of interest:

40% monosaccharide units A;
0% monosaccharide B;
49% monosaccharide units C; and
11% monosaccharide units D.
(TOTAL=100% after breakdown of recovered monosaccharides.).

In effect, during the above-noted decoupling and implemented breakdown seeking constituent monosaccharides, none of monosaccharide B was recovered. In other words, even though the relative percent values—before breakdown (40% B)—and—recovery after breakdown (0% B)—are hypothetical values, one would be quite surprised were the hypothetical presented herein a true enough qualitative reflection of reality where the breakdown process were to yield no B when starting out with 40% B. While it could be that much of the monosaccharide B simply could not be recovered, it is quite possible that monosaccharide B was converted into another monosaccharide or into some other undesirable or undetectable chemical entity.

The problem being, of course, that no B was recovered from an original content starting out at 40% B. In this hypothetically illustrative situation where the breakdown process yielded no monosaccharide B from a multi-monosaccharide compound originally containing 40% monosaccharide B (and hypothetically consider such result were qualitatively applicable to one or more of each sought monosaccharide that is difficult to obtain at low cost, and at high throughput levels with low complexity), the difficulty encountered with this "Decoupling Approach" to recover monosaccharide B of particular interest is readily apparent. Now, noting that the foregoing may not apply exactly to every situation, it still would apply to those instances where these types of difficulties have not been resolved to satisfy the need to obtain a hard-to-obtain monosaccharide (or hard to obtain at a reasonable price and at high throughput levels). The same may apply to a combination of hard to obtain monosaccharides as well.

Alternate Synthesis Approach with Hypothetical Labels

In view of resolving the difficulties noted one might alternatively attempt to synthesize the desired monosaccharide B in sufficient yield by relying on a classical organic synthetic route for each difficult-to-obtain monosaccharide represented by the generic label B. In that context, one could attempt to synthesize the monosaccharide B of interest in sufficient yield. However, such classical synthetic organic methods for making the monosaccharide B of interest (with sufficient yield) can often be likewise difficult to accomplish—depending on the particular relevant structure involved.

When taking the structure of interest into consideration, one not only has to consider chemical identity but may also have to take into account (1) various polymorphic forms (if any), (2) varying reactivities (if any), (3) varying solubilities (if any), (4) varying difficulties of each variant form, (5) varying stabilities, and (6) potentially other known but unpredictable variations, (7) inconsistent reactivities, etc. and (8) any unknown variables that may be found only after failed attempts to synthesize a monosaccharide B of particular interest, and so on. Each of the foregoing factors (1)-(8) emphasize the complexity involved with such a classical synthetic approach given that one may need to synthesize compounds hard-to-synthesize from "scratch".

And, the solution to the problem of synthesizing the particularly difficult-to-make monosaccharide may be so difficult to solve that the solution is not even remotely within reach. In such case, a particular compound may be very expensive or nearly impossible to obtain in quantities sought at low cost, etc.

Such levels of uncertainty increase the complexity of this hypothetical classical synthetic approach. In fact, in every (or nearly every) instance where a reliable and reproducible synthetic route is unknown, the complexity escalates in part due to the uncertainty of meeting a high throughput level if needed (say, for example, immediately in response to some emergency), irrespective of cost and complexity. To appreciate the difficulties, one has to simply multiply the number of such potentially problematic considerations (i.e., see (1)-(8) listed two paragraphs above or more as some may yet remain to be identified) by the number of monosaccharides being sought. By doing so, the magnitude of the complexity skyrockets to the point of foregoing this alternate approach as well.

But, even if a classical synthetic organic method for the synthesis of monosaccharide B of interest were known, the cost, yield, efficiency, time, and the like may still not be sufficiently favorable to make the desired monosaccharide B of interest at sufficiently low cost, in desirable yield and with the level of efficiency necessary to meet high throughput levels, especially if an order were placed with little notice. Other considerations as to purity, separation, isolation, and/or recovery may still need to be solved, if such exist. Thus, such methods may still suffer from a variety of disadvantages, difficulties and/or problems, including: unsuitable and/or undesirable time requirements, cost and/or resource intensive procedures, coupled with insufficient yields, and/or too much complexity, and too high throughput demands that could not be readily or otherwise met.

Also, the above-noted problems that may be encountered with respect to monosaccharide B of interest can be analogized to a variety of monosaccharide(s) that are difficult-to-synthesize or recover by a decoupling process in adequate yield at low cost. Thus, it may be necessary to find another way to overcome the problems encountered with respect to the formation of the hard-to-make or hard-to-obtain monosaccharide B of interest in sufficient yield as sought, preferably in a cost effective and time efficient manner.

In view of the above, another approach may be better suited to overcome one or more of the foregoing difficulties. Thus there is a need for a yield efficient and cost efficient monosaccharide production system to prepare compositions including nutritional compositions having at least one saccharide and other beneficial nutritional components derived from cheap and readily obtainable starting materials. To that end, the present inventors approached the problem(s) from a quite different view in order to prepare nutritional compositions comprising one or more saccharides.

SUMMARY

The following description relates to one or more illustrative embodiments of the compositions, formulations, intermediates and/or processes associated with any permutations described anywhere herein. In that regard, each expressly contemplated permutation of such compositions, formulations, intermediates, products, and processes is disclosed. In such context, each permutation of TABLES 1, 1a, 2, 3, 3a, 4, 5, 6, 7, 8, 9, and 10 is fully disclosed and described herein by operation of this paragraph, language noted elsewhere in this application, and taken in conjunction with TABLES 1, 1a, 2, 3, 3a, 4, 5, 6, 7, 8, 9, and 10 unless expressly stated otherwise. Thus, each such permutation of each of the foregoing TABLES can be combined with the sterile fossilized soil organic material (SFSOM) including the N-acetylglucosamine (NAG) of Formula 1:

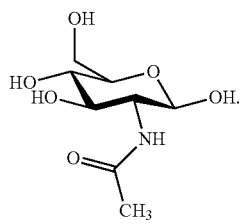

(Formula 1)

One or more embodiments of the presently claimed invention is/are directed to the sterile fossilized soil organic material (SFSOM) including the N-acetylglucosamine (NAG) of Formula 1.

According to an embodiment, the above-noted (SFSOM) is provided in sufficiently sterile form so as to be suitable for safe human ingestion, handling and/or safe topical application on a human. Pursuant to another embodiment, the (SFSOM) is safe for human ingestion as a food, a sugar substitute, a sweetener, a taste modifier, a nutritional supplement, a vitamin supplement, a medicament and/or as an additive thereof, respectively. See further description herein. The same may be applied to animals including, but not limited to, household pets.

In another embodiment, a composition or formulation of the (SFSOM) is provided in sufficiently sterile form suitable for topical application in a dermatological preparation, a skin treatment, a cosmetic formulation, and/or as an additive thereof. The same may be applied to animals including, but not limited to, household pets.

Pursuant to yet another embodiment, the (SFSOM) is provided in a sufficiently sterile form suitable for human ingestion or topical application on a human, as described herein, in addition to having satisfied a first sterile profile (Petrifilm™ Aerobic Plate Count of <100 counts/gm (SFSOM)), a second sterile profile (Petrifilm™ Coliform Plate Count of <100 counts/gm (SFSOM)), a third sterile profile (FDA-BAM 7$^{th}$ Edition) with respect to yeast colonies (<10 counts/gm (SFSOM), and/or a fourth sterile profile (FDA-BAM 7$^{th}$ Edition) with respect to mold colonies (<10 counts/gm (SFSOM). It appears that 3M Corporation's Petrifilm™ Plates already impregnated with necessary growth media and possibly stain are already pre-made by 3M for use in accordance with AOAC's protocol set forth herein. The same sterility may or may not be applied to animals including, but not limited to, household pets depending on the specific circumstances. Sterility levels are expressed in microbiological terms as "colony forming units/g–sample" (cfu/g).

According to a further embodiment, the herein-noted (SFSOM) composition(s) may also contain one or more of N-acetylneuraminic acid, N-acetylgalactosamine, glucose, fucose, galactose, arabinose, xylose, mannose and/or any combinations thereof as may be described herein. Pursuant to another embodiment, the herein-described (SFSOM) composition(s) (i.e., note that "herein-described" or "described herein" means anywhere in this application unless expressly indicated otherwise) may include one or more of N-acetylneuraminic acid, N-acetylgalactosamine, glucose, fucose, galactose, arabinose, xylose, and mannose together with other constituent(s) as further noted herein where the amount of each of the foregoing monosaccharides is provided in a range (a) from about 9 ppm to about 38,240 ppm, (b) from about 9 ppm to 38,240 ppm, and (c) from 9 ppm to 38,240 ppm for each of and/or for one or more of N-acetylneuraminic acid, N-acetylgalactosamine, glucose, fucose, galactose, arabinose, xylose, and/or mannose, respectively. In accordance with further embodiment(s), the total of one or more of N-acetylneuraminic acid, N-acetylgalactosamine, glucose, fucose, galactose, arabinose, xylose, and mannose that may be present as an aggregate of up to two monosaccharides may total (d) up to about 71,200 ppm or (e) up to 71,200 ppm.

Additional embodiments may include the herein-noted (SFSOM) compositions (noted anywhere in this application) together with one or more amino acids (AA). The amino acids (AA) that may be present according to one or more embodiments may be chosen according to each of the possible permutations and combinations recited in agreement with TABLE 1, TABLE 1a, TABLE 2, TABLE 3, TABLE 3a, TABLE 4, TABLE 8 and TABLE 10, respectively. Pursuant to other embodiment(s), the herein-noted (SFSOM) composition(s) may include various elements and/or minerals noted in accordance with each possible permutation or combination noted in TABLE 4, TABLE 5, TABLE 6 and TABLE 7.

Pursuant to further embodiments, the herein-noted (SFSOM) may include one or more of the following: N-acetylneuraminic acid (NANA), N-acetylgalactosamine (NAGA), glucose (GLUC), fucose (FUC), galactose (GALC), arabinose (ARAB), xylose (XYL) and mannose (MANN) together with amino acid(s) (AA), antioxidant(s) (AO), mineral(s) (MIN), monosaccharide(s) (MS), oligosaccharide(s) (OS), humic acid (HA), fulvic acid (FA), and/or humifulvic acid (HFA) and any combinations or sub-combinations thereof.

According to another embodiment, the herein-noted (SFSOM) may have a pH from about 1 to about 4, from about 1 to 4, from 1 to 4, from about 2.3 to about 2.4, from 2.3 to about 2.4, from 2.3 to 2.4, from about 1.7 to about 2.9, from 1.7 to 2.9, or any ranges therebetween, respectively. See other ranges of pH noted herein, with respect to one or more selected embodiments of (SFSOM).

Further embodiments of the herein-noted (SFSOM) composition(s) may further include one or more of humic acid (HA), fulvic acid (FA), humifulvic acid (HFA), and/or any combinations thereof. See other permutations disclosed herein. For example, consider (SFSOM) together with (NAG) and one or more of (HA), (FA), and (HFA) with the other constituents—the herein noted monosaccharides (MS), amino acids (AA) the elements and minerals (MINs).

With respect to a process for forming embodiment(s) of (SFSOM), pursuant to yet another embodiment of the presently claimed invention, organic matter (OM) may be separated from fossilized soil (FS) by extraction with an aqueous solvent to form a liquid extract that may optimally and independently contain one or more monosaccharides (MS), amino acids (AA), antioxidants (AO), oligosaccharides (OS), elements and minerals (MINS), and/or acids ((HA), (FA), and/or (HFA)) and any combinations or sub-combinations thereof as further described herein. For example, each permutation of TABLES 1, 1a 2, 3, 3a, 4, 5, 6, 7, 8, 9 and 10, respectively, containing (SFSOM) composition(s) with NAG, when presented collectively, describe a large set of possible permutations, each of which is within the express description of this application. Any one of the possible permutations as disclosed herein may be a compositional embodiment, a formulational embodiment or an intermediate suitable for use with or under an embodiment of the presently claimed invention. Likewise, any one of the possible permutations as disclosed herein may be a composition, a formulation, an intermediate and/or a product suitable for use with or under an embodiment of the presently claimed invention.

According to another embodiment, the liquid extract obtained via extraction of the (FS) may be sterilized to satisfy the aforementioned first sterile profile, the second sterile profile, the third sterile profile, and/or the fourth sterile profile, and any combination thereof.

Pursuant to another embodiment, a soluble phosphate (e.g., potassium phosphate monobasic (PPM), etc.) may be added to the sterilized liquid extract (SLE) having the first, second, third, and/or fourth sterile profile, and optionally separating a precipitate from the so treated sterilized liquid extract (SLE), leaving behind a substantially clear sterilized liquid extract ("Fossilized Nutrition Clear" or "Clear Fossilized Nutrition") essentially free of dissolved iron (Fe) therein (designated as (Fe)-less-FNC) or (FNC)). According to another embodiment, a disaccharide (e.g., sucrose) may be added to the sterilized liquid extract essentially free of dissolved iron ((Fe)-less-FNC) to yield a disaccharide solution (DSS). The disaccharide may be sucrose (or a source of fructose and glucose) which may optionally be provided in a 50:50 (w/w) ratio of fructose to glucose.

Pursuant to another embodiment, a source of xylose and/or glucose may be mixed or added into the disaccharide solution (DSS) with optional mixing of the resultant solution until the color of the disaccharide solution (DSS) turns green or is green in color. The mixing may be optional but it may be preferred to improve efficiency. A further embodiment includes one where the xylose plus glucose are added as part of raw arabica obtained from the coffee plant *Coffea Arabica* L.

According to further embodiment(s), the so formed green solution may be dried leaving behind a green precipitate including one or more of minerals, monosaccharides, oligosaccharides, amino acids, antioxidants, HA, FA, and/or HFA, and any combinations or sub-combinations thereof pursuant to each of the various permutations described herein including each of TABLES 1, 1a, 2, 3, 3a, 4, 5, 6, 7, 8, 9, and 10, respectively.

BRIEF DESCRIPTION OF THE DRAWINGS

One or more aspects and/or advantages of the claimed invention may become apparent and more readily appreciated from the following description of one or more embodiments, when taken in conjunction with the accompanying drawings of which:

DETAILED DESCRIPTION OF EMBODIMENT(S)

Figure 1:
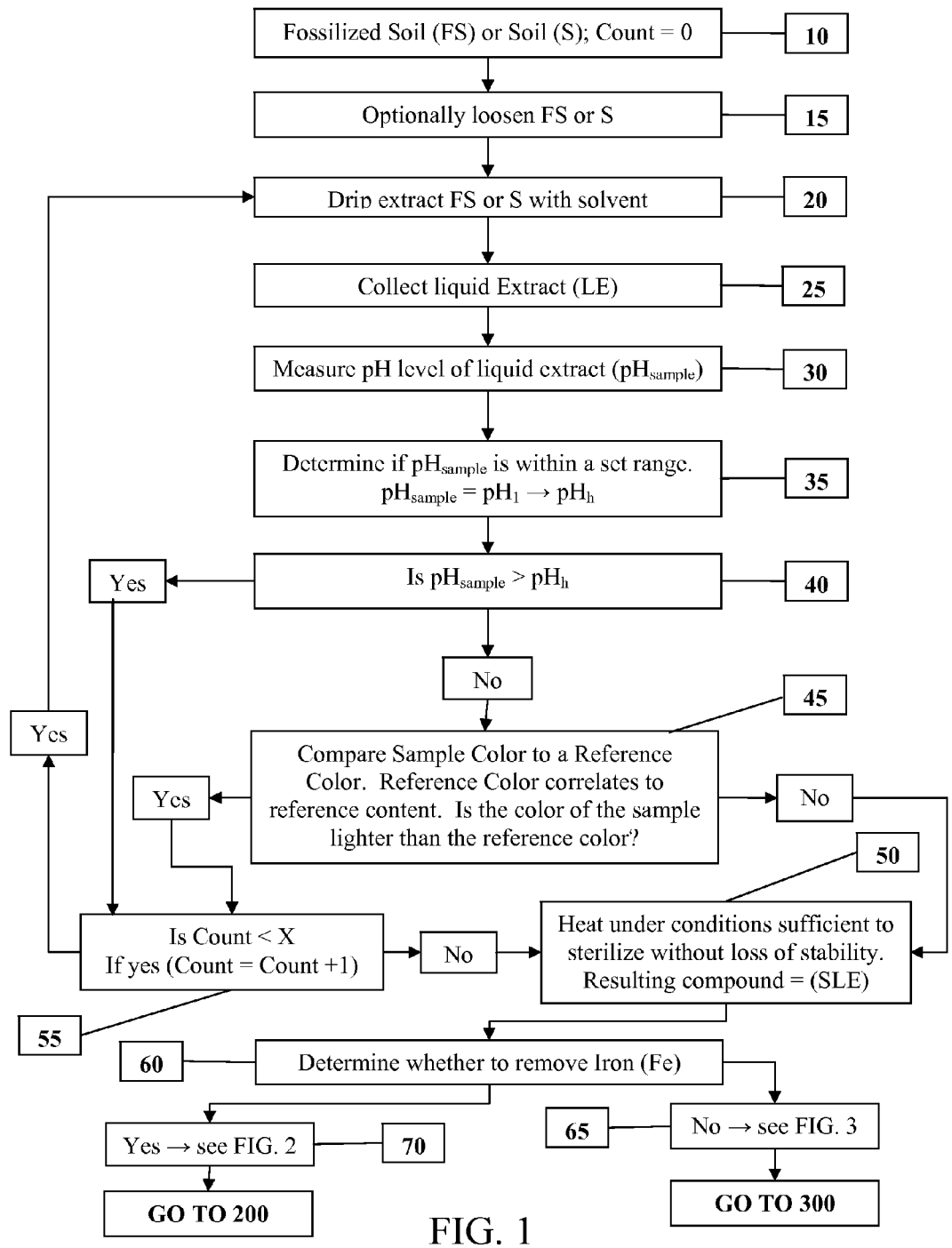
FIG. 1 provides a flowchart of one embodiment of a process suitable for use in connection with the presently claimed invention.

As used herein, "amino acid" or "(AA)" is a term used in its broadest sense and may refer to an amino acid in its many different chemical forms including a single administration amino acid, its physiologically active salts or esters, its combinations with its various salts, its tautomeric, polymeric and/or isomeric forms, its analog forms, its derivative forms, and/or its decarboxylation products, if so noted expressly or so noted expressly later in time with support to do so via this paragraph.

Compositions, formulations, intermediates, and/or products in accordance with one of more embodiments may be administered or applied in any suitable form including but not limited to, one of the following: a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary and/or cream, a foam, or combinations thereof, for example. Compositions formulations, intermediates, and/or products of, in accordance with certain embodiments, may also include an acceptable additive (e.g., one of a solubilizer, an antioxidant, a coloring agent, a flavoring agent, a plasticizer, a preservative, a sweetener, a thickener, and/or combinations thereof) and/or an acceptable carrier (e.g., one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). See, *Remington: The Science and Practice of Pharmacy*, Twenty-First edition, (Lippincott Williams & Wilkins; 2005) ("Remington's").

Implementations of compositions, formulations, intermediates and/or products may conveniently be presented in unit dosage form. Unit dosage formulations may be those containing a daily dose or unit, a daily sub-dose, or an appropriate fraction thereof. The dosage form may be administered, or topically applied—if so designed. A dosage unit may include sterile fossilized soil organic material (SFSOM) as described herein in any one or more of its possible permutations described herein.

As used herein, the term "ORAC value" refers to a measurement of the oxygen radical absorption capacity of a substance as determined in accordance with the method described in U.S. Pat. No. 7,132,296, and references cited therein, entitled "Method for Assaying the Antioxidant Capacity of a Sample" incorporated herein by reference in its entirety. See for example U.S. Pat. No. 7,132,296 citing (1) *Oxygen—Radical Absorbance Capacity for Antioxidants*, Cao, G., Free Radical Biol. Med. Vol. 14, (1993), incorporated herein in its entirety by this reference; (2) See, e.g. *Oxygen Radical Absorbance Capacity (ORAC) and Phenolic and Anthocyanin Concentrations in Fruit and Leaf Tissues of Highbush Blueberry*, Ehlenfeldt, M. and Prior, R., J. Agric. Food Chem., 49, pp. 2222-2227, (2001), incorporated herein by reference in its entirety; (3) *In Vivo Total Antioxidant Capacity: Comparison of Different Analytical Methods*, Prior, R. and Cao, G., Free Radical Biol. Med., Vol. 27, Nos. 11/12, pp. 1173-1181, (1999), incorporated herein by reference in its entirety; (4) *Total Antioxidant Capacity of Fruits*, Wang, H., Cao, G., Prior, R., J. Agric. Food Chem., 44, pp. 701-705, (1996), incorporated herein by reference in its entirety; and (5) *Antioxidant Capacity of Tea and Common Vegetables*, Cao, G., Sofic, E., and Prior, R., J. Agric. Food Chem., 44, pp. 3426-3431, (1996), incorporated herein by reference in its entirety.

The term "pharmaceutically acceptable" means that the active and inactive ingredients, additives, supplements, excipients, etc. independently have sufficient purity to generally and/or substantially satisfy the standards of USP-NF or the relevant portions of *Remington's*. As used in this document, "pharmaceutically acceptable" is a phrase used in its broadest sense and may describe ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, or botanical standards, for example. These standards may delineate acceptable ranges of aspects of ingredients of a pharmaceutical composition such as edibility, toxicity, pharmacological effect, ADMET properties, or any other aspect of a chemical, composition, or preparation used in implementations of a pharmaceutical composition.

As used herein, "pharmaceutically acceptable additive" and "additive" are terms used in their broadest sense. Particular implementations of the compositions described in this document may also comprise an additive (e.g., one of a solubilizer, an antioxidant, a coloring agent, a flavoring agent, a plasticizer, a preservative, a sweetener, a thickener, and combinations thereof) and/or a carrier (e.g., one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, croscarmellose cellulose, magnesium stearate, and silicon dioxide.

The phrase "therapeutically effective amount" means that a particular dosage may contain the active ingredient(s) in an amount sufficient to provide relief from a symptom, or it may provide a reduction, inhibition, or suppression of an adverse property, or conversely may provide an increase, induction, or stimulation of a beneficial property, or it may be effective in reducing the incidence and/or severity of a side effect.

According to one or more embodiments, various saccharides including the following monosaccharides or disaccharides may be one or more constituents of the compositions, formulations, intermediates, and/or products thereof: an aldose, a ketose, a triose, a pentose, a hexose, an allose, an altrose, arabinose, erythrose, erythrulose, fructose, galactose, glucose, glyceraldehyde, gulose, lyxose, idose, mannose, psicose, fucose, ribose, ribulose, sorbose, tagatose, threose, xylose, sucrose, and derivatives thereof and/or combinations thereof. Compositions, formulations, intermediates, and/or products may be admixed with pharmaceutically acceptable additives, carriers, diluents, actives, active medications, cosmetic ingredients, inert ingredients, any liquids suitable to be used in same as would be recognized by a person having ordinary skill in the art of making cosmetics, and the other types of compositions, formulations intermediates and/or products described herein including any and all of their permutations noted herein.

According to one or more embodiments, Organic Material (OM) from fossilized soil (FS) material may contain, optionally in chelated form, one or more of many monosaccharides including mannose, xylose, arabinose, galactose, fucose, N-acetyl-neuraminic acid, glucose, N-acetylgalactosamine, and N-acetylglucosamine. The chemical structures of such monosaccharides are provided below.

The structure for N-acetylglucosamine (NAG) can be represented by Formula 1:

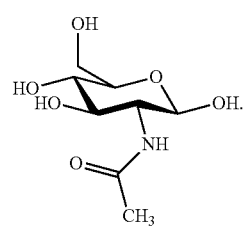

(Formula 1)

The structure for N-acetyl-neuraminic acid (NANA) can be represented by Formula 2:

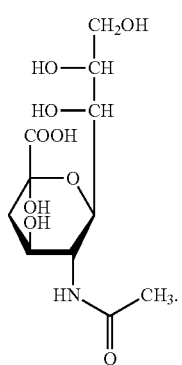

(Formula 2)

The structure of mannose (MANN) can be represented by Formula 3:

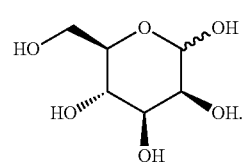

(Formula 3)

The structure for arabinose (ARAB) can be represented by Formula 4:

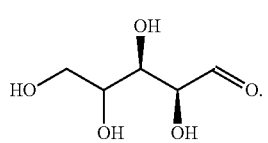

(Formula 4)

The structure for glucose (GLUC) can be represented by Formula 5:

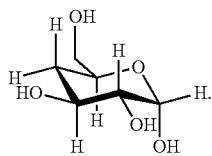
(Formula 5)

The structure for galactose (GALC) can be represented by Formula 6:

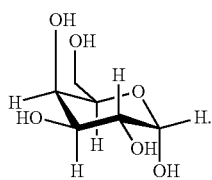
(Formula 6)

The structure for fucose (FUC) can be represented by Formula 7:

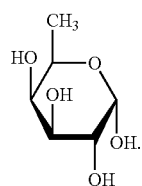
(Formula 7)

The structure of xylose (XYL) can be represented by Formula 8:

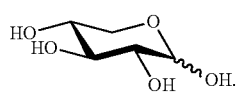
(Formula 8)

The structure for N-acetylgalactosamine (NAGA) can be represented by Formula 9:

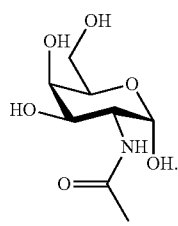
(Formula 9)

Each has a concentration ranging from about 9 parts per million (ppm) to about 38,240 ppm. In accordance with one embodiment of the presently claimed invention, the FS material may have a total monosaccharide content from about 67,500 ppm to about 74,800 ppm.

The dosage units may be in a form suitable for administration by standard routes. In general, the dosage units may be administered, by non-limiting example, by the topical (including buccal and sublingual), transdermal, oral, rectal, ophthalmic (including intravitreal or intracameral), nasal, vaginal, and/or parenteral (including subcutaneous, intramuscular, intravenous, intradermal, intratracheal, and epidural) routes. For the exemplary purposes of this disclosure, oral delivery may be a particularly advantageous delivery route for administration to humans and animals for implementations of a pharmaceutical composition, optionally formulated with appropriate pharmaceutically acceptable additives to facilitate administration.

The term "%" with respect to recovery is meant to be understood as follows: if a starting material contained 40% by weight of component B, and if the amount of that component recovered was 20% by weight, then the 20% by weight recovered represents a 50% recovery. Therefore, while the 40% by weight and the 20% by weight are percents by weight, the 50% recovery is a reflection of ((20% divided by 40%) times 100) which is equal to a 50% recovery. The % recovery, therefore, is not a % by weight value.

Also, the 20% by weight versus the 40% by weight values may also have to be normalized to reflect a comparison of the appropriate weight of component B recovered minus any counter ions, chelates, salt forms, or hydrates thereof because the weight of such counter ion, etc. would lead to incorrect % by weight values. Thus, if component B is recovered as its chloride salt form B-Cl or its hydrated form $B.6H_2O$, then the weight of the chloride counter ion (Cl) or the weight of the six (6) water molecules ($6H_2O$) would have to be adjusted to reflect the correct % by weight recovered because neither the counter ion (Cl) nor the six (6) hydrated water ($6H_2O$) molecules were associated with the original 40% by weight of B in its host molecule prior to recovery of B as a decoupled component. Alternatively, the weight % values can be expressed as molar values and thus normalized for one or more active components.

Accordingly, % values are % by weight (((weight of part)÷(weight of whole))×100) when so indicated. Also, % values are also correctly used herein as recovery % values. It will be apparent to those of ordinary skill which values are % by weight values and which are recovery % values. Also, any % by volume value (((volume of part)÷(volume of whole))×100) will be so recited in express manner if the percent value is intended to be a % by volume value.

The % by weight values recited also correspond to the percentage of the particular component when compared to the total weight of the whole molecule being set at 100%, or compared to the total weight of the whole formulation being set at 100%—depending on whether the relevant component was part of its host molecule or whether the relevant component was part of its host formulation. Accordingly, if a particular oligosaccharide X is made only of monosaccharides A, B, C and D and is said to contain 40% monosaccharide B, then the 40% reflects the value of the number of individual constituent monosaccharides B present in the entire oligosaccharide X. Thus, if the number of As+Bs+Cs+Ds=50 total monosaccharides of the oligosaccharide X, then 40% B reflects that among the 50 total monosaccharides, one will find 20 monosaccharides B in oligosaccharide X with the remaining monosaccharides As+Cs+Ds=30 monosaccharides. Using the foregoing numbers, further clarification is provided as to % by weight values as used herein.

Given that there are 20 monosaccharides B in oligosaccharide X, the percent by weight of B in oligosaccharide X would be: (((20 times the Molecular Weight of B) divided by (the total Molecular Weight of oligosaccharide X)) multiplied by 100))=% by weight of B in oligosaccharide X. In other words "40% B" refers to 20 units B in an oligosaccharide X with 50 units in total. As a clarifying point, therefore, this "40% B" does not reflect a 40% by weight of B in relation to the "total weight" of the oligosaccharide X (where such "total weight" would be considered 100% of the weight of oligosaccharide X).

According to one or more embodiments, various saccharides including the following monosaccharides or disaccharides may be one or more constituents of the compositions, formulations, intermediates, and/or products thereof: an aldose, a ketose, a triose, a pentose, a hexose, an allose, an altrose, arabinose, erythrose, erythrulose, fructose, galactose, glucose, glyceraldehyde, gulose, lyxose, idose, mannose, psicose, fucose, ribose, ribulose, sorbose, tagatose, threose, xylose, sucrose, and derivatives thereof and/or combinations thereof. See *Remington's* which is incorporated herein by reference in its entirety. Thus all possible permutations with the listed actives in *Remington's* are contemplated.

The % by weight values provided herein are % by weight of a given ingredient compared to the total weight of the entire composition being set at 100% or the total weight of the relevant formulation set at 100% unless indicated otherwise. In that context, please see paragraphs noted above relating to frequency and recovery % values provided. Those frequency and recovery % values are not % by weight values as a percent of the total weight of the relevant claimed or described composition, or formulation.

Thus, without being bound by any theory, the leaf disintegration illustrative description is provided herein below merely as an illustrative example of plant material disintegration and/or incorporation thereof into soil. This illustrative description may be applied to other plant materials by analogy, if possible. Leafless plants (e.g., cacti), for example, are not excluded from the meaning of "plant material" in the context of "sterile fossilized soil organic matter" (SFSOM). Thus, if the particular soil were hypothetically soil from a location where no trees grew or where only leafless plants grew, then this leaf illustration does not exclude soil from such locations so long as the soil is sufficiently suitable for forming one or more "sterile fossilized soil organic matter" (SFSOM) embodiments of the claimed invention.

Nevertheless, even if the leaf analogy is not readily applicable or inapplicable to a particular plant (e.g., leafless cactus) or leafless plant part (e.g., root, bark, or dead leafless branch), the use of the leaf illustrative example provided below will not limit the scope of the claimed invention in any respect. In addition, the applicable words and phrases (when recited alone or when recited in any permutable combination thereof): (1) "soil" (S), (2) "plant", (3) "fossilized", (4) "organic", (5) "matter", (6) "sterile", (7) "plant material", (8) "fossilized soil" (FS), (9) "organic matter" (OM), (10) "fossilized soil organic matter" (FSOM), (11) "fossilized nutrition" (FN), and/or (12) "sterile fossilized soil organic matter" (SFSOM), do not exclude "non-leaf" plant material. Subject to the foregoing, the nonlimiting leaf illustration of the leaf disintegrating and/or being incorporated in the soil is provided below.

Leafy Plants, Non-Leafy Plants, Leafy Parts, and Non-Leafy Parts

The leaf illustration is provided herein (as opposed to a root or a bark or some internal woody part of a material, or a leafless plant) because it lends itself to a description readily understood. It is merely illustrative and therefore the leaf illustration is not limiting as to any leafy plants or any non-leafy plant parts.

Types of plant materials suitable for use in conjunction with the claimed invention may include, but are not limited to, plants growing in swampy areas or in Florida everglades, a "mangrove" tree/bush/plant or a tuber, a tumbleweed, a cactus, a seaweed, an algae, bark, root, fruit, tree parts other than leaves, flowers, beans, corn, seeds, a plant entirely grown underwater, any non-leafy plant or non-leaf plant part, etc. by inclusion of the leaf illustration. The inclusion of the leaf illustration is not intended to limit the scope (or exclude non-leafy plants and parts) of any of any terms or limit the scope of any claims of this application.

Sufficiency of Soil

Also inclusion of the leaf illustration does not limit the type of soil used. If suitable, the soil could be soil that is under fresh water, under sea water, in a lake bed, a river bed, and/or in a desert, etc. Preferably the soil is fossilized soil (FS) rich in plant material or plant derived material.

If the soil is suitable to form the compositional embodiments, formulational embodiments, and or intermediate embodiments, then the soil is sufficiently suitable unless expressly excluded otherwise. Thus, the location of the soil of interest is not necessarily limited in any way unless expressly recited otherwise. Thus, the leaf analogy does not limit the scope of the claimed invention only to soils in environment(s) where trees or plants typically drop their foliage during the fall season followed by a cold winter where snow and/or ice usually accumulate during the winter months to aid in disintegrating and/or integrating the leaf into the soil.

Non-Limiting Leaf Illustration

This leaf analogy relates to the disintegration of a leaf in the context of its partial disintegration and integration into soil. It is well-known that a typical single leaf (e.g., a maple leaf, a oak leaf, a leaf from a flowering plant, etc.) has a leaf stem, a leaf perimeter, and leaf veins forming a web-like leaf support structure. Upon and/or within the web-like leak leaf support structure, leafy tissue (e.g., green leafy tissue, for example, herein called the "leaf fabric" at times) is supported. The leaf fabric is structurally, integrally and physically connected as well as functionally integrated as a part of a living photosynthesizing tree when attached as a normal living functional leaf of the plant's normal foliage.

Each spring, new plant growth accelerates together with nature's display of vibrant spring colors most readily recognized in the form of spring flowers, fruits, and new foliage. Later on, in preparation for the upcoming winter, much of the spring foliage is ready to fall, but not before another display of spectacular fall colors. By winter, most of the foliage has dropped to the ground as the autumn season ends. In winter, with its associated snowfalls, ice storms and/or winter rains combined with winter winds and other winter temperature fluctuations, the prior spring's vibrant foliage, fruits and flowers are just a distant memory.

However, for the fallen foliage in contact with earthen soil below, that foliage is pressed into the ground beneath it (in part) due to the weight and disintegrating forces exerted by snowfall and ice formations accumulated on top of the dropped foliage. In the wet winter environment, the compression (or pressing force) applied to the fallen foliage sandwiched between ice/snow on top and dirt on the bottom increases under the weight of accumulating winter snows and ice. When combined with normal daily and seasonal climate fluctuations, the fallen foliage is further subjected to varying melt-thaws, varying pressures, varying temperatures, varying winds and other climatic fluctuations. By the time winter is over and the next spring begins, the past year's foliage is typically disintegrated to varying degrees consistent with climatic variations.

For example, a green newly-fallen leaf can be aged to a brown, somewhat brittle or even soft form, a state far from its verdant supple state when alive, or even just after freely falling to the ground. At this point, the original green "leaf fabric" of the leaf has developed an autumnal hue, which may be brown, yellow, red or some combination thereof, but it still may be essentially intact, with its perimeter, stem and supporting leaf veins all undamaged. Further, the same brown leaf now can be aged beyond such freshly-fallen state (e.g., from its original intact green leaf fabric like supple state) into a further disintegrated state with the leaf fabric almost entirely gone, leaving behind just the "leaf web" of dried veins, perimeter and stem. At this aged leaf web state, the supporting leaf stem, leaf perimeter and leaf vein structure are essentially intact, but the leaf fabric has mostly been disintegrated into the surrounding soil.

Leaves in such a web-like disintegrated state are commonly found. The described progression from the original green leaf into its web-like state is a result of the combined effect of various natural forces, including, but not limited to: (a) drifting onto the ground as fall foliage (or otherwise); (b) exposure to climatic forces including varying pressures, temperatures, snowfalls, snowfall accumulations, ice formations, ice accumulations, winds, rain, gravel, abrogation, etc.; together with (c) exposure to earthen microflora and microfauna in a wet, possibly low light damp environment. Ultimately, (d) atmospheric temperatures begin to rise as winter thaws and the next spring season arrives, and (e) with increasing temperatures, the natural microflora and microflora found in healthy earthen soils further accelerate breakdown of the prior year's fallen foliage and other plant material. Such microbial breakdown is evidenced by the level of disintegration found in fallen leafy foliage that is dependent on the degree of breakdown. Imagine again a just fallen, nearly intact leaf (in the first days of the fall season) as compared to its latter web-like state as winter wears on.

Nevertheless not all leaves are disintegrated into the web-like state at exactly the same time. So it is fairly clear that natural disintegration processes and integration processes of plant material into soil are subject to variations of plant age, cumulative effect of climatic conditions year after year (e.g., see for example the Farmer's Almanac weather data from years gone by; and also see weather data maintained by the U.S. National Weather Service), the prior season's climate conditions, the identity of microflora and microfauna existing at a given soil site, rain fall at such site, current climatic conditions at such site, nutrients available to the microflora and microfauna, competition between microflora and microfauna at a given soil site, etc., and the numerous variations thereof.

Returning to the foregoing non-limiting illustrative leaf disintegration description, such disintegration emphasizes the effect of only one year's time on one leaf in a number of possible permutations sufficient to disintegrate and incorporate plant material in earthen soil. The foregoing description provides a description of how the fabric of the fallen leaf weakened to such an extent as to separate from its leaf stem, leaf perimeter, and leaf veins. It is expected that the separated leaf fabric (depending on how brittle or weak it may be) will likely break into smaller pieces and/or be further broken down by the earthen microflora and microfauna to be further incorporated into the nearby soil. By having so separated, the fabric of the leaf is mostly integrated into the soil itself. Ultimately, over many years, soils may incorporate plant material to varying degrees. Compare, for example, sand in a desert versus a dark porous loam found in a thriving forest.

One can take into account each season past, and consider the corresponding accumulation of each season's fallen foliage and other plant material, their degree of disintegration and accumulation into the soil at iteratively different levels, and the cumulative effect of climate changes, pH changes, various nutrients in the soil, the microflora and microfauna inhabitations from year to year, etc. Thus, older soils may have greater plant material at more advanced stages of breakdown and integration where conditions are ideal.

With that noted, one might also consider the foliage from prior years (fallen long before the most recent winter-spring-summer-fall seasonal cycle) continuing to disintegrate at successive varying rates. Accordingly over years and years, the cumulative effects of varying rainfalls, snowfalls, amount of forestation, available sunlight, amount of falling foliage, and other factors at the soil site can have an impact on the degree to which a particular soil site can integrate plant material into the nearby soil.

For example, consider the effect of variable conditions from year to year such as: successively greater contact time with soil, changing identity and quantities of soil microflora and microfauna, changing nutrient availability, quantities of accumulated and accumulating plant material from year to year, stage of breakdown of products and breakdown of byproducts of accumulated and accumulating plant material, age of soil, degree of "fossilization" due to volcanic action, geographic location of soil, depth of soil relative to surface, disintegration state of plant material, cumulative effects of climate conditions and variations, pH of soil, competition between microflora and microfauna vying for the same nutrients, or any other factors and/or variations thereof. When considered on the scale of geological time frames, one can readily imagine that geological processes may have already contributed to the degree of fossilized soil content. Taken together, "fossilized" soils enriched with plant material can be formed. However, because the soils formed are subject to the influence of many variable conditions, it becomes important to locate soils with desired constituent properties of interest.

In part by virtue of their contact with the natural action of earthen soils and the microfauna and microflora in the soil itself, soils rich in plant material may be formed where water and climate may be suitable for same. In addition, due to forces associated with "fossilization," a soil presently in a very hot and dry location may be a soil rich in plant material, for example, because such soil may have been at one time (hundreds, thousands or hundreds of thousands of years ago) situated in a tropical climate—even though today such soil is in the middle of a desert. And over geological time frames, the plant materials became "fossilized" in such soils. In such case, some such "soils" could be suitable for use in conjunction with the certain embodiments disclosed herein, irrespective of being located in a desert today. A suitable soil is one that may be rich in plant material and/or rich in fossilized plant material sufficient to use for one or more of the compositional embodiments described herein. Preferably, the soils sought may be those soils with fossilization sufficient to provide at least one embodiment as described herein.

The "fossilized soils" may include plant material of varying amounts. Some of the plant material may be fossilized plant material suitable for formation of the compositional embodiments described herein or described herein for formation of compositional embodiments. The plant material in such soils may have become "fossilized" over the years under natural compressive "forces" or volcanic or tectonic events, and may have the beneficial properties and uses of preserving plant material in "fossilized" form.

Eventually, accumulated plant materials disintegrate and are broken down by the natural biological processes associated with earthen microflora and microfauna found in soils in combination with the other forces described herein. Accordingly, some soils may be rich in plant materials while others may not be so enriched. For example, a surface layer of desert sand (e.g., sand from the hottest, most arid and least hospitable part of the Sahara Desert at its most severe waterless spot; or desert sand from an equally inhospitable location elsewhere) would likely be considered soil poorly enriched by plant material.

As it turns out, if all other things are kept equal, applicants have discovered that soils containing greater amounts of fossilized plant material are preferable over those that are less fossilized.

However, one might correlate some weighted value to factors which may be more influential than others for producing soils with greater fossilized organic matter. Then if properly aggregated, those soils with the larger total weight could indicate greater fossilized content because those factors that were more influential (for fossilization) were given greater weight.

The foregoing description may be related to the various uses of the formulations and/or compositions described herein when administered or applied or used by persons in need of the associated benefits of such formulations, compositions and/or intermediates herein-described. Thus, one may consider the various beneficial uses of the compositions, formulations, and/or intermediates herein-described together with their various uses among various sub-populations of individuals in need of the beneficial aspects of selected compositions, formulations, and/or intermediates herein-described.

Examples of some of the formulation(s) for use in connection with embodiments of the presently claimed invention may be sweeteners, taste modifiers, sugar substitutes, nutritional supplements, dietary supplements, and/or cosmetics among others described herein, respectively, that may include preferred intermediates useful for the production of the herein-described formulation(s). Certain compositional embodiment(s) may include one or more preferred intermediates used for the production of the formulation(s) described herein. For example, a specific compositional embodiment may be a sugar substitute formulation and/or sweetener formulation described herein.

Fossilized soil (FS) derived organic matter (e.g., by a process of separation, purification, collection, isolation, and/or extraction) may be obtained from (FS). Such (FS) derived organic matter may provide the requisite fossilized soil organic matter (FSOM) which may be used in the production of intermediates or other compositions. The intermediates formed may be used in the production of certain compositions, formulations, or both. Certain compositions may be used to produce formulations or the compositions themselves may be the formulations in some cases. The so formed compositions and formulations may be administered to a patient in need thereof. Examples of beneficial uses of administration or topical application of suitable formulation(s) may be associated with medicinal, nutritional, cosmetic, and/or sugar-substitute or sweetener properties thereof.

For example, certain colors or shades of cosmetics may be matched to a certain population with matching skin colors, tones, etc. Thus, the color and shade of the cosmetic can provide certain benefits to some and not to others as a matter of choice and design preference.

A human population with a condition in need of treatment or relief may be treated or relieved provided the administration (e.g., ingestion) or application (e.g., topical application) of a formulation is suited to provide the requisite treatment or relief. For example, consider a population suffering from eczemated skin with associated itching. Their specific skin condition may dictate the need of an anti-itching formulation or need of a eczema skin condition treatment formulation including, but not limited to, providing one or more of the following: improved skin healing, reduced scarring, reduced incidence of skin rupture, reduced itching, and/or improved softness, reduced dryness, or other benefits as may be identified by a dermatologist or the suffering individual(s) in search of a benefit, or in need of a treatment, or some sort of other relief.

Another example may be a population of individuals suffering from diabetes or like metabolic syndrome in need of using a sugar substitute or sweetener. In the case of a person with a diseased state, the need may not just be a preference, but need to resolve the diseased state, either through a cure, a treatment, or even relief of a particularly bothersome or severe symptom, side-effect, and/or complication. Typically, the more severe the diseased state or the suffering associated with it, the greater the need irrespective of the preference. In the context of a medicament, the phrase "in need thereof" typically refers to an afflicted person "in need of" the benefits of the medicament which, in contrast, is not needed nor wanted in a person not afflicted with the particular disease state, complication, and/or side-effect. In the case of a sugar substitute and/or sweetener embodiment, the need may be established. In the case of a cosmetic formulation embodiment, the need may be a preference.

In the context of a diabetic, there may be a range of choices of sugar-substitutes available. The diabetic "in need thereof" may have a preference of any single available sugar-substitute. The need may also be a preference for a particular sugar-substitute in part due to the unpleasant or bland taste of beverages, teas, coffees, and other liquid drinks sought to be improved, changed and/or masked. Nevertheless, a sugar-substitute could also be used by a non-diabetic to reduce sugar intake as a weight control measure by a dieting individual.

Whereas, in the context of a life-threatening condition, a medicament such as a blood glucose controlling drug is a medical need without which the patient would ultimately suffer consequences or even pass away if the required medicament is not timely ingested. However, in the case of a non-life threatening condition such as "eczema," a topical drug may be indicated arising from severity and type of the affliction in question.

Reference will now be made in further detail with respect to one or more compositional embodiment(s), formulational embodiment(s) and/or intermediate(s). But before doing so, we return to the hypothetical illustration of the extraction problem herein-described.

Hypothetical Example of Extraction Problem, Extraction Limit and Solution to Same Suppose a composition requires 20% yield of monosaccharide B from the multi-monosaccharide containing 40% B. And suppose the soil extraction process only provides 11% monosaccharide B. The recovered 11% of desirable monosaccharide B via extraction is simply not enough to satisfy the 20% recovery requirement. If the sought amount (20% B) is too far above the actual extractable amount (that is, the extraction limit is too low to extract higher amount sought), then a different approach might be warranted given that the hypothetical extraction limit is 11% B (a number just barely over the half-way mark of the necessary recovery of 20% B). The 9% hypothetical shortfall is used in this continuing hypothetical to illustrate a problem elegantly solved by applicants' invention.

Hypothetical More Accurate But with Lower Extraction Limit Confirmed Indicating Shortfall Due to Extraction Limit Now suppose the best extraction limit were only 7% instead of 11%. Then that 7% extraction limit is even worse than originally expected, possibly because it turns out that only 7% B can reasonably be extracted pursuant to the applicable extraction limit of 7% instead of the 11% initially thought possible. Such a situation can arise especially if the lower 7% extraction limit were determined to be the true limit upon proper calibration and repeated extractions conducted to check and double-check that the proper extraction methodology, solvent combinations, and extraction parameters were used. Thereby, with repeated extraction cycles, the results can be used to verify that the extraction is actually 7.04% instead of the 11% originally noted, and that no procedural or technical error led to the discrepancy between the confirmed 7.04% recovery versus the initial 11% recovery rate now known to be incorrect.

In such instance, another 13% B is still needed to satisfy the required 20% recovery. The 13% B shortfall could be supplemented in some fashion other than by extraction. Suppose that with repeated extraction cycles one could improve yield, but only with much lower efficiency, higher associated cost, and possibly without the high throughput levels sought. Thus, even with additional extraction cycles, due to the fact that each successive extraction cycle is typically less efficient than the former, the efficiency of repeated extractions may still be insufficient to provide the 20% recovery of B.

Atypical Solution to Hypothetical Problem When Extraction Limit Inadequate as Illustrated by Hypotheticals Presented Where a soil sample may have multiple monosaccharides, where some may be less desirable than others for example, additional approaches to solving the extraction limit problem may prove to be successful where other solutions were ineffective as illustrated by the hypotheticals presented and described above.

For example, one may be able to convert a less desirable monosaccharide A into the more desirable monosaccharide B to supplement the 7% B recovered (in view of the 7.04% B hypothetical extraction limit), and thereby make up for the 13% shortfall needed to satisfy the 20% B recovery requirement. In effect, one might convert a less desirable monosaccharide A into the more desirable B, and supply the entire 13% recovery shortfall. By doing so, the less desirable monosaccharide A content might be effectively lowered while at the same time the amount of the more desirable monosaccharide B recovery increased. Such approach may provide the 13% needed to get to the 20% B recovery requirement, and may provide a possible solution. In this instance, the conversion would be in the favorable direction sought, evidenced by a decrease in the less desirable monosaccharide A being converted into the more desirable monosaccharide B, thereby increasing its content to the 20% B needed by weight pursuant to this hypothetical.

Potential Solution to Hypothetical Extraction Limit Problem

Nevertheless, one may be able use to one's advantage a particular result in an unexpected way previously considered a dead end. Until now, the solution to the extraction limit problem appeared to be insurmountable. In effect, it might be possible to turn the conversion problem (encountered with the "Decoupling Approach") to one's advantage and couple that with extraction to overcome the extraction limit problem as well.

Here the applicants discovered that the conversion of one monosaccharide into another as previously illustrated in the context of the "Decoupling Approach," was not the problem, but rather the solution, if one could promote the favorable conversion of A to B. The conversion may then be enough to overcome the extraction limit problem of only recovering 7% B rather than recovering 20% B. In essence, it may be possible to combine two problematic approaches in a novel and surprising way to solve the Decoupling Approach difficulties and overcome the 7% extraction limit difficulties, and, at the same time, provide the sought 20% recovery of the monosaccharide B.

It may be possible to improve collection efficiencies of monosaccharides sought by converting a different less desirable (generically labeled as) monosaccharide A into the more desirable (generically labeled as) monosaccharide B. So even if the amounts of monosaccharide B extractable under the hypothetical extraction was limited to about 7% B, such limit could be overcome using a favorable conversion of A to B. Such combined solution could be enough to boost the recovery to 20% in a way to bypass the 7% B extraction limit.

Embodiments of Methods and Processes

Pursuant to one or more process embodiments, one or more of the foregoing compositional embodiment(s), formulation(s) and/or intermediate(s) may be made by the inclusion (or addition) of certain organic matter obtained (e.g., collected, separated, harvested, extracted and/or isolated) from select soils (e.g., soils which may be rich in plant matter, plant breakdown products and/or plant breakdown byproducts together with or without other soil constituents). The organic matter so obtained from these soils may be converted into other more suitable forms useful for the production of one or more of the aforementioned formulation(s), compositional embodiment(s) and/or intermediate(s). Isolating selected organic matter from certain soils (e.g., soils which may be rich in plant matter, plant breakdown products and/or plant breakdown byproducts) may be accomplished by various separation techniques including extraction.

Soil Selection for Solvent Extraction

Without being bound by theory, the preferred soils may be those soils that are rich in (or richer in) the quantity, age and/or type of plant material, plant breakdown products and/or plant breakdown byproducts present therein, either as fossilized or non-fossilized organic material. Likewise without being bound by theory, the supply of plant material present in the soil may continually (or may continuously) be undergoing breakdown in the presence of the microbial life (e.g., by way of one or more of bacteria, fungi, yeast, mold etc.) living (or present) in the soils under the conditions the soil was exposed to over the course of its geographic history. It is also possible that the breakdown of plant material into plant breakdown products and byproducts may be enhanced under certain soil conditions including, but not limited to, water content, soil drainage, longitude and latitude of soil location, soil density, sand content, salt content, salt type(s), mineral content, elements present, metals presents, other soil constituents present or absent, soil pH, clay content, soil type, soil porosity, age of soil, depth of soil sample, temperature, pressure, sunlight, duration of day, climate zone, extent of aerobic or anaerobic surroundings, the quantity and identity of microbial life active in the soil, nutrients present, nutrient quantity, any changes in one or more of the above over time, and/or some other parameters including any combination or sub-combination of any of the above.

In accordance with another embodiment, the fossilized soil (FS) may be native to North America. According to another embodiment, the (FS) is native to Mt. Olive, Miss. Locations that may be used for (FS) collection are situated on two approximately 20+ acre (e.g., about 22.5 acre; and/or about 22.8 acre) land parcels. The first land parcel where the fossilized soil (FS) may be collected is at longitude 89°39'13"W and latitude 31°45'24"N or within a radius of about 10 acres in any direction from the parcel's center. The second parcel where the fossilized soil (FS) may be collected is at longitude 89°39'13"W and latitude 31°45'24"N or within a radius of about 10 acres in any direction from the parcel's center.

The "organic matter" or (OM) in question may be obtained from certain soils that may contain "fossilized" organic material. The "organic matter" in question may also be obtained from certain soils that may contain plant material, plant breakdown products and/or plant breakdown byproducts.

One or more non-limiting and illustrative embodiments of the presently claimed invention may be directed to compositions containing certain "organic matter." The "organic matter" in question may be obtained from certain soils that contain "fossilized organic material." Such "fossilized organic material" in question may be obtained from fossilized soil (FS) samples containing breakdown products and breakdown byproducts of disintegrated plant material within the soil. As an option, the soil samples may also contain materials of (a) plant origin, (b) plant origin and/or any other origin excluding animal origin, (c) plant origin only, (d) animal origin only, and/or (e) a combination of plant and animal material.

The term "organic matter" (OM) optionally may be understood to collectively refer to the group of embodiments of "organic matter" corresponding to (i) plant materials, if any, (ii) plant breakdown products, if any, (iii) plant breakdown byproducts, if any, and/or (iv) any other constituent that is extracted via solvent extraction from a fossilized soil sample or from a non-fossilized soil sample with plant material in various stages of breakdown when extracted with an aqueous extraction solvent (or when extracted with an equivalent substitutable aqueous and/or organic extraction solvent) under the extraction conditions noted herein (or equivalent substitute extraction conditions) sufficient to provide one or more of the compositional embodiments described herein.

Examples of "soils" that may fall into certain other soil sub-categories include, but are not limited to, soils containing (i) material of plant origin plus soil constituents, (ii) material of plant origin alone plus soil constituents, (iii) material of plant origin alone plus soil constituents but excluding material of animal origin, (iv) material of plant origin plus other constituents in a multitude of combinations to satisfy any one possible combination corresponding to each permutation specified herein (i.e., within this entire application) and/or in each of TABLES 1-10 detailed herein. See further descriptions provided herein.

The "soil derived organic matter" (SDOM) may be obtained from selected soils rich in plant material, rich in plant breakdown products and/or rich in plant breakdown byproducts. More specifically, the soil derived organic matter (SDOM) may be extracted from selected soil organic matter (SOM), and/or selected fossilized soil organic matter (FSOM), the latter two (SOM) and (FSOM) being rich in plant material content. The adjective "fossilized" in the phrase "fossilized soil organic matter" (FSOM) typically indicates that the "soil" contains "fossilized" plant material and/or "fossilized" plant breakdown products and/or "fossilized" plant breakdown byproducts and that such "soil" may or may not contain other "fossilized" soil constituents.

Pursuant to one embodiment, the "organic matter" in question may be obtained from certain soils that may contain fossilized organic material from any source including material originating from the animal kingdom or part thereof. The "organic material" in question may also be obtained from certain soils that may contain fossilized organic material from any source including material originating from the plant kingdom or part thereof. Other illustrative non-limiting embodiments may be embodiments of "organic matter" suitable for use in conjunction with the claimed invention wherein the "organic matter" excludes organic material containing material derived from animals. These variants may be useful, for example, since persons with strict vegetarian requirements may only wish to ingest or apply products they know are strictly vegetarian or vegan.

Fossilized Organic Matter of Plant Type and Breakdown Products and Fossilized Breakdown Byproduct Thereof The "organic matter" in question may also be obtained from certain soils that may contain fossilized plant material, fossilized plant breakdown products and/or fossilized plant breakdown byproducts. For example, such fossilized "organic matter" may contain plant material, plant breakdown products and/or plant breakdown byproducts. The "organic matter" may include those decomposition products which may be formed when plant material is mixed with soil to promote plant matter breakdown when left in such soil over enough time to form rich soils.

The breakdown time may be from one month to one season, from one month to one year, from 1 to 10 years, from 10 to 20 years, from 10 to 30 years, from 10 to 40 years, from 10 to 50 years, from 10 to 60 years, from 10 to 70 years, from 10 to 80 years, from 10 to 90 years, from 10 to 100 years, from 10 to 200 years, from 10 to 300 years, from 10 to 400 years, from 10 to 500 years, from 10 to 600 years, from 10 to 700 years, from 10 to 800 years, from 10 to 900 years, from 10 to 1000 years, from 10 to 5000 years, from 10 to 10000 years or more commensurate with geological time frames necessary for soils to become fossilized in some embodiments. The breakdown time may be the amount of time that all of the original plant material has substantially decomposed or has completely decomposed. The amount of breakdown time may be extended to the amount of time it has taken for plant material left in sediment (on day 01 of year YYYY) to ultimately form a fossil (on day "DD" of a particular year "$YYYY_i$," where $YYYY_{i\text{-}n}$=years to form the sought fossilized soil; i=individual year, n=1, 2, 3, 4, ... 10,000,000-2, 10,000,000-1, and 10,000,000).

Fossilized Organic Matter of Plant Type Excludes Animal Kingdom Origin Organic Matter Altogether, or Excludes More Than 10% by Volume Animal Kingdom Origin Organic Matter Optionally, the fossilized organic material (from soils of interest) may include fossilized organic material that originated from the plant kingdom or originated from any material but may not contain (or may not contain more than 10% by weight) fossilized organic material that originated from the animal kingdom. Examples of fossilized organic material that may be included under this option may include fossilized tree parts, fossilized seaweed parts, fossilized mushroom parts, fossilized non-animal parts, fossilized grass parts, fossilized plant parts, fossilized foliage parts, fossilize seed parts, fossilized fern parts, fossilized root parts, fossilized woody parts, fossilized flower parts, fossilized fruit parts, and/or any other fossilized parts of any species or genus of the plant kingdom, but not any fossilized parts of any species or any genus of the animal kingdom above 1%, 2%, 3%, 4%, 5%, 6%, 7%, 8%, 9% or 10% by weight, respectively. These same numbers may be applied to exclude insects, fish, arthropods, zooplankton, crustaceans, and other sea creatures. Alternatively, one or more of the foregoing species or classes may be optionally included.

Fossilized Organic Matter of Plant Type

Optionally, the fossilized organic material (from soils of interest) may include: grasses, weeds, any leaf, any flower, any seed, any seed pod, any outer plant or fruit layer, bark, juice, pulp, outer scales, needles, thorns, petals, flower stamen's, pollen, stems, branches, wood, limbs, connective tissue, sap, syrup, roots, or other plant parts, etc., irrespective of whether the plant is alive and growing in open-air, underwater, underground or elsewhere so long as such fossilized parts are of a species or of a species relying on photosynthesis or requiring sunshine to grow, which would generally be a vegetable, a grass, a plant, a fruit, a root, a seed, a bean, a string bean, corn, corn husk, husk, a leaf, a branch, a bark, an under-layer or internal part of any plant thereof, and/or any combination thereof.

Fossilized Organic Matter Excludes Dairy Products such as Pasteurized Milk Having Animal Origins (Cow Milk, Goat Milk, Mother's Milk, Etc.)

As another option, the fossilized organic matter may exclude parts originating from an animal so as to exclude dairy products such as cheese, non-vegetarian butter, fat, regular milk, skim milk, butter milk, organic milk, double pasteurized milk, pasteurized milk, whey, curd, any pasteurized fluid, or any pasteurized product having animal origins. Fossilized parts under this option exclude cow milk, goat milk, mother's milk, or milk from any other animal and products made from animal milk. However, pursuant to this embodiment, the fossilized parts may not exclude the pasteurized parts originating from non-animal sources.

Fossilized Organic Matter Optionally Excludes Soy Milk, Milk from Any Plant, Aloe Gel, Gel, Plant Exudate, Amber, Syrup, Etc.

Under this category, the "fossilized" organic matter may optionally exclude one or more of: soy milk, milk from any plant (i.e., the fluid that is exuded by a plant and appears white in color very similar to the consistency of cow milk), maple syrup, plant syrup, gel, aloe gel, any fluid oozing from a plant, any plant exudate, any plant exudate that either has an amber-like or amber appearance when hardened, or has a milk-like appearance, and/or, plants and parts thereof exuding such exudates, syrups, milks, fluids, as well as plants from the group including: aloe vera, oak, cherry, maple, pine, etc.

Extraction Solvent May Be Polar Solvent Including Non-Limiting Choices for Same

With respect to isolating, separating or extracting "organic matter" from "fossilized soils," the extraction solvent may be a polar solvent. Examples of such solvents include, but are not limited to, distilled water, de-ionized water, tap water, water of any quality sufficient to conduct sufficient extraction without materially interfering with commensurate operational efficiency. Water locally collected from the same site or near the site where the soil sample is collected (or is intended to be collected from) may also be used. Without being bound by theory, it may be possible that the local water may provide certain advantages. Again, without being bound by theory, an advantage may be that local ground water, if used, avoids the need to transport water. Likewise, without being bound by theory, another advantage may be that the local ground water could contain and/or be better saturated with "organic matter" sought and/or other soil constituents sought to be extracted out of the soil. Once again, without being bound by theory, yet another benefit of using local ground water from the site of soil collection may be that those soil components present in very low concentrations could be more easily extracted because the local ground water had been in longer contact with the local soils of interest.

On the other hand, if in a given local environment, the pH of the local ground water is either in an acid range, at neutral pH, or a basic range, then it is possible that the ground water may not extract a sought soil constituent because the ground water may be too acidic, too basic or at the wrong pH to extract a given soil constituent of interest. Acid pH ranges are anywhere up to pH=7, whereas basic pH ranges are anywhere above pH=7 up to and including 14. Sub-ranges of acidic pH include, for example, pH=about 1+, about 2+, about 3+, about 4+, about 5+, about 6+, with an upper limit of about 6.8, 6.9, right up to 6.999, respectively. Neutral pH=7. And basic pH sub-ranges include, for example, pH=about 7+, about 8+, about 9+, about 10+, about 11+, about 12+, about 13+, about 14, or somewhere in the range of about 7.01-14, about 8-14, about 9-14, about 10-14, about 11-14, about 12-14, or about 13-14, etc.

In addition, local ground water may contain certain pre-dissolved constituents. And, when such pre-dissolved constituent is reacted with or comes in contact with a given soil constituent of interest, the pre-dissolved ground water constituent may react with the sought soil constituent to form a precipitate so that the sought soil constituent in not amenable to extraction with the local ground water with its pre-dissolved constituents. Thus, it may be better to use water that has been treated to remove interfering pre-dissolved soil constituents or to use distilled water, de-ionized water, distilled and de-ionized water, water at a neutral pH, water at an acidic pH, water at a basic pH, or even water mixed with a co-solvent. The co-solvent may be a water-miscible co-solvent better suited to extracting the sought soil constituent(s) of interest. Co-solvents can include organic solvents such as, but not limited to, alcohols (methanol, ethanol, and the like), dimethylsulfoxide (DMSO), N,N-dimethylformamide (DMF), acetonitrile, tetrahydrofuran (THF), p-dioxane, and the like.

Accordingly, it may be that rather than using local ground water it may be better suited to use water without interfering pre-dissolved constituents, water at a given pH, and/or water mixed with a co-solvent, etc. Thus, the water used for extraction may have its pH adjusted to an acidic, neutral or basic pH, if necessary to extract a particular soil constituent.

Various Forms of Water as Extraction Solvents, Co-Solvents and Relevant Parameters for Extraction Examples of aqueous solvents that may be suitable for use in accordance with one or more embodiments of the presently claimed invention may include, but are not limited to, the following: (1) potable water, (2) de-ionized water, (3) distilled water, (3a) distilled and de-ionized water, (4) water at physiological pH matched to physiological osmolarity for use in humans, (4a) water for injection, (4b) sterile water, (5) water at a neutral pH, (6) water at an acidic pH, (7) water at a basic pH, (8) water at a given pH sub-range such as pH from about 1 to about 4, or from about 2 to about 3, on the acidic side, (9) water at a given pH sub-range such as pH from about 8 to about 12, from about 8 to about 10, or from about 8 to about 9, on the basic side, (10) water with a buffer added to maintain the pH of the water within a given pH range during extraction so long as the buffer does not detrimentally interfere with the extraction of sought soil constituents, (11) water with a co-solvent, (12) water with a miscible co-solvent, (12a) water in combination with (12b) a first water miscible solvent such that the combined solvents (water+first water miscible solvent) form a first liquid extraction co-solvent, (12c) a second water miscible solvent suitable for use in combination with water and the first water miscible solvent (water+the first water miscible solvent+second water miscible solvent) to form a second liquid extraction co-solvent, (13) water having a particular "hardness" or "softness" due to lime or certain calcium salts dissolved therein, (13a) hard water, (13b) soft water, (14) water that is physiologically acceptable and safe at a pH suitable for use with the compositions, formulations and intermediates described herein, and (15) any solvent, or co-solvent described herein with at a temperature, pH, pre-dissolved constituents, and/or low viscosity, adjusted to enhance the extraction power and/or to improve or facilitate the extraction of sought soil constituents from fossilized soils (FS) of interest.

The extraction of (FS) to recover its sought soil constituents (e.g., organic matter) may be conducted under certain extraction conditions using: (A) a solvent system with its above-noted characteristics (see items (1), (2), (3), (3a), (4), (4a), (4b), (5), (6), (7), (8), (9), (10), (11), (12), (12a), (12b), (12c), (13), (13a), (13b), (14) and/or (15) of the preceding paragraph) adjusted to facilitate extraction of the sought soil constituents from (FS), with (B) solvent volume (ml solvent per gram (FS)), (C) solvent flow rate (ml solvent per minute) or (ml per unit time), (D) solvent agitation (mixing rate, if any), (E) number of extraction cycles from n=1, 2, 3, ... N−2, N−1, N (where at first extraction cycle n=1 and at last repeated extraction cycle N=set upper limit), and/or (F) solvent purity.

The solvent system parameters (A) in conjunction with parameters (B), (C), (D), (E) and/or (F) are used and adjusted as needed to extract desirable soil constituents from (FS). Preferably, each parameter is selected to be sufficient to extract the sought organic matter, in the yields sought, preferably at lower cost, lower extraction cycles, greater efficiency with less time required. Such solvent system parameters may be adjusted to whatever solvent(s) may be ultimately used (including water as a sole extraction solvent or as a co-solvent with one or more water miscible co-solvents) so as to be sufficient (alone or in combination) to extract the sought-after constituents, particularly saccharides, of one or more of the compositions, formulations and/or intermediates described herein.

Treatment to Ensure Requisite Safety of Compositional Embodiments for Human Ingestion, Handling or Topical Use on Human Skin Sought-after organic matter obtained from soil samples must be demonstrated to be safe or recognized as safe for human ingestion, human handling, and/or topical application on human skin by the time the compositional embodiments are ultimately formed. The same can be said with respect to the various formulations made from one or more compositional embodiments or one or more intermediates thereof. To convert potentially unsafe organic matter obtained from untreated soil into a safe and still useful form, such organic matter can be sterilized to provide safe forms of same. However, untreated soils contain (or typically contain) a variety of pathogenic agents such as bacteria, bacterial waste products, fungi, yeast, viral contaminants, other microbial life and their waste products, and/or other known and unknown agents liable to cause illness, fever, and/or other undesirable consequences if ingested (or handled). To ensure safety, organic matter separated from untreated soil should be treated to provide pathogen-free (or nearly pathogen free) organic matter safe for human ingestion, handling and/or topical application. In other words, the treatment should be sufficient to render the organic matter safe for human ingestion, handling and/or topical application without destroying the sought organic matter (or without altering it beyond an acceptable level).

It is important to convert pathogenic agents that may be present in the untreated soil or organic matter into non-pathogenic forms or reduced to a non-pathogenic level safe for human ingestion, handling and/or topical application. Accordingly, the untreated soil and/or the soil organic matter should (a) be converted to a sterilized form or (b) sterilized in some fashion sufficient for safe use by humans (e.g., either for ingestion, handling and/or topical application). The organic matter obtained from the soils may contain N-acetylglucosamine (NAG) in varying amounts within ranges as specified herein. Certain compositional embodiments may also contain one or more other ingredients or other components as described herein.

In view of consideration(s) regarding safety due to the fact that "soil" naturally contains microflora and microfauna together with other microbes that may be unsafe if left untreated, it is prudent to treat "soils" or products, or intermediates derived from them to render them safe. Accordingly, proper implementation of testing protocols and procedures to adequately treat and test the "soil" samples and "soil derived products" (described herein) should be put in place. Also, by doing so, undesirable and potentially dangerous health consequences can be avoided. By doing so, the compositions, formulations and/or intermediates described herein can be ensured to be safe for use in humans and/or animals (e.g., cat, dog, horse, or other household pet or animal, etc.). As such, any concern as to health hazards upon ingestion, handling and/or topical application can be appropriately addressed and removed. Thus, to ensure the safety of the relevant compositional embodiment(s) (also denoted as "composition(s)" or "compositions" within this application), formulational embodiment(s) (also denoted as "formulation(s)" or "formulations" within this application), intermediate embodiment(s) (also denoted as "intermediate(s)" or "intermediates" within this application), and/or in other "products" as described herein may require sufficient sterilization together with sufficient testing to ensure safety for use in humans and/or animals.

Thus, the use of aseptic technique, proper equipment and procedures, and sufficient training of personnel should be followed in connection with embodiments of the claimed invention if the contemplated embodiment would represent a health hazard. In some instances, the sterilization should be a process that ensures safety that is combined with appropriate sterile packaging, while taking care not to defeat the desirable use of the composition, formulation, intermediate, product and/or processing involved. Some techniques may require sterilization via passing through a 0.22 micron ($\mu$m) filter to remove microbial and other health contaminants such as viruses and/or bacteria. Additionally, aseptic technique and processing should be used and applied by a qualified technician to maintain safety. If, for example, a particular contaminant is detected, then that contaminant needs to be removed or its associated hazard needs to be properly, safely and adequately nullified.

Accordingly, proper aseptic procedures, quality control measures and safety checks may need to be updated, implemented and followed by qualified personnel as needed to ensure the requisite safety. To do so, one could hire outside experts to assist in implementing and complying with necessary safety and quality measures or one could set up the same in-house. Also, appropriate equipment, packaging, execution, manufacturing considerations, manufacturing processes, design, and/or other relevant considerations may be needed.

With respect to safety and quality control testing, samples will need to be prepared and tested to confirm safety as applicable to "soil" derived materials, FS-CNs, N-FS-CNs, FS, etc., used with equipment coming in contact with the compositions, formulations, intermediates and/or products described herein. Considerations regarding handling, processing, and/or adding, plant materials, plant derived materials, organic or non-organic matter, etc. derived from the "soils" noted herein may require following certain safety testing as needed (e.g., procedures relating to preparation of test sample, testing equipment and reagents, aseptic technique, testing protocols, testing standards, testing measurements, record keeping of lot numbers, etc.) to ensure that safe product(s) are provided.

An example of a product suitable for use in connection with the claimed invention, or embodiments thereof, may be a composition denoted herein as "sterile fossilized soil organic matter" (SFSOM), optionally containing one or more of certain monosaccharides (MS), certain amino acids (AA), certain elements and minerals (MINs), certain oligosaccharides (OS), certain antioxidants (AO), and certain acids (e.g., fulvic acid (FA), humic acid (HA) and/or humifulvic acid (HFA) together with certain additional ingredient(s) (as described herein) in a number of possible combinations and/or permutations thereof (as described herein).

Sterile Profiles

In accordance with one non-limiting embodiment amongst others, the above-noted (SFSOM) composition(s), formulation(s), intermediate(s), and/or product(s) is/are provided in sufficiently sterile form to satisfy selected sterile profiles as defined by the Association of Analytical Communities International (AOAC). In testing the sterility of the composition(s), formulation(s), intermediate(s), and/or product(s), 3M Petrifilm™ Plates and Plate Reader may be used (available from 3M Microbiology, St. Paul, Minn.) as described below.

Petrifilm™ Plate testing methods are recognized as AOAC International's Official Methods of Analysis.$^{SM}$ These testing methods can be used to determine product compliance, and may be used with various embodiments of the invention as defined in later sections.

In that manner, one of ordinary skill in the art can determine whether the first, second, third and/or fourth sterile profiles have been satisfied. The first, second, third, and fourth sterile profiles are summarized below:

The first sterile profile is satisfied when pursuant to the protocol (AOAC) 990.12, less than 100 Petrifilm™ aerobic colonies are found per gram of (SFSOM).

The second sterile profile is satisfied when pursuant to the protocol (AOAC) 991.14, less than 100 petrifilm coliform colonies are found per gram of (SFSOM).

The third sterile profile is satisfied when pursuant to FDA-BAM $7^{th}$ Edition less than 10 yeast colonies are found per gram of (SFSOM).

The fourth sterile profile is satisfied when pursuant to FDA-BAM $7^{th}$ Edition less than 10 mold colonies are found per gram of (SFSOM).

With respect to (AOAC) 990.12 and (AOAC) 991.14, these procedures along with any references cited therein are incorporated herein by reference in their entirety. An alternative method for yeast and mold can be found at (AOAC) 997.02 which, along with any references cited therein, is incorporated herein by reference in its entirety.

The useful variety of Petrifilm™ Plates available include: aerobic count, coliform count, E. coli/coliform count, enterobacteriaceae count, environmental listeria, high-sensitivity coliform count, rapid coliform count, staph express count, and yeast and mold count. Other suitable microbial or pathogen detection methods can be employed.

The above-mentioned plates may be "read" to determine the number of colonies formed pursuant to the (AOAC) procedures and policies set by that body. Using the 3M Petrifilm™ Plate Reader, one can automate colony plates counts. The reader is further coupled with software that allows for storage of data for audit purposes or compliance with FDA 21 CFR Part 11 compliance and the retention of actual color images of plates that can be stored for further interpretation.

In accordance with an embodiment, the above-noted (SFSOM) composition(s), formulation(s), intermediate(s), and/or product(s) is/are provided in sufficiently sterile form to satisfy a first sterile profile (i) of <100 cfu/gram (SFSOM) of a Petrifilm™ Aerobic Plate count.

The equipment and apparatus used in connection with AOAC 990.12 are as described herein and/or in connection with AOAC 990.12. The reagents used in connection with AOAC 990.12 are as described herein and/or in connection with AOAC 990.12. The test sample preparation procedure is followed to prepare the test sample according to procedures noted in AOAC 990.12 and then tested for determining if the above-noted first sterile profile is satisfied.

The first sterile profile is satisfied if the Petrifilm™ Aerobic Plate count (APC) is less than 100 counts per gram of (SFSOM) (i.e., <100 cfu/gram (SFSOM) of a Petrifilm™ Aerobic Plate count) determined according to AOAC 990.12. The prepared test sample is tested to determine if the above-noted first sterile profile is satisfied.

In accordance with an embodiment, the above-noted (SFSOM) composition(s), formulation(s), intermediate(s), and/or product(s) is/are provided in sufficiently sterile form to satisfy a second sterile profile (ii) of <10 cfu/gram (SFSOM) of a Petrifilm™ Coliform Plate count.

The equipment and apparatus used in connection with AOAC 991.14 is specified in AOAC 991.14. The reagents used in connection with AOAC 991.14 are specified in AOAC 991.14. The entirety of AOAC 991.14, including all sub-references included or cited therein, is incorporated herein by reference. The test sample preparation procedure is followed to prepare the test sample according to procedures noted in AOAC 991.14 and then tested for determining if the second sterile profile is satisfied.

The second sterile profile is satisfied if the Petrifilm™ Coliform Plate count is less than 10 cfu per gram of (SFSOM) (i.e., <10/gram (SFSOM) of a Petrifilm™ Coliform Plate count) determined according to AOAC 991.14. The test sample is prepared to determine if the second sterile profile is satisfied.

In accordance with an embodiment, the above-noted (SFSOM) composition(s), formulation(s), intermediate(s), and/or product(s) is/are provided in sufficiently sterile form to satisfy a third sterile profile (iii) of <10 cfu/gram (SFSOM) of a Petrifilm™ Yeast Plate count.

The equipment and apparatus used in connection with FDA-BAM, $7^{th}$ Edition or FDA-BAM, $8^{th}$ Edition. The reagents used in connection with FDA-BAM $7^{th}$ Edition and FDA-BAM $8^{th}$ Edition are specified in the documents associated with FDA-BAM $7^{th}$ Edition and FDA-BAM $8^{th}$ Edition. The test sample preparation procedure followed to prepare the test sample is according to procedures noted in FDA-BAM $7^{th}$ Edition and/or FDA-BAM, $8^{th}$ Edition. The testing procedure is likewise specified in FDA-BAM $7^{th}$ Edition and/or FDA-BAM, $8^{th}$ Edition. The entirety of each of FDA-BAM, $7^{th}$ Edition and FDA-BAM, $8^{th}$ Edition are incorporated herein by reference in their entirety including any and all sub-references included or cited therein (which are also incorporated herein by reference in their entirety).

The third sterile profile (iii) is satisfied if the yeast count is less than 10 cfu per gram of (SFSOM) (i.e., <10/gram (SFSOM) of yeast) determined according to FDA-BAM 7th Edition or FDA-BAM, $8^{th}$ Edition. The prepared test sample is tested to determine if the above-noted third sterile profile is satisfied.

In accordance with an embodiment, the above-noted (SFSOM) composition(s), formulation(s), intermediate(s), and/or product(s) is/are provided in sufficiently sterile form to satisfy a fourth sterile profile (iv) of <10 cfu/gram (SFSOM) of a Petrifilm™ Mold Plate count.

The equipment and apparatus used in connection with FDA-BAM, $7^{th}$ Edition or FDA-BAM, $8^{th}$ Edition is/are specified therein. The reagents used in connection with FDA-BAM, $7^{th}$ Edition or FDA-BAM, $8^{th}$ Edition is/are specified therein.

The fourth sterile profile is satisfied if the mold count is less than 10 per gram of (SFSOM) (i.e., <10 cfu/gram (SFSOM) of mold) determined according to FDA-BAM $7^{th}$ Edition or FDA-BAM, $8^{th}$ Edition. The test sample preparation procedure to be followed to prepare the test sample according is provided in FDA-BAM, $7^{th}$ Edition or FDA-BAM, $8^{th}$ Edition. The prepared test sample is tested to determine if the above-noted fourth sterile profile is satisfied.

Pursuant to one or more process embodiments, one or more of the foregoing compositional embodiment(s), formulation(s) and/or intermediate(s) may be made by the inclusion (or addition) of certain organic matter obtained (e.g., collected, separated, harvested, extracted and/or isolated) from select soils (e.g., soils which may be rich in plant matter, plant breakdown products and/or plant breakdown byproducts together with or without other soil constituents). The organic matter so obtained from these soils may be converted into other more suitable forms useful for the production of one or more of the aforementioned formulation(s), compositional embodiment(s) and/or intermediate(s). Isolating selected organic matter from certain soils (e.g., soils which may be rich in plant matter, plant breakdown products and/or plant breakdown byproducts) may be accomplished by various separation techniques including extraction.

One embodiment of the presently claimed invention is a composition comprising sterile fossilized soil organic matter (SFSOM). Another embodiment of the presently claimed invention provides a method for preparing the sterile fossilized soil organic matter (SFSOM). Yet another embodiment relates to a process utilizing a reaction between (SFSOM) and a disaccharide source (e.g., sucrose). In particular, in accordance with one embodiment of the presently claimed invention, such embodiment provides a cost-effective and/or time-efficient method for preparing a composition containing one or more saccharides including mannose, xylose, arabinose, galactose, fucose, glucose, N-acetyl-neuraminic acid, N-acetylgalactosamine, and/or N-acetylglucosamine. Pursuant to one or more embodiments, these saccharides may each be provided in a concentration range from about 9 ppm to about 38,240 ppm, in one or more of the permutations of embodiments described in this application. Optionally, the total saccharide amounts may be no greater than about 71,200 ppm in a composition suitable for use with an embodiment of the claimed invention.

Often the saccharides listed may be chelated. Without being bound by theory, such chelation is believed to have maintained certain saccharides in fossilized soils (FS) possibly over 10 years (yrs), 20 yrs, 30 yrs, 40 yrs, 50 yrs, 60 yrs, 70 yrs, 80 yrs, 90 yrs, 100 yrs, or two or more centuries extending into thousands of years as may be commensurate with geological time frames sufficient to form fossilized soil (FS). The fossilization may be attributable to natural forces present on the earth in relation to past earthquakes, movement of tectonic plates, and/or the impingement of two continents plowing into each other. Pursuant to other embodiments, the herein described compositional embodiment(s) may optionally include one or more of the following: monosaccharides (MS), oligosaccharides (OS), amino acids (AA), trace elements and minerals (MIN), chelates (CHE), antioxidants (AO), humic acid (HA), fulvic acid (FA), and/or humifulvic acid (HFA). Without being bound by theory, we believe that the fossilized soil (FS) may contain chelated oligosaccharides (COS), chelated monosaccharides (CMS) and/or chelated amino acids (CAA). In that regard, without being bound by theory, it is believed that when fossilized soil (FS) is "drip" extracted with water, a dark liquid with an acidic pH from about 2.2 to about 3.5 (or from about 1.7 to about 2.9) may be collected. When the so-collected dark brown liquid extract (DBLE) is desiccated (i.e. dried to remove its liquids) under appropriate drying conditions including, but not limited to, air drying in the open, ambient air drying, flat bed drying, oven drying, or equivalent methods suitable for drying. A dark powder may be obtained denoted herein as Dry-DBLE-FN. When the so collected dark brown liquid extract (DBLE) is desiccated (i.e., liquids removed or dried), we are left with a soil designated herein as fossilized nutrition (FN) or as (Dry-DBLE-FN).

Such (FN) exhibits properties associated with chelation of minerals including, but not limited to, high conductivity and high molecular weight. Without being bound by theory, it is believed that a high iron (Fe) content in the (FN) may contribute to its high conductivity, its high molecular weight (on average) on the order from about 150,000 Daltons to about 250,000 Daltons and/or its high solids content. In view of the high (FN) molecular weight alone, the (FN) itself may be used as a nutrient or may be mixed with other suitable additives to form one or more of the formulations described herein. Without being bound by theory, it is believed that the chelates tend to bind to AA's, MINs, and/or other various sugars (monosaccharides (MS) and/or oligosaccharides (OS)) to improve their overall content in connection with the FN embodiments described herein.

Without being bound by theory, it is believed that some monosaccharides are chelated in the (FN) embodiments because the (FN) when subjected to high pressure liquid chromatography (HPLC) analysis does not reveal the presence of any saccharides until the (FN) is hydrolyzed with trifluoroacetic acid (TFA). During this (HPLC) analysis of FN's, it is believed that the saccharide peaks for the herein noted monosaccharides (MS) become readily visible upon addition of trifluoroacetic acid (TFA) presumably (though not being bound by theory) due to the TFA acting to release the monosaccharides (MS) from their chelation bonds into the HPLC gradient solution(s).

Particular composition(s), formulation(s), intermediate(s) and/or product(s) may include N-acetylglucosamine (NAG). Certain compositional embodiments may be formulations of (or additives in) one or more of foods, sweeteners, sugar substitutes, taste modifiers, vitamin supplements, nutritional supplements, dietary supplements, medicaments, homeopathic formulations, cosmetics and/or one or more additives thereof, respectively. Other compositional embodiments may include one or more intermediates suitable for the production of selected sweeteners, taste modifiers, sugar substitutes, nutritional supplements, dietary supplements, and/or cosmetics. Certain compositional embodiment(s) may be necessary intermediate(s) while others may be preferred intermediates used for the production of selected sweeteners, taste modifiers, sugar substitutes, nutritional supplements, dietary supplements, and/or cosmetics of interest.

In accordance with one aspect of the presently claimed invention, the fossilized soil (FS) material has a low pH (i.e., between about 1.0 and about 4.0), high molecular weight (i.e., from about 150,000 to about 250,000 Daltons) and/or an Oxygen Radical Absorption Capacity (ORAC) level of at least about 2,000 micromoles of Trolox equivalents per liter (μmol TE/L).

The (FS) material can contain, in chelated form, nine monosaccharides including mannose, xylose, arabinose, galactose, fucose, N-acetyl-neuraminic acid, glucose, N-acetylgalactosamine, and N-acetylglucosamine, each with a concentration ranging from about 9 parts per million (ppm) to about 38,240 ppm. In accordance with one embodiment of the presently claimed invention, the (FS) material suitably has a total monosaccharide content of about 67,500 ppm to about 74,800 ppm.

According to yet another embodiment, one or more of the above-mentioned formulation(s) includes N-acetylglucosamine in a concentration (i.e., mg N-acetylglucosamine to gram(s) of (SFSOM) composition) from about 0.05 mg/1.0 gm to about 100 mg/1.0 gm and values described therebetween.

According to yet another embodiment, one or more of the above-mentioned formulation(s) includes N-acetylglucosamine in a concentration (i.e., mg N-acetylglucosamine to gram(s) of (SFSOM) composition) from about 0.05 mg/1.0 gm to about 100 mg/1.0 gm, 0.10 mg/1.0 gm to about 90 mg/1.0 gm, from about 0.21 mg/1.0 gm to about 60 mg/1.0 gm, from about 0.22 mg/1.0 gm to about 50 mg/1.0 gm, from about 0.23 mg/1.0 gm to about 40 mg/1.0 gm, from about 0.24 mg/1.0 gm to about 30 mg/1.0 gm, from about 0.25 mg/1.0 gm to about 20 mg/1.0 gm, from about 0.26 mg/1.0 gm to about 10 mg/1.0 gm, from about 0.27 mg/1.0 gm to about 9 mg/1.0 gm, from about 0.28 mg/1.0 gm to about 8 mg/1.0 gm, from about 0.29 mg/1.0 gm to about 7 mg/1.0 gm, from about 0.3 mg/1.0 gm to about 6 mg/1.0 gm, from about 0.31 mg/1.0 gm to about 5 mg/1.0 gm, from about 0.32 mg/1.0 gm to about 4 mg/1.0 gm, from about 0.33 mg/1.0 gm to about 3 mg/1.0 gm, from about 0.34 mg/1.0 gm to about 2 mg/1.0 gm, from about 0.35 mg/1.0 gm to about 1 mg/1.0 gm, from about 0.15 mg/1.0 gm to about 1 mg/1.0 gm, from about 0.2 mg/1.0 gm to about 1 mg/1.0 gm, from about 0.21 mg/1.0 gm to about 0.9 mg/1.0 gm, from about 0.22 mg/1.0 gm to about 0.8 mg/1.0 gm, from about 0.23 mg/1.0 gm to about 0.7 mg/1.0 gm, from about 0.24 mg/1.0 gm to about 6 mg/1.0 gm, from about 0.25 mg/1.0 gm to about 0.5 mg/1.0 gm, and/or from about 0.26 mg/1.0 gm to about 0.4 mg/1.0 gm.

According to one or more other embodiments, each of the foregoing ranges of the (mg) of N-acetylglucosamine per (gm) of (SFSOM) is provided with the word "about" deleted therefrom. So, for example, the term "from about 0.2 mg/1.0 gm to about 1 mg/1.0 gm" is translated into three possible permutations including (1) "from 0.2 mg/1.0 gm to about 1 mg/1.0 gm" which reads as "from 0.2 mg/1.0 gm to about 1 mg/1.0 gm," (2) "from about 0.2 mg/1.0 gm to 1 mg/1.0 gm" which reads as "from about 0.2 mg/1.0 gm to 1 mg/1.0 gm," and (3) "from 0.2 mg/1.0 gm to 1 mg/1.0 gm" which reads as "from 0.2 mg/1.0 gm to 1 mg/1.0 gm" for each of the ranges listed in the immediately preceding paragraph. Thus, each entry in the preceding paragraph includes three additional permutations for each such entry without having to repeat each permutation—having provided a sufficiently detailed description of the same so as to be understood by a person having ordinary skill in the relevant art. Formulations in accordance with each of the above concentration ranges are included in this description.

According to further embodiments, each of the foregoing described formulations are further described to include one or more members of N-acetylneuraminic acid (NANA), N-acetylgalactosamine (NAGA), glucose (GLUC), fucose (FUC), galactose (GALC), arabinose (ARAB), xylose (XYL) and mannose (MANN) together with Amino Acid(s) (AA), Antioxidant(s) (AO), Mineral(s) (MIN), Monosaccharide(s) (MS) and Oligosaccharide(s) (OS) designated according to the parenthetical abbreviations noted.

Other embodiments of each of the above-noted formulations include the following permutations containing those combinations of members listed in TABLE 1, TABLE 1a, and TABLE 2 below with the entry designation "Y" indicating the presence of the member from the row and the column as listed and with the parenthetical abbreviations N-acetylneuraminic acid (NANA); N-acetylgalactosamine (NAGA); glucose (GLUC), fucose (FUC), galactose (GALC); arabinose (ARAB); xylose (XYL); mannose (MANN); Amino Acid(s) (AA), Antioxidant(s) (AO), Mineral(s) (MIN); Monosaccharide(s) (MS); oligosaccharide(s) (OS); and designations (Y)=present; and (OPT)=optionally present:

TABLE 1

|      | NANA | NAGA | GLUC | FUC | GALC | ARAB | XYL | MANN | AA  | AO  | MIN | OS  |
|------|------|------|------|-----|------|------|-----|------|-----|-----|-----|-----|
| NANA | Y    | Y    | Y    | Y   | Y    | Y    | Y   | Y    | Y   | Y   | Y   | Y   |
| NAGA |      | Y    | Y    | Y   | Y    | Y    | Y   | Y    | Y   | Y   | Y   | Y   |
| GLUC |      |      | Y    | Y   | Y    | Y    | Y   | Y    | Y   | Y   | Y   | Y   |
| FUC  |      |      |      | Y   | Y    | Y    | Y   | Y    | Y   | Y   | Y   | Y   |
| GALC |      |      |      |     | Y    | Y    | Y   | Y    | Y   | Y   | Y   | Y   |
| ARAB |      |      |      |     |      | Y    | Y   | Y    | Y   | Y   | Y   | Y   |
| XYL  |      |      |      |     |      |      | Y   | Y    | Y   | Y   | Y   | Y   |
| MANN |      |      |      |     |      |      |     | Y    | Y   | Y   | Y   | Y   |
| AA   |      |      |      |     |      |      |     |      | Y   | Y   | Y   | Y   |
| AA   | OPT  | OPT  | OPT  | OPT | OPT  | OPT  | OPT | OPT  | Y   | OPT | OPT | OPT |
| AO   | OPT  | OPT  | OPT  | OPT | OPT  | OPT  | OPT | OPT  | OPT | Y   | OPT | OPT |
| MIN  | OPT  | OPT  | OPT  | OPT | OPT  | OPT  | OPT | OPT  | OPT | OPT | Y   | OPT |
| OS   | OPT  | OPT  | OPT  | OPT | OPT  | OPT  | OPT | OPT  | OPT | OPT | OPT | Y   |

Other combinations may also include those specified in TABLE 1a below. Pursuant to TABLE 1a, the following combinations of sugars may be utilized in accordance with one or more embodiments of the presently claimed invention. For example, a aldose (Ald), a ketose (Ket), triose (Tri), a pentose (Pen), a hexose (Hex), an allose (All), an altrose (Alt), arabinose (Arab), erythrose (Ery), erythrulose (Er), fructose (Fm), galactose (Galc), glucose (Gluc), glyceraldehyde (Glc), gulose (Gul), lyxose (Lyx), idose (Ido), mannose (Mann), psicose (Psi), ribose (Rib), ribulose (Ril), sorbose (Sor), tagatose (Tag), threose (The), xylose (Xyl), sucrose (Suc) and/or combinations thereof may be utilized in connection with the embodiments of the presently claimed invention. See *Remington's*. Thus all possible permutations with the listed actives, monosaccharides, sugars, oligosaccharides, disaccharides, excipients, diluents, additives, lubricants, flow control agents, preservatives, flavorants, taste enhancers, preservatives, desiccants, immediate release aids, sustained release aids, enantiomers, diastereomers, racemic mixtures, polymorphs, carriers, inert ingredients, formulation aids, powders, liquids, ointments, gums, pastes, creams, solutions, emulsions, suspensions, disintegrants, pH control agents, buffering agents, isotonic agents, surfactants, amphiphilic agents, ionic agents, chelating agents, sequestrants, charcoal, all natural products, botanicals, extracts of botanicals and the like may be included in one or more non-limiting embodiments of the claimed invention.

Nutritional supplements, food grade products and related constituents are within the scope of the embodiments of the presently claimed or described invention(s).

TABLE 1a recites additional sugars and sweeteners that may be used in one or more combinations and/or permutations in connection with the embodiments of the presently claimed or described invention(s) of this paper.

Various permutations of amino acids (AA), anti-oxidants (AO), minerals (MIN), monosaccharides (MS), polysaccharides (PS), oligosaccharides (OS) may be used in connection with the embodiments of the presently claimed or described invention(s) of this paper. See for example TABLE 2 below.

TABLE 2

|       | (AA) | (AO) | (MIN) | (MS) | (PS) | (OS) |
|-------|------|------|-------|------|------|------|
| (AA)  | Y    | Y    | Y     | Y    | Y    | Y    |
| (AO)  |      | Y    | Y     | Y    | Y    | Y    |
| (MIN) |      |      | Y     | Y    | Y    | Y    |
| (MS)  |      |      |       | Y    | Y    | Y    |
| (PS)  |      |      |       |      | Y    | Y    |
| (OS)  |      |      |       |      |      | Y    |

Other compositional embodiments include the following combination of amino acids and minerals in TABLE 3, TABLE 4, TABLE 5, TABLE 6, TABLE 7 and TABLE 8 as noted below:

TABLE 1a

|     | Ald | Ket | Tri | Pen | Hex | All | Ery | Erl | Fru | Gly | Gul | Lyx | Ido | Psi | Rib | Ril | Sor | Tag | The |
|-----|-----|-----|-----|-----|-----|-----|-----|-----|-----|-----|-----|-----|-----|-----|-----|-----|-----|-----|-----|
| Ald | Y   | Y   | Y   | Y   | Y   | Y   | Y   | Y   | Y   | Y   | Y   | Y   | Y   | Y   | Y   | Y   | Y   | Y   | Y   |
| Ket |     | Y   | Y   | Y   | Y   | Y   | Y   | Y   | Y   | Y   | Y   | Y   | Y   | Y   | Y   | Y   | Y   | Y   | Y   |
| Tri |     |     | Y   | Y   | Y   | Y   | Y   | Y   | Y   | Y   | Y   | Y   | Y   | Y   | Y   | Y   | Y   | Y   | Y   |
| Pen |     |     |     | Y   | Y   | Y   | Y   | Y   | Y   | Y   | Y   | Y   | Y   | Y   | Y   | Y   | Y   | Y   | Y   |
| Hex |     |     |     |     | Y   | Y   | Y   | Y   | Y   | Y   | Y   | Y   | Y   | Y   | Y   | Y   | Y   | Y   | Y   |
| All |     |     |     |     |     | Y   | Y   | Y   | Y   | Y   | Y   | Y   | Y   | Y   | Y   | Y   | Y   | Y   | Y   |
| Ery |     |     |     |     |     |     | Y   | Y   | Y   | Y   | Y   | Y   | Y   | Y   | Y   | Y   | Y   | Y   | Y   |
| Erl |     |     |     |     |     |     |     | Y   | Y   | Y   | Y   | Y   | Y   | Y   | Y   | Y   | Y   | Y   | Y   |
| Fru |     |     |     |     |     |     |     |     | Y   | Y   | Y   | Y   | Y   | Y   | Y   | Y   | Y   | Y   | Y   |
| Gly |     |     |     |     |     |     |     |     |     | Y   | Y   | Y   | Y   | Y   | Y   | Y   | Y   | Y   | Y   |
| Gul |     |     |     |     |     |     |     |     |     |     | Y   | Y   | Y   | Y   | Y   | Y   | Y   | Y   | Y   |
| Lyx |     |     |     |     |     |     |     |     |     |     |     | Y   | Y   | Y   | Y   | Y   | Y   | Y   | Y   |
| Ido |     |     |     |     |     |     |     |     |     |     |     |     | Y   | Y   | Y   | Y   | Y   | Y   | Y   |
| Psi |     |     |     |     |     |     |     |     |     |     |     |     |     | Y   | Y   | Y   | Y   | Y   | Y   |
| Rib |     |     |     |     |     |     |     |     |     |     |     |     |     |     | Y   | Y   | Y   | Y   | Y   |
| Ril |     |     |     |     |     |     |     |     |     |     |     |     |     |     |     | Y   | Y   | Y   | Y   |
| Sor |     |     |     |     |     |     |     |     |     |     |     |     |     |     |     |     | Y   | Y   | Y   |
| Tag |     |     |     |     |     |     |     |     |     |     |     |     |     |     |     |     |     | Y   | Y   |
| The |     |     |     |     |     |     |     |     |     |     |     |     |     |     |     |     |     |     | Y   |

TABLE 3

| | Arg | His | Ile | Leu | Lys | Met | Phe | Ser | Thr | Trp | Val | Ala | Asp | Asg | Cys | Glu | Gly | Pro | Tyr |
|---|---|---|---|---|---|---|---|---|---|---|---|---|---|---|---|---|---|---|---|
| Arg | Y | Y | Y | Y | Y | Y | Y | Y | Y | Y | Y | Y | Y | Y | Y | Y | Y | Y | Y |
| His | | Y | Y | Y | Y | Y | Y | Y | Y | Y | Y | Y | Y | Y | Y | Y | Y | Y | Y |
| Ile | | | Y | Y | Y | Y | Y | Y | Y | Y | Y | Y | Y | Y | Y | Y | Y | Y | Y |
| Leu | | | | Y | Y | Y | Y | Y | Y | Y | Y | Y | Y | Y | Y | Y | Y | Y | Y |
| Lys | | | | | Y | Y | Y | Y | Y | Y | Y | Y | Y | Y | Y | Y | Y | Y | Y |
| Met | | | | | | Y | Y | Y | Y | Y | Y | Y | Y | Y | Y | Y | Y | Y | Y |
| Phe | | | | | | | Y | Y | Y | Y | Y | Y | Y | Y | Y | Y | Y | Y | Y |
| Ser | | | | | | | | Y | Y | Y | Y | Y | Y | Y | Y | Y | Y | Y | Y |
| Thr | | | | | | | | | Y | Y | Y | Y | Y | Y | Y | Y | Y | Y | Y |
| Trp | | | | | | | | | | Y | Y | Y | Y | Y | Y | Y | Y | Y | Y |
| Val | | | | | | | | | | | Y | Y | Y | Y | Y | Y | Y | Y | Y |
| Ala | | | | | | | | | | | | Y | Y | Y | Y | Y | Y | Y | Y |
| Asp | | | | | | | | | | | | | Y | Y | Y | Y | Y | Y | Y |
| Asg | | | | | | | | | | | | | | Y | Y | Y | Y | Y | Y |
| Cys | | | | | | | | | | | | | | | Y | Y | Y | Y | Y |
| Glu | | | | | | | | | | | | | | | | Y | Y | Y | Y |
| Gly | | | | | | | | | | | | | | | | | Y | Y | Y |
| Pro | | | | | | | | | | | | | | | | | | Y | Y |
| Tyr | | | | | | | | | | | | | | | | | | | Y |

The amino acids that may be included in any one of the foregoing compositional embodiments may be just the essential amino acids, just the amino acids containing sulfur, just the amino acids that can be phosphorylated, just the polar (hydrophilic) amino acids, just the non-polar (hydrophobic) amino acids, just the negatively charged amino acids, just the positively charged amino acids, just the charged amino acids include Lys, Arg and His. The sulfur containing amino acids include Met and Cys. The foregoing amino acids may be added from within the discrete groups (polar, non-polar, charged, positively charged, negatively charged, those that can be phosphorylated, or those that can be chelated, as non-overlapping groups or these groups may be combined in the following fashion noted in TABLE 3a, below:

TABLE 3a

| | Polar Amino Acid | Non-Polar Amino Acid | Charged Amino Acid | Positively Charged Amino Acid | Negatively Charged Amino Acid | Phosphorylated Amino Acid | Sulfur Containing Amino Acid |
|---|---|---|---|---|---|---|---|
| Polar Amino Acid | Y | Y | Y | Y | Y | Y | Y |
| Non-Polar Amino Acid | | Y | Y | Y | Y | Y | Y |
| Charged Amino Acid | | | Y | Y | Y | Y | Y |
| Positively Charged Amino Acid | | | | Y | Y | Y | Y |
| Negatively Charged Amino Acid | | | | | Y | Y | Y |
| Phosphorylated Amino Acid | | | | | | Y | Y |
| Sulfur Containing Amino Acid | | | | | | | Y | and/or chelates of any of the above amino acids to the extent they may be chelated without detrimentally interfering with the utility of the (SFSOM) as intended to be used where the detrimental interference prevents or largely prevents the use as intended (e.g., whether as a food, a nutritional supplement, a medicament, a vitamin supplement, a cosmetic, a dermatological formulation, and/or an additive thereof).

The essential amino acids include the following: Ile, Leu, Lys, Met, Phe, Thr, Trp, and Val. The non-essential amino acids include the following: Arg, Ala, Asn, Asp, Cys, Gln, Glu, Gly, Pro, Ser, and Tyr. The amino acids that are non-polar (hydrophobic) include: Gly, Ala, Val, Leu, Ile, Met, Phe, Trp, and Pro. The amino acids that are polar (hydrophilic) include: Ser, Thr, Cys, Tyr, Asn and Gln. The positively charged amino acids include Asp and Glu. The negatively charged amino Optionally, an amino acid may be provided in a chelated form. Optionally, an amino acid from the Phosphorylated Amino Acid category may be presented in its non-phosphorylated form. Optionally, the charged amino acids may be presented in chelated form. Optionally, the chelating agent is one that is safe for use for human ingestion if included in a formulation intended to be ingested. Optionally, the chelating agent is one that is safe for topical application on a human if used in the topical formulation as intended.

According to other compositional embodiments, the above-noted formulations may further contain the following permutations of minerals or elements as noted in TABLE 4, TABLE 5, TABLE 6, and TABLE 7 below with Y=(present in the compositional embodiment), and with OPT=(presence is optional in a given compositional embodiment):

TABLE 4

| | Al | Sb | As | Ba | Be | Bi | B | Br | Ca | C | Ce | Cs | Cl | Cr | Co | Cu |
|---|---|---|---|---|---|---|---|---|---|---|---|---|---|---|---|---|
| Al | Y | Y | OPT | Y | OPT | Y | Y | Y | Y | Y | OPT | OPT | Y | Y | Y | Y |
| Sb | | Y | OPT | Y | OPT | Y | Y | Y | Y | Y | OPT | OPT | Y | Y | Y | Y |
| As | | | OPT | Y | OPT | Y | Y | Y | Y | Y | OPT | OPT | Y | Y | Y | Y |
| Ba | | | | Y | OPT | Y | Y | Y | Y | Y | OPT | OPT | Y | Y | Y | Y |
| Be | | | | | OPT | Y | Y | Y | Y | Y | OPT | OPT | Y | Y | Y | Y |
| Bi | | | | | | Y | Y | Y | Y | Y | OPT | OPT | Y | Y | Y | Y |
| B | | | | | | | Y | Y | Y | Y | OPT | OPT | Y | Y | Y | Y |
| Br | | | | | | | | Y | Y | Y | OPT | OPT | Y | Y | Y | Y |
| Ca | | | | | | | | | Y | Y | OPT | OPT | Y | Y | Y | Y |
| C | | | | | | | | | | Y | OPT | OPT | Y | Y | Y | Y |
| Ce | | | | | | | | | | | OPT | OPT | Y | Y | Y | Y |
| Cs | | | | | | | | | | | | OPT | Y | Y | Y | Y |
| Cl | | | | | | | | | | | | | Y | Y | Y | Y |
| Cr | | | | | | | | | | | | | | Y | Y | Y |
| Co | | | | | | | | | | | | | | | Y | Y |
| Cu | | | | | | | | | | | | | | | | Y |

TABLE 5

| | Dy | Er | F | Gd | Ga | Ge | Hf | Ho | In | Fe | La | Li | Lu | Mg | Mn | Nd |
|---|---|---|---|---|---|---|---|---|---|---|---|---|---|---|---|---|
| Dy | OPT | OPT | Y | OPT | OPT | OPT | OPT | OPT | OPT | Y | OPT | Y | OPT | Y | OPT | Y |
| Er | | Y | Y | OPT | OPT | OPT | OPT | OPT | OPT | Y | OPT | Y | OPT | Y | OPT | Y |
| F | | | Y | OPT | OPT | OPT | OPT | OPT | OPT | Y | OPT | Y | OPT | Y | OPT | Y |
| Gd | | | | OPT | OPT | OPT | OPT | OPT | OPT | Y | OPT | Y | OPT | Y | OPT | Y |
| Ga | | | | | OPT | OPT | OPT | OPT | OPT | Y | OPT | Y | OPT | Y | OPT | Y |
| Ge | | | | | | OPT | OPT | OPT | OPT | Y | OPT | Y | OPT | Y | OPT | Y |
| Hf | | | | | | | OPT | OPT | OPT | Y | OPT | Y | OPT | Y | OPT | Y |
| Ho | | | | | | | | OPT | OPT | Y | OPT | Y | OPT | Y | OPT | Y |
| In | | | | | | | | | OPT | Y | OPT | Y | OPT | Y | OPT | Y |
| Fe | | | | | | | | | | Y | OPT | Y | OPT | Y | OPT | Y |
| La | | | | | | | | | | | OPT | Y | OPT | Y | OPT | Y |
| Li | | | | | | | | | | | | Y | OPT | Y | OPT | Y |
| Lu | | | | | | | | | | | | | OPT | Y | OPT | Y |
| Mg | | | | | | | | | | | | | | Y | OPT | Y |
| Mn | | | | | | | | | | | | | | | OPT | Y |
| Nd | | | | | | | | | | | | | | | | Y |

TABLE 6

| | Ni | Os | P | K | Pr | Re | Rb | Ru | Sm | Sc | Se | Si | Ag | Na | Sr | S |
|---|---|---|---|---|---|---|---|---|---|---|---|---|---|---|---|---|
| Ni | OPT | OPT | Y | Y | OPT | OPT | OPT | OPT | OPT | OPT | Y | Y | Y | Y | OPT | Y |
| Os | | OPT | Y | Y | OPT | OPT | OPT | OPT | OPT | OPT | Y | Y | Y | Y | OPT | Y |
| P | | | Y | Y | OPT | OPT | OPT | OPT | OPT | OPT | Y | Y | Y | Y | OPT | Y |
| K, | | | | Y | OPT | OPT | OPT | OPT | OPT | OPT | Y | Y | Y | Y | OPT | Y |
| Pr | | | | | OPT | OPT | OPT | OPT | OPT | OPT | Y | Y | Y | Y | OPT | Y |
| Re | | | | | | OPT | OPT | OPT | OPT | OPT | Y | Y | Y | Y | OPT | Y |
| Rb | | | | | | | OPT | OPT | OPT | OPT | Y | Y | Y | Y | OPT | Y |
| Ru | | | | | | | | OPT | OPT | OPT | Y | Y | Y | Y | OPT | Y |
| Sm | | | | | | | | | OPT | OPT | Y | Y | Y | Y | OPT | Y |
| Sc | | | | | | | | | | OPT | Y | Y | Y | Y | OPT | Y |
| Se | | | | | | | | | | | Y | Y | Y | Y | OPT | Y |
| Si | | | | | | | | | | | | Y | Y | Y | OPT | Y |
| Ag | | | | | | | | | | | | | Y | Y | OPT | Y |
| Na | | | | | | | | | | | | | | Y | OPT | Y |
| Sr | | | | | | | | | | | | | | | OPT | Y |
| S | | | | | | | | | | | | | | | | Y |

TABLE 7

| | Te | Tb | Tl | Th | Tm | Sn | Ti | V | Yb | Y | Zn | Zr |
|---|---|---|---|---|---|---|---|---|---|---|---|---|
| Te | OPT | OPT | OPT | OPT | OPT | OPT | Y | Y | OPT | OPT | Y | OPT |
| Tb | | OPT | OPT | OPT | OPT | OPT | Y | Y | OPT | OPT | Y | OPT |
| Tl | | | OPT | OPT | OPT | OPT | Y | Y | OPT | OPT | Y | OPT |
| Th | | | | OPT | OPT | OPT | Y | Y | OPT | OPT | Y | OPT |
| Tm | | | | | OPT | OPT | Y | Y | OPT | OPT | Y | OPT |
| Sn | | | | | | OPT | Y | Y | OPT | OPT | Y | OPT |
| Ti | | | | | | | Y | Y | OPT | OPT | Y | OPT |
| V | | | | | | | | Y | OPT | OPT | Y | OPT |

TABLE 7-continued

| | Te | Tb | Tl | Th | Tm | Sn | Ti | V | Yb | Y | Zn | Zr |
|---|---|---|---|---|---|---|---|---|---|---|---|---|
| Yb | | | | | | | | | | OPT | Y | OPT |
| Y | | | | | | | | | | OPT | Y | OPT |
| Zn | | | | | | | | | | | Y | OPT |
| Zr | | | | | | | | | | | | OPT |

Other combinations of various elements, trace metals and/or trace minerals may be optionally included in any one of the compositional embodiments described herein taken from one or more of the following categories either as discrete categories or as some combination thereof. The discrete categories are as follows: alkali metals (Li, Na, K, Rb, Cs, Fr; however, Cs and Fr should be avoided to the extent that their inherent instability poses a problem or medical risk); alkaline earth metals (Be, Mg, Ca, Sr, Ba and Ra); however, if any of the elements from this category should be avoided or present only in or below certain amounts, they should be adjusted to safe levels, as needed to be considered safe for human ingestion, safe for human handling and/or safe for topical application on a human, respectively, and by respective amounts.

According to other non-limiting embodiments, none or more of the amino acids (AAs) listed herein may be chemically modified or may be chemical analogs of the listed amino acids (AAs) containing one or more methylated (—CH$_3$) groups bonded or attached to the amino group (—NH$_2$), the α-carbon (i.e., in an AA of formula H$_2$N—CHR—COOH the middle —CHR-carbon being the α-carbon), the R-side chain (i.e., the R-side chain bonded or connected to the α-carbon), to the carboxylic acid group (—COOH) and/or combinations thereof (e.g., as permitted under permissible chemical stoichiometric rules and its variations including, but not limited to, a nitrogen atom having no more than 3-4 covalent bonds per N atom, and/or a carbon atom having no more than 4 covalent bonds per C atom; and/or which may include permissible variations of the same such as tautomers or other chemically viable forms thereof permitted under applicable rules of chemical bonding taking into consideration the bonds that a N atom can reasonably form and/or the bonds a C atom can reasonably form). Additionally, such methylated groups (—CH$_3$) may themselves be substituted with methyl donors (e.g., electron donating groups) suitable for inclusion in foods, nutrients, beverages, and other edible products that are in a form safe for human consumption (e.g., as may be considered safe for human consumption as determined by the Food and Drug Administration (FDA), etc.) and not unsafe for human consumption in the recommended amounts ingested, for example.

Pursuant to one or more non-limiting embodiments, antioxidants (AOs) may also be included in various foods, beverages, nutrients and any other forms described herein. The AOs may have an ORAC value of ≧about 100 μmol (TE/L), ≧100 μmol (TE/L), ≧about 200 μmol (TE/L), ≧200 μmol (TE/L), ≧about 250 μmol (TE/L), ≧250 μmol (TE/L), ≧about 275 μmol (TE/L), ≧about 275 μmol (TE/L), ≧275 μmol (TE/L), ≧about 300 μmol (TE/L), and ≧300 mmol (TE/L). Such AOs may include superoxide dismutase or may not exclude the presence of superoxide dismutase (SOD).

In accordance with one or more non-limiting embodiments, the nutritive value of one or more formulations described herein may be augmented, increased, and/or supplemented with further added (and/or in situ formed) constituents not otherwise available without such further added (and/or in situ formed) constituents. For example, certain vitamins (e.g., fat soluble vitamins, water-soluble vitamins, none or one or more of vitamins (including, but not limited to, vitamins A, B, B-complex, B1, B2, B6, B9, B12, C, D, E, etc.), proteins (e.g., protein from egg whites, protein from egg yolk, proteins from animal sources, proteins from vegetable sources, proteins from animal sources only, proteins from vegetable sources only, etc.) may be provided/added as additional constituents. Additional nutritive constituents may be added and/or may be formed in addition to in situ formed constituents—if any constituents are so formed in situ. To be clear, while in situ formed constituents may be so formed, it is not necessary that any in situ formed constituents are so formed pursuant to one or embodiments of the formulations described herein.

Examples of other constituents that may be added include food grade additives suitable for human consumption in amounts suitable for safe human consumption. For example, a food grade color, a food grade pigment and/or a food grade dye (or one or more of such color, pigment and/or dye, respectively) may be added to none or one or more of the formulations described herein pursuant to other non-limiting embodiments of the same, respectively.

Pursuant to one or more embodiments of formulations, compositions, intermediates, and/or products described herein, one or more of the foregoing may be formed into sweeteners, taste enhancers, taste modifiers, table sugar substitutes, sweetness enhancers, etc. that may utilize and/or contain and/or in situ form one or more disaccharides, sucrose, and/or raw ingredient sources of the same. Examples of such formulations include, but are not limited to, Formulation I, Formulation II, and/or combinations thereof. Such non-limiting embodiments as described herein may have the same (or nearly the same or nearly the same within publicly acceptable bounds—acceptable to a sub-group of the public such as to at least 10%, at least 20%, at least 30%, at least 40%, at least 50%, at least 60%, at least 70%, at least 80%, at least 90% or more of a given population of the public or a given sub-population the public, respectively) look, and/or feel and/or use (or substantially so) as that of table sugar with a specific nutritive value that may be (or is) similar to that of oligosaccharides, monosaccharides, amino acids, trace minerals, antioxidants, methyl donating groups (MDGs) and/or combinations and/or sub-combinations thereof, respectively.

Various other embodiments of one or more of any of the formulations, compositions, intermediates, products, sweeteners, and the like described herein may have or exhibit a specific glycemic index (GI) value in the range of about 65 or less, about 60 or less, about 55 or less, about 53 or less, about 50 or less, about 45 or less, about 40 or less, about 35 or less, about 30 or less, about 20 or less, about 15 or less, about 10 or less or 65 or less, 60 or less, 55 or less, 53 or less, 50 or less, 45 or less, 40 or less, 35 or less, 30 or less, 20 or less, 15 or less, 10 or less, etc.

Other non-limiting embodiments of formulations described herein may have suitable ranges of GI values including, but not limited to, from about 15 to about 65, from about 15 to about 60, from about 15 to about 55, from about 20 to about 65, from about 25 to about 65, from about 30 to about 65, from about 35 to about 65, from about 35 to about 60, from about 40 to about 60, from about 45 to about 60, from about 45 to about 55, from about 30 to about 60, from about 35 to about 55, from 15-65, from 15-60, from 15-55, from 20-65, from 25-65, from 30-65, from 35-65, from 35-60, from 40-60, from 45-60, from 45-55, from 30-60, from 35-55, for example.

In accordance with other non-limiting embodiments, one or more embodiments of the formulations, Formulation I, Formulation II, a combination of Formulation I with Formulation II, compositions, intermediates, and/or products may exhibit glycemic index values (GI values) in the range from about 15 to about 53, from about 20 to about 50, from about 25 to about 45, from about 30 to about 40, from about 35 to about 40, from 15-50, from 20-50, from 25-45, from 30-40, and from 35-40, respectively, including (but not limited to) those range(s) of GI values from each of any one of the above noted GI value ranges specified or described herein (in this application) or specified or described in any one of the preceding paragraphs or in any of the later paragraphs of this application, respectively.

Other suitable GI value ranges for Formulation I, Formulation II or combinations thereof may fall in the range of GI values from about 35 to about 55, from about 35 to about 60, from about 35 to about 65, from 35-55, from 35-60, and from 35-65, respectively.

One or more embodiments of Formulation I (Formula I) or Formulation II (Formula II) or a combination thereof (Formulation I and Formulation II combined in desired amounts or weight ratios) may mimic the appearance of table sugar with similar consistency, color, flow characteristics, hygroscopic nature, solubility in water, solubility in hot water (e.g., 30-50° C. or more), solubility in cold water (e.g., 1-20° C.; 2-20° C.; 5-20° C.; 10-20° C.; 10-15° C.; and 12-15° C.) and solubility in any other liquid suitable for human consumption and/or any combinations or sub-combinations thereof, respectively.

Pursuant to one or more non-limiting embodiments, a sweetener of Formulation I, Formulation II or a combination thereof either as a liquid, a solid (e.g., crystalline form, amorphous form, powder form, granular form, or any commercially suitable form for dispensing in sealed packets, sealed packages, as loose bulk powder form, in bottled form, in bottled form with dispensing droppers or dispensing holes, shakers much like sugar or salt shakers, etc. may be provided. If in liquid form, a dropper dispensing bottle may be preferred. Other non-limiting dispensing forms or containers with the sweetener formulations described herein (or with any formulations described herein) may be provided such that the dispensing containers or dispensing forms are suitable for a liquid or solid form of the sweetener formulation held in the dispensing container suited for same.

According to one or more embodiments, the sweetener of Formulation I, Formulation II or a combination thereof may be added as a constituent of food as a taste modifier, as a constituent of a beverage, a tea, a coffee, a juice, a concentrate, a nutritional supplement, a desert, a baked good, a bread, a dough, an enhanced sugar (e.g., sucrose plus Formulation I, plus Formulation II or plus Formulation I with Formulation II). Other suitable forms of Formulation I, Formulation II or combinations thereof are contemplated and are encompassed within embodiments of the same as would be understood by a person having ordinary skill in the art when taken in conjunction with this disclosure.

Sweeteners of Formulation I, Formulation II or any combination thereof may be a taste modifier, a sweetener, a sugar substitute, a co-sweetener with sugar/table sugar. Such non-limiting embodiments of Formulation I, Formulation II or combinations thereof may be used with or without sugar in foods including all commercial uses of the same where sugar alone and/or other sweeteners may be used. Example include, but are not limited to, baked goods, cakes, breads, beverages, carbonated beverages, non-carbonated beverages, teas, coffees, powdered milk products (e.g., Cremora™) powdered creamers, liquid creams, dairy products, flavorants, energy drinks, nutritional supplements, pharmaceutical products, cough syrups, lozenges, candies, tablets, capsules, suspensions, solutions, over the counter (OTC) products for adults, OTC products for teenagers, OTC products for children, OTC products for toddlers, OTC products for infants, products for diabetics, products for Type I diabetics (insulin dependent), products for Type II diabetics (adult onset), products for those on limited sugar and/or low-carbohydrate diets, or any person or persons in need thereof, respectively.

The embodiments of Formulation I, Formulation II or combinations thereof may have or provide a sweetener with a GI value range in accordance with one or more of the ranges described in this application.

In connection a disaccharide such as sucrose that may be used, such disaccharide may include fructose and glucose optionally at a 50:50 (w/w) ratio. According to another embodiment a source of xylose and/or glucose found in Raw Arabica may be used. Pursuant to another embodiment, (SF-SOM) made with a disaccharide (e.g., sucrose, or a source of fructose and glucose at a 50:50 (w/w) ratio) and/or Raw Arabica (e.g., or a source of xylose and/or glucose) may have an Oxygen Radical Absorbance Capacity (ORAC) of about 2,320 in micromole Trolox equivalent per liter units (μmol TE/L). See U.S. Pat. No. 7,132,296 and references cited therein.

In accordance with one aspect of the presently claimed invention, the fossilized soil (FS) material may have a pH from about 1.0 to about 4.0, high molecular weight from about 150,000 Daltons to about 250,000 Daltons and/or an Oxygen Radical Absorption Capacity (ORAC) level of at least about 2,000 micromoles of Trolox equivalents per liter (μmol TE/L).

Further, the (FS) material has been found to include 18 amino acids which are also believed to be present in chelated form. The amino acid profile of a typical sample of the (FS) material is shown in TABLE 8, below. Amino acids present in the (FS) material include arginine, histidine, isoleucine, leucine, lysine, methionine, phenylalanine, serine, threonine, tryptophan, valine, alanine, aspartic acid/asparagine, cysteine, glutamic acid/glutamine, glycine, proline, and tyrosine.

TABLE 8

| Amino Acid | ppm |
|---|---|
| Arginine | 3,679 |
| Histidine | 3,456 |
| Isoleucine | 3,028 |
| Leucine | 2,168 |
| Lysine | 3,486 |
| Methionine | 10,460 |
| Phenylalanine | 1,145 |
| Serine | 1,023 |
| Threonine | 4,134 |
| Tryptophan | 2,047 |

TABLE 8-continued

| Amino Acid | ppm |
|---|---|
| Valine | 11,460 |
| Alanine | 10,350 |
| Aspartic Acid/Asparagine | 5,123 |
| Cysteine | 4,134 |
| Glutamic acid/Glutamine | 2,646 |
| Glycine | 1,249 |
| Proline | 5,374 |
| Tyrosine | 7,846 |

Still further, the (FS) material has been found to include about 60 minerals, many of which are believed to be chelated with the monosaccharides and/or the amino acids. Of these 60 elements, six are present in significant amounts (i.e., >1000 ppm).

TABLE 9 provides an example of a typical elemental profile for (FS) material suitable for use in the method.

TABLE 9

| Element | ppm |
|---|---|
| Al | 23,900 |
| Sb | 44 |
| As | 6 |
| Ba | 1.6 |
| Be | 21.7 |
| Bi | 280 |
| B | 340 |
| Br | 5 |
| Ca | 2,700 |
| C | 600 |
| Ce | 24 |
| Cs | 7 |
| Cl | 81 |
| Cr | 385 |
| Co | 75 |
| Cu | 13 |
| Dy | 51 |
| Er | 40 |
| F | 8 |
| Gd | 109 |
| Ga | 22 |
| Ge | 77 |
| Hf | 4 |
| Ho | 11 |
| In | 27 |
| Fe | 104,563 |
| La | 128 |
| Li | 9 |
| Lu | 6 |
| Mg | 9,400 |
| Mn | 520 |
| Nd | 280 |
| Ni | 104 |
| Os | 2 |
| P | 580 |
| K | 6 |
| Pr | 66 |
| Re | 11 |
| Rb | 630 |
| Ru | 8 |
| Sm | 78 |
| Sc | 24 |
| Se | 795 |
| Si | 310 |
| Ag | 5 |
| Na | 12 |
| Sr | 62 |
| S | 26,800 |
| Te | 2 |
| Tb | 9 |
| Tl | 17 |
| Th | 98 |
| Tm | 55 |
| Sn | 18 |

TABLE 9-continued

| Element | ppm |
|---|---|
| Ti | 3 |
| V | 780 |
| Yb | 27 |
| Y | 260 |
| Zn | 1,850 |
| Zr | 5 |

Additionally, the (FS) material has been found to include humic acid, fulvic acid, and humifulvic acid.

In accordance with another aspect of the presently claimed invention, a method for preparing (SFSOM) includes: extracting organic matter from an (FS) material with an aqueous solvent to provide an extract having a pH of about 1.0 to about 4.0; sterilizing the extract; and isolating a monosaccharide, an oligosaccharide, a disaccharide, an amino acid, humic acid, fulvic acid, humifulvic acid, a mineral, or any combination thereof.

Accordingly, the (SFSOM) composition can have a pH of about 1 to about 4, from about 1.1 to about 3.5, from about 1.2 to about 3.4, from about 1.3 to about 3.3, from about 1.4 to about 3.3, from about 1.5 to about 3.2, from about 1.6 to about 3.1, from about 1.7 to about 3.0, from about 1.7 to about 2.9, from about 1.8 to about 2.8, from about 1.9 to about 2.7, from about 2.0 to about 2.6, from about 2.1 to about 2.5, from about 2.2 to about 2.4, or from about 2.3 to about 2.4.

In one embodiment of the presently claimed invention, monosaccharides such as, but not limited to, N-acetylneuraminic acid, N-acetylgalactosamine, N-acetylglucosamine, glucose, fucose, galactose, arabinose, xylose, mannose, and any combination thereof can comprise (SFSOM) and be isolated from it.

In another embodiment of the presently claimed invention, amino acids such as, but not limited to, arginine, histidine, isoleucine, leucine, lysine, methionine, phenylalanine, serine, threonine, tryptophan, valine, alanine, aspartic acid, asparagines, cysteine, glutamic acid, glutamine, glycine, proline, tyrosine, and any combination thereof can comprise the (SFSOM) and be isolated from it.

In yet another embodiment of the presently claimed invention, elements such as, but not limited to, Al, Sb, As, Ba, Be, Bi, B, Br, Ca, C, Ce, Cs, Cl, Cr, Co, Cu, Dy, Er, F, Gd, Ga, Ge, Hf, Ho, In, Fe, La, Li, Lu, Mg, Mn, Nd, Ni, Os, P, K, Pr, Re, Rb, Ru, Sm, Sc, Se, Si, Ag, Na, Sr, S, Te, Tb, Tl, Th, Tm, Sn, Ti, V, Yb, Y, Zn, Zr, and any combination thereof can comprise the (SFSOM) and be isolated from it.

One embodiment of the presently claimed (FS) material extract can be prepared by packing a select amount of (FS) native to North America into an extraction vessel having a flow valve positioned on the bottom of the vessel. Water is added to the FS-packed vessel in a 1:1 ratio, or an amount sufficient to wet and completely submerge the FS. Drip extraction is used and the liquid extract is drawn out of the extraction vessel via the flow valve and collected. This step is repeated, preferably using the collected liquid in place of the water, until the liquid extract attains a pH of about 1.7 to about 2.9. The addition of water of at least 180 degrees Fahrenheit (° F.) can be used during the extraction process to sterilize the extract. The liquid (FS) extract can then be filtered to remove fine particles, and the filtrate is then optionally dried. The dried filtrate can be reconstituted with water in a 1:1 ratio to provide a (FS) extract suitable for use in the method. The resulting extract has a pH in a range of about 1.7 to about 2.9 and can be dark green to brown in color.

Optionally, the iron can be removed from the liquid (FS) extract by any method known to a person having ordinary skill in the art. For example, Potassium Phosphate Monobasic (PPM) can be added either before or after the liquid extract has been sterilized to precipitate out the iron. This process can be repeated until all, or nearly all, of the iron has been precipitated and removed from the liquid extract. The separation of the precipitate from the liquid extract can result in a substantially clear solution.

The sterility of the (FS) organic matter of the embodiments of the presently claimed invention can be verified using the Official Methods of Analysis of AOAC International (AOAC). Method number 990.12 can be used to determine whether the Petrifilm™ aerobic plate count is less than 100 cfu per gram, resulting in sterile profile (i). Method number 991.14 can be used to determine whether the Petrifilm™ coliform plate count is less than 10 cfu per gram, resulting in sterile profile (ii). Additionally, the Food and Drug Administration's (FDA) Bacteriological Analytical Manual (BAM) can be used for microbiological analyses. The method to determine yeasts, molds and mycotoxins of the 7$^{th}$ Edition can be used to determine whether the plate count for each is less than 10 cfu per gram, resulting in sterile profile (iii).

Isolation of the various components of the (SFSOM) can result in a range of concentrations. For example, isolation of N-acetylglucosamine can result in a range from about 0.05 mg/1.0 gm to about 100 mg/1.0 gm; from about 0.10 mg/1.0 gm to about 90 mg/1.0 gm; from about 0.20 mg/1.0 gm to about 70 mg/1.0 gm; from about 0.21 mg/1.0 gm to about 60 mg/1.0 gm; from about 0.22 mg/1.0 gm to about 50 mg/1.0 gm; from about 0.23 mg/1.0 gm to about 40 mg/1.0 gm; from about 0.24 mg/1.0 gm to about 30 mg/1.0 gm; from about 0.25 mg/1.0 gm to about 20 mg/1.0 gm; from about 0.26 mg/1.0 gm to about 10 mg/1.0 gm; from about 0.27 mg/1.0 gm to about 9 mg/1.0 gm; from about 0.28 mg/1.0 gm to about 8 mg/1.0 gm; from about 0.29 mg/1.0 gm to about 7 mg/1.0 gm; from about 0.30 mg/1.0 gm to about 6 mg/1.0 gm; from about 0.31 mg/1.0 gm to about 5 mg/1.0 gm; from about 0.32 mg/1.0 gm to about 4 mg/1.0 gm; from about 0.33 mg/1.0 gm to about 3 mg/1.0 gm; from about 0.34 mg/1.0 gm to about 2 mg/1.0 gm; from about 0.35 mg/1.0 gm to about 1 mg/1.0 gm; from about 0.15 mg/1.0 gm to about 1 mg/1.0 gm; from about 0.20 mg/1.0 gm to about 1 mg/1.0 gm; from about 0.21 mg/1.0 gm to about 0.9 mg/1.0 gm; from about 0.22 mg/1.0 gm to about 0.8 mg/1.0 gm; from about 0.23 mg/1.0 gm to about 0.7 mg/1.0 gm; from about 0.24 mg/1.0 gm to about 0.6 mg/1.0 gm; from about 0.25 mg/1.0 gm to about 0.5 mg/1.0 gm; or from about 0.26 mg/1.0 gm to about 0.4 mg/1.0 gm.

The combinations of organic matter that can comprise and be isolated from (SFSOM) can be derived by various permutations, such as one example found in TABLE 10 where "Y" represents one possible combination that may, or may not, be in addition to the combination found in an adjacent cell(s) along the row. For example, amino acids (AA), antioxidants (AO), minerals (M), monosaccharides (MS), and oligosaccharides (OS), humic acid (HA), fulvic acid (FA), and humifulvic acid (HFA) can comprise and be isolated from (SFSOM). In another permutation, the combination of the (AO), (M), (MS), (OS), (HA), (FA), and/or (HFA) can be isolated from the (SFSOM). In yet another permutation, (M), (MS), (OS), (HA), (FA), and/or (HFA) can be constituents of the (SFSOM). TABLE 10 provides examples of various permutations.

TABLE 10

|       | (AA) | (AO) | (MIN) | (MS) | (OS) | (HA) | (FA) | (HFA) |
|-------|------|------|-------|------|------|------|------|-------|
| (AA)  | Y    | Y    | Y     | Y    | Y    | Y    | Y    | Y     |
| (AO)  |      | Y    | Y     | Y    | Y    | Y    | Y    | Y     |
| (MIN) |      |      | Y     | Y    | Y    | Y    | Y    | Y     |
| (MS)  |      |      |       | Y    | Y    | Y    | Y    | Y     |
| (OS)  |      |      |       |      | Y    | Y    | Y    | Y     |
| (HA)  |      |      |       |      |      | Y    | Y    | Y     |
| (FA)  |      |      |       |      |      |      | Y    | Y     |
| (HFA) |      |      |       |      |      |      |      | Y     |

Various glucose- and/or xylose-containing materials can be reacted with the (FS) extract to produce one or more essential monosaccharides. For example, one such material includes raw Arabica materials taken from the fruit of the coffee plant, *Coffea arabica* L., which contains significant amounts of the monosaccharides glucose and xylose.

In accordance with one embodiment, the (FS) extract ((FN), (FNC), (LE) and/or (SLE), for example) can be reacted with a glucose- and/or xylose-containing material in a volume (ml) to weight (gm) ratio from about 1:60 to about 1:600. Alternatively such ratio (volume (ml) to weight (gm) ratio) can be from about 1:60 to about 1:600; from about 1:50 to about 1:500; from about 1:40 to about 1:400; from about 1:30 to about 1:300; from about 1:20 to about 1:200; from about 1:10 to about 1:100; from about 1:9 to about 1:90; from about 1:8 to about 1:80; from about 1:7 to about 1:70; from about 1:6 to about 1:60; from about 1:5 to about 1:50; from about 1:4 to about 1:40; from about 1:3 to about 1:30; from about 1:2 to about 1:20; from about 1:1 to about 1:10; from about 1:1 to about 1:9; from about 1:1 to about 1:8; from about 1:1 to about 1:7; from about 1:1 to about 1:6; from about 1:1 to about 1:5; from about 1:1 to about 1:4; from about 1:1 to about 1:3; from about 1:1 to about 1:2; and from about 1:1 to about 1:1.5.

Alternatively, such ratio (volume (ml) to weight (gm) ratio) can be from about 60:1 to about 600:1; from about 50:1 to about 500:1; from about 50:1 to about 500:1; from about 50:1 to about 500:1; from about 50:1 to about 500:1; from about 50:1 to about 500:1; from about 40:1 to about 400:1; from about 30:1 to about 300:1; from about 20:1 to about 200:1; from about 10:1 to about 100:1; from about 5:1 to about 50:1; from about 4:1 to about 40:1; from about 3:1 to about 30:1; from about 2:1 to about 20:1; from about 1:1 to about 10:1; from about 1:1 to about 9:1; from about 1:1 to about 8:1; from about 1:1 to about 7:1; from about 1:1 to about 6:1; from about 1:1 to about 5:1; from about 1:1 to about 4:1; from about 1:1 to about 3:1; from about 1:1 to about 2:1; and from about 1.5:1 to about 2:1. In the case of sucrose for example, the ratio (volume (ml) to weight (gm) ratio) may be 2:1 so as to provide 2 ml of (FS) extract, (FN), (FNC), (LE) and/or (SLE) for each 1 gram of sucrose.

Alternatively, or in addition to, a disaccharide source such as in the form of a glucose/fructose 50:50 (w/w) disaccharide can be utilized in a method.

EXAMPLE 1

Preparation of the essential monosaccharides mannose, N-acetylneuraminic acid, N-acetylglucosamine, and combinations thereof.

Soil from the Mt. Olive, Miss. region (Approximately 31°45'24"N 89°39'13"W) is extracted with water as described above to prepare a (FS) liquid extract having a pH of about 1.7 to about 2.9 and comprising monosaccharides, oligosaccharides, disaccharides, amino acids, humic acid, fulvic acid, humifulvic acid, and minerals.

The (FS) liquid extract is sterilized. One example of sterilization is the addition of water with a temperature of at least 180° F. during the extraction process. The resulting (FS) liquid extract will have a sterile profile of (i), (ii), (iii), (iv), or combinations thereof. The completion of this step results (or may result) in the formation of (SFSOM).

(SFSOM) is first added to a 1:1 solution of a disaccharide source (e.g. fructose and glucose optionally at a 50:50 (w/w) ratio) and water, then added to Raw Arabica material, or a suitable source of xylose and/or glucose, and optionally mixed until the mixture turns green in color. The reaction mixture is optionally allowed to stand at room temperature and air dry, leaving behind a green precipitate including said minerals, monosaccharides, oligosaccharides, amino acids, antioxidants, and any combinations thereof. The mixture can then be collected, filtered, and analyzed via standard high-performance liquid chromatography methods to determine the type and amount of each essential monosaccharide present in the reaction product.

The resulting reaction product is found to have a significant decrease in both xylose and glucose, whereas there is a significant increase in mannose and N-acetylglucosamine. Additionally, the reaction product also contains a slight increase in N-acetylneuraminic acid.

EXAMPLE 1A

Preparation of the essential monosaccharides mannose, N-acetylneuraminic acid, and N acetylglucosamine from raw Arabica materials Soil from the Mt. Olive, Miss. region was extracted with water as described above to prepare a soil extract having a pH of about 1.7 to about 2.9 and a monosaccharide profile determined by HPLC as shown in TABLE 11, below.

The soil extract and the raw Arabica material were then reacted, the raw Arabica material having a monosaccharide profile as also shown in TABLE 11.

TABLE 11

| Monosaccharide | Soil Extract (mg/g) | Raw Arabica (mg/g) | Reaction product (mg/g) |
|---|---|---|---|
| Mannose | 4.32 | 3.01 | 27.25 |
| Xylose | 5.64 | 28.91 | 0.0 |
| Arabinose | 6.69 | 0.76 | 0.01 |
| Galactose | 3.11 | 0.95 | 0.55 |
| Fucose | 3.74 | 4.14 | 0.21 |
| Glucose | 2.08 | 38.41 | 0.11 |
| N-acetylneuraminic acid | 4.04 | 3.79 | 4.53 |
| N-acetylgalactosamine | 0.02 | 0.44 | 0.37 |
| N-acetylglucosamine | 0.21 | 0.31 | 38.24 |
| Totals | 25.85 | 80.72 | 71.27 |

The resulting reaction product was found to have a significant decrease in both xylose and glucose whereas there was a significant increase in mannose and N-acetylglucosamine. In particular, the reaction product was found to contain about 8 times more mannose than either of the starting materials and an almost 125 times increase in N-acetylglucosamine. Additionally, the reaction product also contained nearly static levels of N-acetylneuraminic acid.

EXAMPLE 2

This example relates to an embodiment for preparation of the monosaccharides mannose, arabinose, xylose, N-acetylneuraminic acid, N-acetylglucosamine, and combinations thereof.

Soil from the Mt. Olive, Miss. region (Approximately 31°45'24"N 89°39'13"W) is extracted with water as described above to prepare a (FS) liquid extract having a pH of about 1.7 to about 2.9 and comprising monosaccharides, oligosaccharides, disaccharides, amino acids, humic acid, fulvic acid, humifulvic acid, and minerals.

The (FS) liquid extract is sterilized. This step can occur either before or after the dissolved iron content is removed. One example of sterilization is the addition of water with a temperature of at least 180° F. during the extraction process. The resulting liquid extract would result in a sterile profile of (i), (ii), (iii), (iv), or combinations thereof as described hereinabove.

Dissolved iron is removed from the (FS) liquid extract. This step can occur either before or after sterilization. For example, Potassium Phosphate Monobasic (PPM) is added to the (FS) liquid extract to form an iron precipitate, which can then be removed from the (FS) liquid extract. Once the dissolved iron content is removed, a substantially clear liquid extract solution remains.

Sterilization and removal of the dissolved iron content from the (FS) liquid extract results in (SFSOM) essentially free of iron.

(SFSOM) essentially free of iron is added to a 2.5:1 solution of a disaccharide source (e.g. fructose and glucose optionally at a 50:50 (w/w) ratio) and water, and optionally mixed. The reaction mixture is optionally allowed to stand at room temperature and air dry, leaving behind a green precipitate including said minerals, monosaccharides, oligosaccharides, amino acids, antioxidants, and any combinations thereof. The mixture can then be collected, filtered, and analyzed via standard high-performance liquid chromatography methods to determine the type and amount of each essential monosaccharide present in the reaction product.

After the soil extract and the disaccharide solution is reacted, the resulting reaction product may contain certain amounts of one or more of mannose, arabinose, N-acetylneuraminic acid and N-acetylglucosamine. An approximately 50% increase in the amount of xylose is possible.

Figure 2:
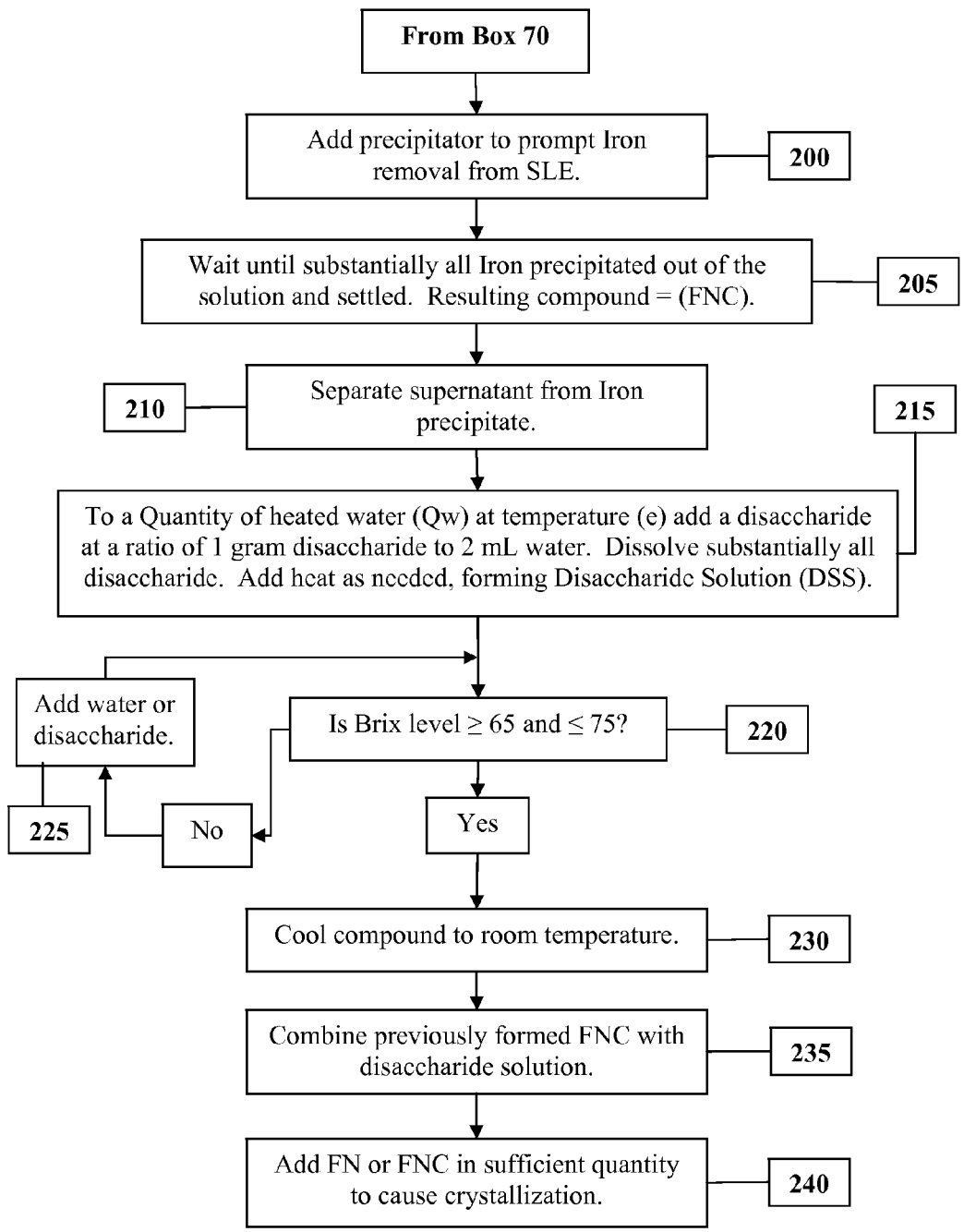
FIG. 2 provides a flowchart of another embodiment of a process suitable for use in connection with the presently claimed invention.
Figure 3:
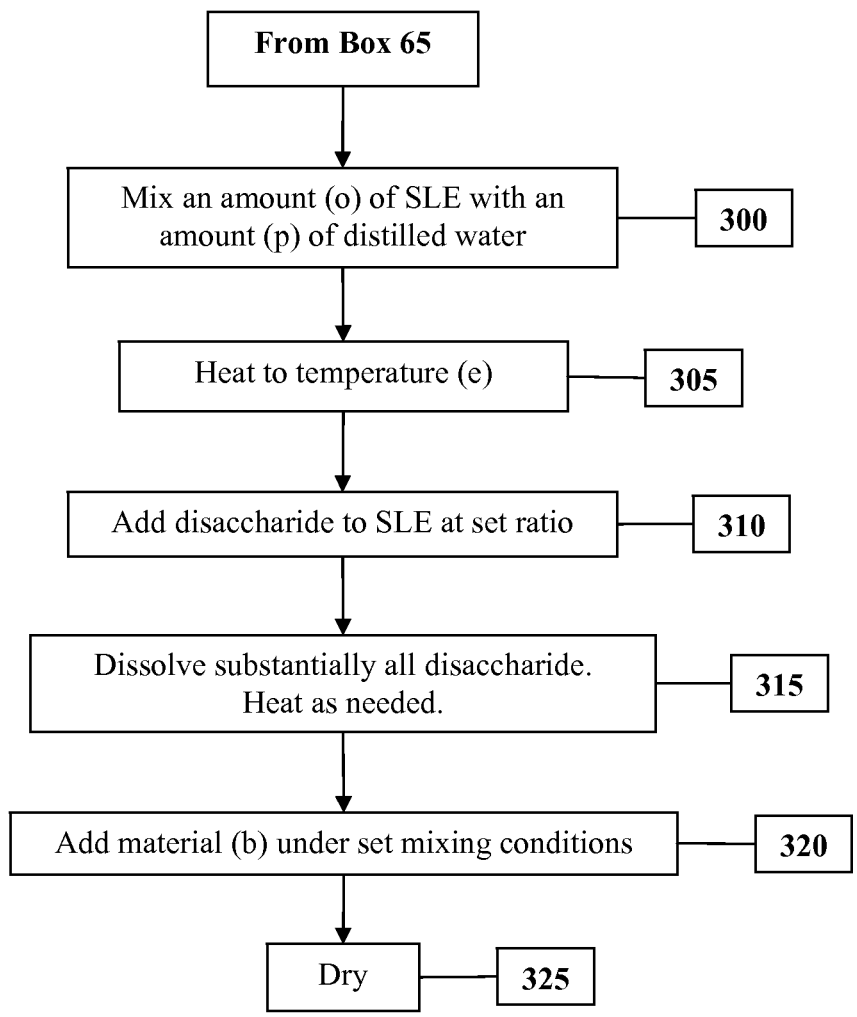
FIG. 3 provides a flowchart of yet another embodiment of a process suitable for use in connection with the presently claimed invention.

A further description of the illustrative processes of FIGS. 1-3 is provided below. It is to be noted that other variations of the procedures denoted herein and at FIGS. 1-3 may be used as alternatives. Such variations would be readily understood by one of ordinary skill in the art given the benefit of the knowledge provided by this application.

With respect to its non-limiting process embodiments, FIG. 1 depicts one such embodiment. In FIG. 1, the process may begin with a soil (S) or a fossilized soil (FS) at box (10) with a Count=0 also at box (10). Optionally the (S) and/or (FS) may be loosened to facilitate fluid flow through the soil rather than over it at label (15). A drip extraction process is carried out using an appropriate solvent (e.g., water, distilled water, ground water, ionized water, sterile water, etc.) at box (20). The liquid extract (LE) is collected as noted at (25), and its pH level is measured ($pH_{sample}$) as noted at box (30). Note that any suitable form of extraction other than drip extraction may be used. Where an equivalent of extraction is available, then such equivalent may be used if appropriate as would be recognized by one of ordinary skill in the art provided with the benefit of the disclosure of this application.

Also note that the time interval for measuring the pH level of the drip extracted liquid extract (LE) may be accomplished by continuous monitoring of the drip extraction collected liquid extract (LE)—for example by use of a pH meter connected to a pH probe ultimately connected to a monitoring computer or may be monitored manually or my use of pH paper and color change or by pH indicator and color change or an equivalent of the same. The pH monitoring could be at certain intervals of time rather than continuous monitoring as could be accomplished by a computer. The pH monitoring interval could be every nanosecond, every millisecond, every 100 milliseconds, every 500 milliseconds, every second, every 5 seconds, every 10 seconds, every 20 seconds, matched to the time interval of each drop of liquid as it drips into the liquid extract (so that if each drop drips at an interval of every 5 seconds, then the pH is measured every 5 seconds; or if each drop drips at a varying interval some longer and some shorter, then the pH could be measured after each drop as it drips into the collected liquid extract, sometimes at shorter time intervals and sometimes at longer time intervals; every 10 seconds, every 20 seconds, every 30 seconds, every 40 seconds, every 50 seconds, every 60 seconds, every 1.5 minutes, every 2 minutes, every 3 minutes, every 4 minutes, every 5 minutes, every 6 minutes, every 7 minutes, every 8 minutes, every 9 minutes, every 10 minutes, every 11 minutes so long as the drip extraction process is actively adding more liquid extract to the collected (LE) at (25) for example), or the pH may be measured only when the LE volume reaches increments of 100 ml, 200 ml, 300 ml, . . . 1 liter, etc. with a base minimum volume set at given volume (e.g., base minimum LE volume of 5 ml, 10 ml, 20 ml, 30 ml, 40 ml, 50 ml, 60 ml, 70 ml, 80 ml, 90 ml, 100 ml, 150 ml, 200 ml, 300 ml, 400 ml, 500 ml, 600 ml, 700 ml, 800 ml, 900 ml, 1 liter, etc.), or any combination of the above (e.g., if base volume is reached, if time interval is passed, if (LE) is being collected, as may be desired).

It is determined if the measured $pH_{sample}$ at (30) falls within a set range, $pH_l$ to $pH_h$ at (35). Note that if the $pH_{sample}$ is within a set range, $pH_l$ to $pH_h$ at (35), then it will always be true that $pH_{sample}$ is less than or equal to $pH_h$ at (40).

If the $pH_{sample}$ is less than or equal to $pH_h$ (40), then proceed to (45) and compare the sample color to a reference color (45). The reference color may be correlated to a reference liquid extract (e.g., the reference liquid extract may be an identified liquid extract having a certain color such as darkness, such as the tint of the color itself meaning brown or black versus clear or blue or green or some other color criterion. The reference color could be correlated to solids content or some other correlation such as wavelength of light reflection or absorbance, etc. In such case, such other property correlated to sample color and reference color could be used instead of the color comparison noted at (45) in place of color so long as a sufficiently reliable comparison and correlation could be made using some other parameter other than a color comparison. However, for the present time, it may be that the color comparison may be the simplest but later could be better refined using % light transmission, % reflectance, % density, % absorbance at a given wavelength, % refraction, % reflection at a given wavelength, some other relevant correlation between reference liquid extract and sample liquid extract to achieve the end result similar to, as good as, nearly as good as, or better than may be achieved with the use of a color comparison.

In any event, if using a color comparison of the sample (LE) color versus a color of a reference (LE), then the sample color could be monitored visually or by some spectrometer connected to a computer in much the same way with respect to the time interval between successive comparisons and monitoring of sample (LE) color against reference color. It may be that a reference color may not be needed or that the reference color may be gradually changed to accommodate the situation where the amount being extracted with each successive drip extraction is likely to yield less and less of the desired content from the (S) or (FS) being extracted with the extraction liquid (e.g., locally well water, local ground water, etc.)

Alternatively, both the sample color and sample pH ($pH_{sample}$) could be simultaneously monitored together rather than as noted in FIG. 1 as being monitored separately at box (30) and then at box (45). It may be that the measurements of sample pH and sample color may be conducted continuously, simultaneously and/or or at a suitable time interval. It may, however, be that the comparison of the $pH_{sample}$ to the set pH range ($pH_l$ to $pH_h$) or to the set $pH_h$ value may occur at box (30), for example. Similarly, the sample color comparison to the set reference color may be conducted at different times than as at box (45). Or the relevant comparisons may be made as indicated at box (35) (with respect to pH) and at box (45) (with respect to color), for example.

With reference to the color comparison at (45), if the color of the (LE) sample is darker than the reference color at (45), then proceed to process/procedure at (50).

If the $pH_{sample}$ is greater than $pH_h$ at (40), then determine if the Count (originally set at Count=0 at (10)) is less than set value X (55). If the Count is less than set value X (55), then increase current value of Count by +1 at (55). Then continue drip extraction at (20), and repeat the procedures at boxes (20)-(40) while the Count is less than X at (55). Note that with each repetition of continuation of cycle at (20)-(40)), increase each successive count value by +1 such that current Count=previous Count+1 (55) while $pH_{sample}$ is greater than $pH_h$ at (40). Alternately stated, Count=Count+1 with each iteration at (55) until the Count comparison yields the result that Count is greater than or equal to X at (55). At that point, proceed to box at (50).

Once the Count is greater than or equal to X as revealed by comparison at box (55) or once the color of the sample is darker than the reference color at (45), proceed to process/procedure at box (50). Note that X may be set to some number, typically, any integer (e.g., 1, 2, 3, 4, 5, 6, 7, 8, 9, 10, 11, . . . 1000, 1001, . . . 2000, . . . 10,000, etc.; any integer between 1 to 1,000; between 1 to 10,000; between 1-20,000; between 1-30,000; between 1-40,000; between 1-50,000; between 1-60,000; between 1-70,000; between 1-80,000; between 1-90,000; between 1-100,000; between 1-200,000; between 1-300,000; between 1-400,000; between 1-500,000; between 1-1,000,000 and so on depending upon how often the pH comparisons and the color comparisons may be made, for example, as noted at box (35) and/or at box (45); alternatively, it may be desirable to set X to such high value that the drip extraction occurs until it is dictated at box (40) that the pH is at or below $pH_h$ and/or the sample color is at or darker than a set reference color at box (45). Alternatively, X may be set at e.g. X=5 so that the drip extraction procedure is carried out for X+1 cycles before being kicked out at box (55) as being sufficient even if the pH comparison at box (40) is such that $pH_{sample}$ is not less than or equal to $pH_h$.

At any rate, at box (50) the (LE) may be sterilized to yield a sterilized (LE) denoted herein as (SLE).

Preferably, sterilization may be accomplished by heating, filtration, UV light, pasteurization or by all methods other than by pasteurization. Sterilization may not be possible by use of a 0.22 micron filter because it may be that the LE contains ingredients that would not pass through a 0.22 micron filter while still keeping the desirable particulate matter within the (LE). If necessary, it may be desirable to use a 0.22 micron filter, and then to separately collect any solids and heat those solids to a sufficient temperature and for a time to guarantee sterility of the solids so collected via use of a 0.22 micron or other suitable filter or filters. Thereafter, once the solids are chemically or heat treated to achieve sterility of the solids so as to render any pathogenic or other bacterial, microbial, viral, toxic or other contents harmless, such solids could be recombined with the filter sterilized (LE) using a 0.22 micron filter. In such manner, any heat labile dissolved contents of the LE could be spared heat or chemical degradation by heat or chemical sterilization reserved just for solids collected. By such sterilization process, both dissolved heat labile or chemical labile (LE) constituents could be sterilized via filtration with a 0.22 micron filtration method. And solids that are not heat or not chemical treatment labile could be recombined with the sterilized (LE) obtained via 0.22 micron filtration. In such manner, those desirable solids could be preserved and sterilized if possible and those desirable heat labile or chemical labile dissolved (LE) constituents could be preserved for use in the form of a more potent or desirable (SLE). The relevant point being that whatever sterilization techniques are suitable may be used if so desired. Of course, if the sterilization procedure is too expensive compared to another method or is faster compared to another equally suitable method, then one may opt for the best, cheapest, most efficient of methods or some combination of the above to reduce cost and increase productivity. In effect, one may use a less elegant sterilization method if such method accomplished the sought objective. Ultimately, heat sterilization may be utilized so long as conducted under conditions sufficient to sterilize without the excessive loss of stability (50). The resulting sterilized (LE) is denoted as (SLE) at (50).

Also, sterilization may be conducted at (50) or at any other point along the processes of FIG. 1, 2, or 3 so long as the desired product is obtained at the end.

Where sterilization is unnecessary, the process at (50) could be skipped altogether. Thereafter, proceed to box (60). Nevertheless, the appropriate level of sterilization should be provided.

Note that sterilization may optionally be conducted after the Fe (iron) is removed (e.g., at box (200) of FIG. 2) or at any point where the sterilization procedure is sufficient to support or facilitate the safe and effective intended use of the relevant product in humans and/or animals. Intended uses may vary. Sub-populations in whom a particular product may be used may also vary. For example, a product or an intermediate may be sterilized sufficient for ingestion by humans or a sub-category of humans such as the elderly; the immune compromised; the young (ages 6-12; ages 13-19; ages 20-30); the early middle aged (ages 30-40; ages 40-50); the mature middle aged (ages 50-60); the early elderly (ages 60-70); the mature elderly (ages 70-80, ages 80-85); and the geriatric aged (ages 85-90; ages 90+). Note that the category names used are somewhat arbitrary and are not intended to classify any person as too old or too young. Exceptions do exist and such is recognized here, but the labels are used for convenience sake only. Other examples of sub-populations of humans in whom nutritional products may be use include, but are not limited to, those suffering from a malnutrition ailment; those suffering from diabetes (adult onset or juvenile diabetes); those suffering from Crohn's disease; those suffering from ulcerative colitis; those suffering from irritable bowel syndrome; those suffering from anorexia or bulimia or both; those that are underweight; those that require nutritional supplementation; those who require increased replenishment of a body's nutritional needs due to excessive activity, exercise, lack of opportunity for proper meals, etc.; those that require increased caloric intake, etc. Other than ingestion, certain products may be used in topical formulations or may need to be sufficiently safe for handling even if not ingested. Thus, sterilization may simply be that which is sufficient for skin contact and/or absorption through the skin. The topical product may be a topical preparation, a cosmetic, and the like, etc. The sterilization may simply be sufficient for uses in or with animals, etc. However, sterilization may be beyond that is strictly needed or the level or sterilization may be dictated by regulations of the FDA, USDA, or other governmental regulation. In such case, the appropriate level of sterilization should be followed.

It is then determined whether or not it is desirable to remove Iron (Fe) from the resulting compound (SLE) (60).

FIG. 2 reflects one embodiment of the procedure for removing Iron (Fe) from the resulting compound (SLE) at box (70), and FIG. 3 reflects one embodiment of the procedure when Iron (Fe) is allowed to remain in the resulting compound (SLE) (65).

With respect to its non-limiting process embodiments, FIG. 2 depicts one such embodiment. FIG. 2 reflects the process utilized when it is desirable to remove Iron (Fe) from the resulting compound SLE (70). In order to remove the Iron (Fe), first, a precipitator is used to promote Iron (Fe) removal from SLE (200). Substantially all of the Iron (Fe) is precipitated out of the solution and settled (205). The resulting compound is FNC (205). The iron precipitate is then removed from the supernatant (210). Separately, a quantity of water is heated to a temperature (e) (215). Then a disaccharide is added to the heated water (Qw) at a ratio of one gram of disaccharide for every 2 milliliters of water (215). The disaccharide is preferably (or may need to be) substantially dissolved, and heat may be added to aid in dissolution to form the Disaccharide Solution (DSS) (215). The Brix measurement is then satisfied for the Disaccharide Solution (DSS), and therefore, an amount of water or disaccharide should be added as needed (225) until the Brix level is greater or equal to 65 and less than or equal to 75 (220). Once the Brix level is attained, the Disaccharide Solution (DSS) solution should be cooled to room temperature (220).

Once the DSS is at room temperature (230), the previously formed (FNC) (see flow chart of FIG. 2 at boxes (200)-(210)) may be combined with the (DSS) (235). Add (FN) and/or (FNC) in sufficient quantity to cause or initiate crystallization (240). A sweetener product was made according to this example, in vitro glycemic index=53.5. Glycemic index (GI) was determined as an in vitro estimate using standard methods (Silliker Inc., Chicago Heights, Ill.).

With respect to non-limiting process embodiments, FIG. 3 depicts one such embodiment. FIG. 3 reflects the process that may be utilized when it is desirable to allow Iron (Fe) to remain in the resulting (SLE) as denoted at boxes (60) and (65) of FIG. 1. Proceed from box (65) of FIG. 1 to box (300) of FIG. 3. Mix an amount (O) of (SLE) with an amount (p) of distilled water (300). Then heat the so formed (SLE) solution to temperature (e) at box (305), and add disaccharide to the (SLE) solution at a set ratio (310). The disaccharide is to be substantially dissolved (with applied heat as necessary). Heat may be applied at box (305) to aid in subsequent dissolution at box (315) of the disaccharide added at box (310). Then add material (b), as listed below, under set mixing conditions (320), and finally dry the resultant solution (325), preferably to yield a dry solid product or a solid product with an acceptable level of moisture content (i.e. dried or desiccated).

Amount (p) of distilled water at box (300) may be just enough water so that it is sufficient to dissolve the amount of disaccharide to be added at box (310) at temperature (e) specified at box (305). For example, the amount of water (p) may be 2 ml per 1 gram of disaccharide added at box (310). The amount of disaccharide added at box (310) can be varied as desired all the way up to the amount of disaccharide that can be added to form a saturated solution of the disaccharide at the relevant amount of water (p) used at the relevant water temperature (e). A typical temperature (e) may be about 200° C., about 190° C., about 180° C., about 170° C., about 160° C., about 150° C., about 140° C., about 130° C., about 120° C., about 110° C., about 100° C., or some combination of same over selected time frames such that the requisite amount of disaccharide is dissolved, such that the solution of (SLE) and (DS) is further sterilized if necessary, such that the desirable constituents of the solution of (SLE) an (DS) are preserved in the form needed, and/or such that the requisite reaction of the constituents in the solution of (SLE) and (DS) is promoted, initiated, and/or completed so as to ultimately facilitate and yield the dry product at box (325).

Figure 4:
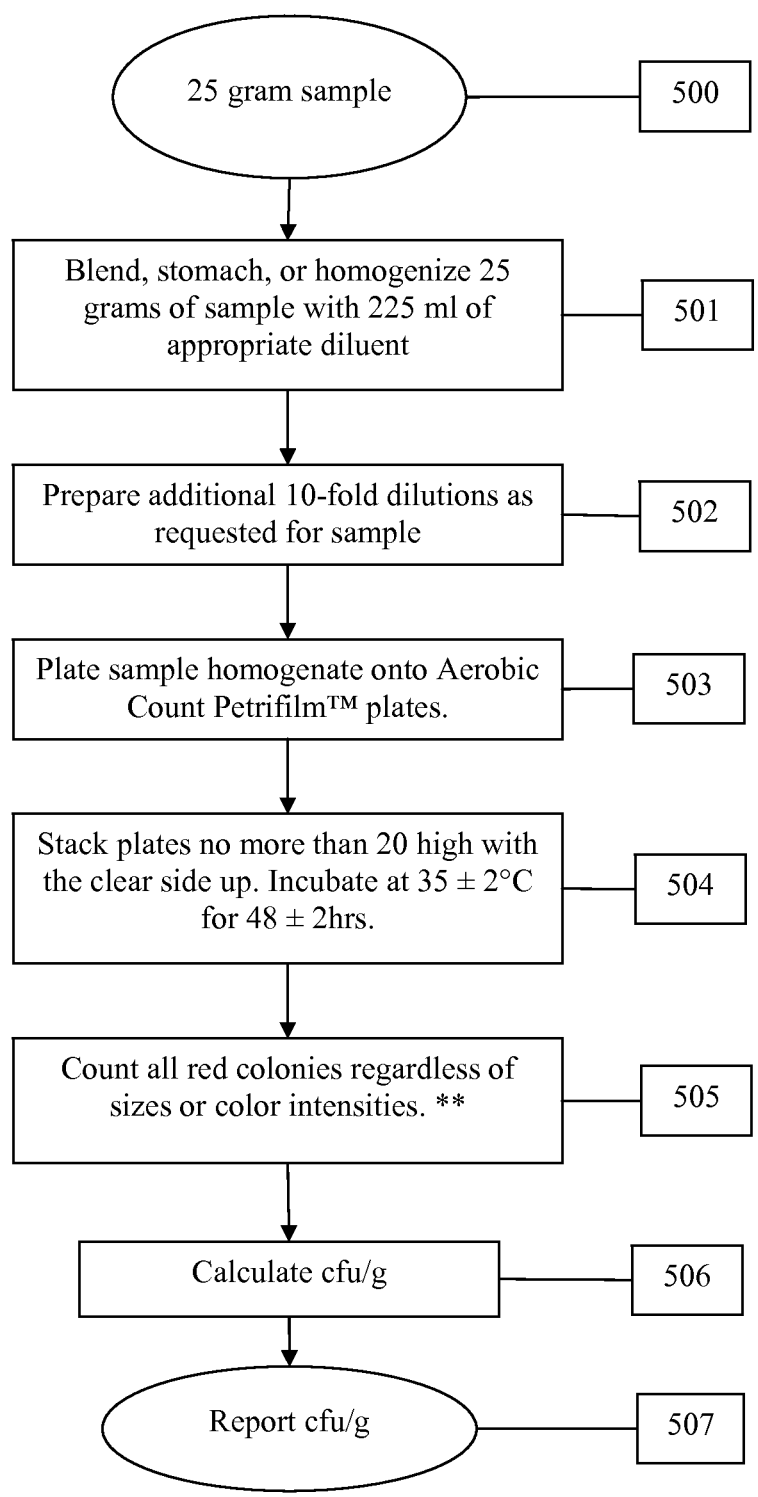
FIG. 4 provides a flowchart of yet another embodiment of a process suitable for use in connection with the presently claimed invention relating to aerobic plate count (APC).

FIG. 4 relates to an illustrative non-limiting process for determining whether a particular sample satisfies a particular (APC) or coliform sterility standard pursuant to one or more of the AOAC procedures and/or according to the relevant procedures described herein. In particular, at box (500), a 25 gram sample of the test sample is obtained. That test sample is then blended, or homogenized with 225 ml of an appropriate diluent (e.g., sterile water or sterile water with appropriate nutrients and the appropriate pH with appropriate buffer, etc. as would be known to one of ordinary skill in the art of conducting aerobic plate counts on Petrifilm™ Plates, for example). See box (501). Then, pursuant to box (502), the diluted blend/homogenate from box 501 is further diluted another 10-fold with an appropriate diluent (e.g., sterile water or sterile water with appropriate nutrients and the appropriate pH with appropriate buffer, etc. as would be known to one of ordinary skill in the art of conducting aerobic plate counts on Petrifilm™ Plates, for example). Then as noted at box (503), the diluted sample homogenate at box (502) is plated onto Aerobic Count Petrifilm™ Plates. Pursuant to box (504), the plated Aerobic Count Petrifilm™ Plates (or coliform plates) should be stacked no more than 20 high (per stack) with clear side up (i.e., the nutrient or media or agar side down) and then these stacked plates are incubated for an appropriate time and at an appropriate temperature (e.g., incubate at 35±2° C. for 48 hours±2 hours) as noted at box (504). Thereafter, as noted at box 505, all red colonies are counted regardless of size or color intensity. It is noted by the double asterisks () at box (505) refer to the use of 2,3,5,-triphenyltetrazolium chloride) as the indicator used in conjunction with the Petrifilm™ media, agar and/or nutrient as indicated in this embodiment. Pursuant to the use of the 2,3,5,-triphenyltetrazolium chloride indicator, all colonies appear red on the Petrifilm™ agar, if any colonies appear after incubation.

After the incubation period noted at box (504), the red colonies are counted as noted at box (505). Using the value of the number of red colonies counted, the value of the colony forming units per gram (cfu/g) of the test sample is calculated. If appropriate, the (cfu/g) values per plate may be averaged over the 20 (or over however many plates that were plated, incubated and then counted).

In addition, a mean, median and standard deviation for each set of Petrifilm™ plates incubated and counted may be determined such that the relevant sterility determination may be confirmed (if falling within the set threshold for sterility used such as less than or equal to 10 cfu/g etc., for example) using the mean (cfu/g) count with a corresponding standard deviation of same as would be considered appropriate by one of ordinary skill in the art. Also, all appropriate aseptic techniques, reagents and equipment should be used as would be done by one of ordinary skill in the art of conducting sterility and/or safety testing with respect to the relevant organism being tested for or tested against (e.g., coliform contamination, etc.).

Thereafter, pursuant to box (507), the calculated (cfu/g) value may be reported as either satisfying the corresponding sterility requirement or as failing such sterility requirement. Of course, those batches failing a given sterility requirement may be discarded or further sterilized to bring such failed batch into compliance. See for example the various sterility profiles described herein including those recited in the appended claims.

Figure 5:
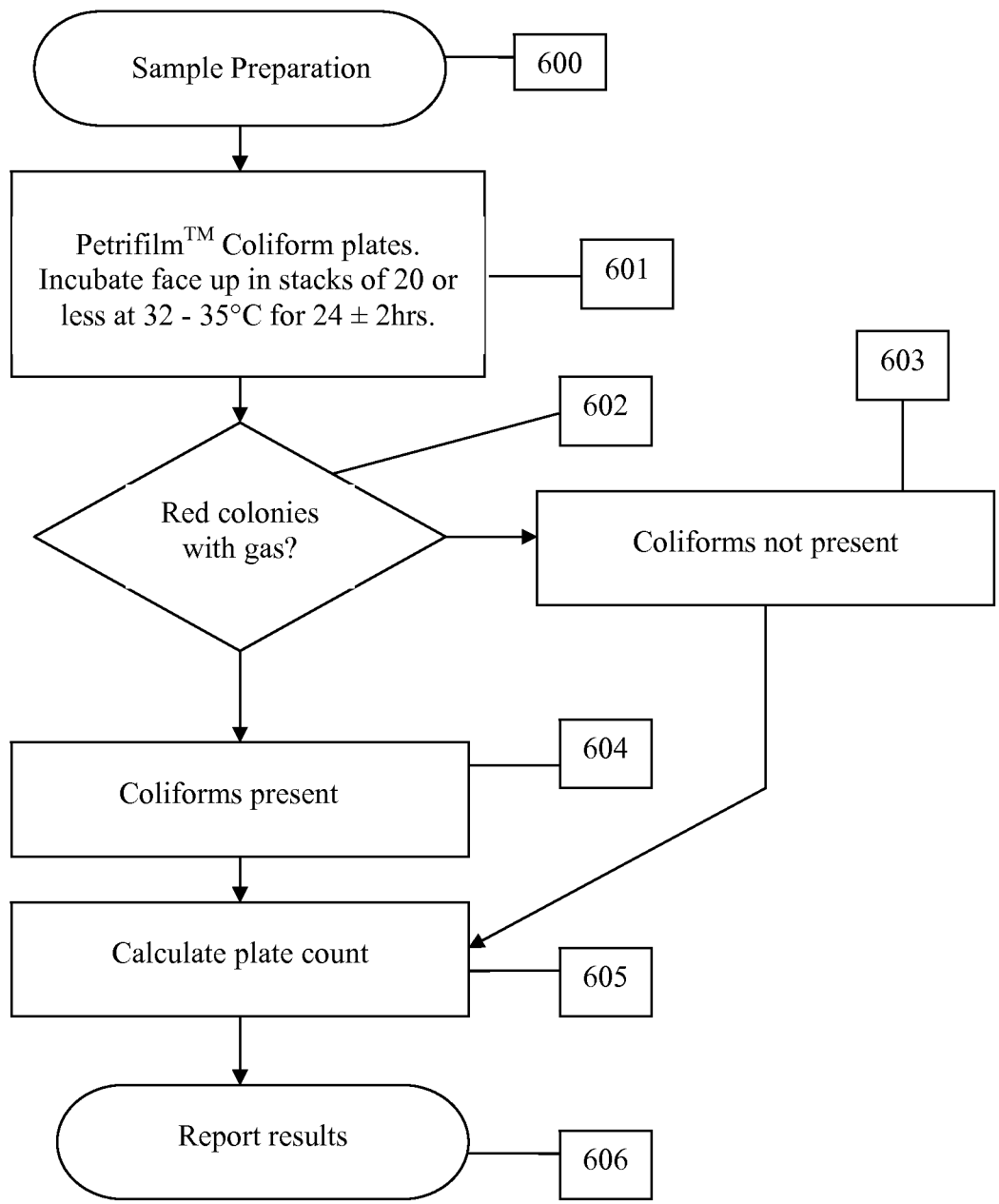
FIG. 5 provides a flowchart of yet another embodiment of a process suitable for use in connection with the presently claimed invention relating to coliform count.

FIG. 5 relates to an illustrative non-limiting process for determining whether a particular sample satisfies a particular coliform count sterility standard pursuant to AOAC procedures and/or according to procedures noted herein. In particular, sample preparation is addressed at box (600). See FIG. 4 in connection with the detail relating to sample preparation at boxes (500), (501), and (502). Thereafter, the relevant Petrifilm™ plates are plated. See for example box (503) of FIG. 4. Once similarly plated, pursuant to box (601) of FIG. 5, the appropriate Petrifilm™ Coliform plates are incubated in much the same manner noted as at box (504) of FIG. 4. Specifically, it is preferable to stack (for example, clear side up and media side down) the Petrifilm™ Coliform plates no more than 20 plates (per stack) at an appropriate temperature and for an appropriate time (e.g., at about 32 to about 35° C. for 24 hours±2 hours). See box (601), for example. Thereafter pursuant to box (602) if there are any red colonies with gas present, then coliforms are present as noted at box (604) in conjunction with box (602). If no red colonies with gas are present, then no coliforms are present as noted at box (603) in conjunction with box (602). If, however, coliforms are present as noted at box (604) then the plate count of gas formed colonies is made (similar to the procedure noted in FIG. 4 at box (505), but only with respect to those colonies that indicate red colonies with gas having formed). Such plate count is then used to calculate the plate count of coliform colonies formed and such value may be reported in colony forming units per gram (cfu/g) of the sample tested pursuant to the procedure of FIG. 5. If no coliforms are present as noted pursuant to box (603) in conjunction with box (602), then the coliform plate count would equal zero and the corresponding (cfu/g) value would also equal zero. Such result may then be reported respect to formed coliforms or an absence of formed coliforms.

Similarly as with FIG. 4, with respect to FIG. 5, after the incubation period noted at box (601), the red colonies with gas are counted as noted at box (602). Using the value of the number of red colonies with gas counted, the value of the colony forming units per gram (cfu/g) of the test sample (for coliforms—red colonies with gas) is calculated. If appropriate, the (cfu/g) values per plate may be averaged over the 20 (or over however many plates that were plated, incubated and then counted).

In addition, a mean, median and standard deviation for each set of Petrifilm™ plates incubated and counted may be determined such that the relevant sterility determination may be confirmed (if falling within the set threshold for sterility used such as less than or equal to 10 cfu/g etc., for example) using the mean (cfu/g) count with a corresponding standard deviation of the same as would be considered appropriate by one of ordinary skill in the art. Also, all appropriate aseptic techniques, reagents and equipment should be used as would be done by one of ordinary skill in the art of conducting sterility and/or safety testing with respect to the relevant organism(s) being tested for or tested against (e.g., coliform contamination, etc.).

Thereafter, pursuant to box (606), the calculated (cfu/g) value may be reported as either satisfying the corresponding sterility requirement or as failing such sterility requirement.

Of course, those batches failing a given sterility requirement may be discarded or further sterilized to bring such failed batch into compliance. See for example the various sterility profiles described herein including those recited in the appended claims.

Figure 6:
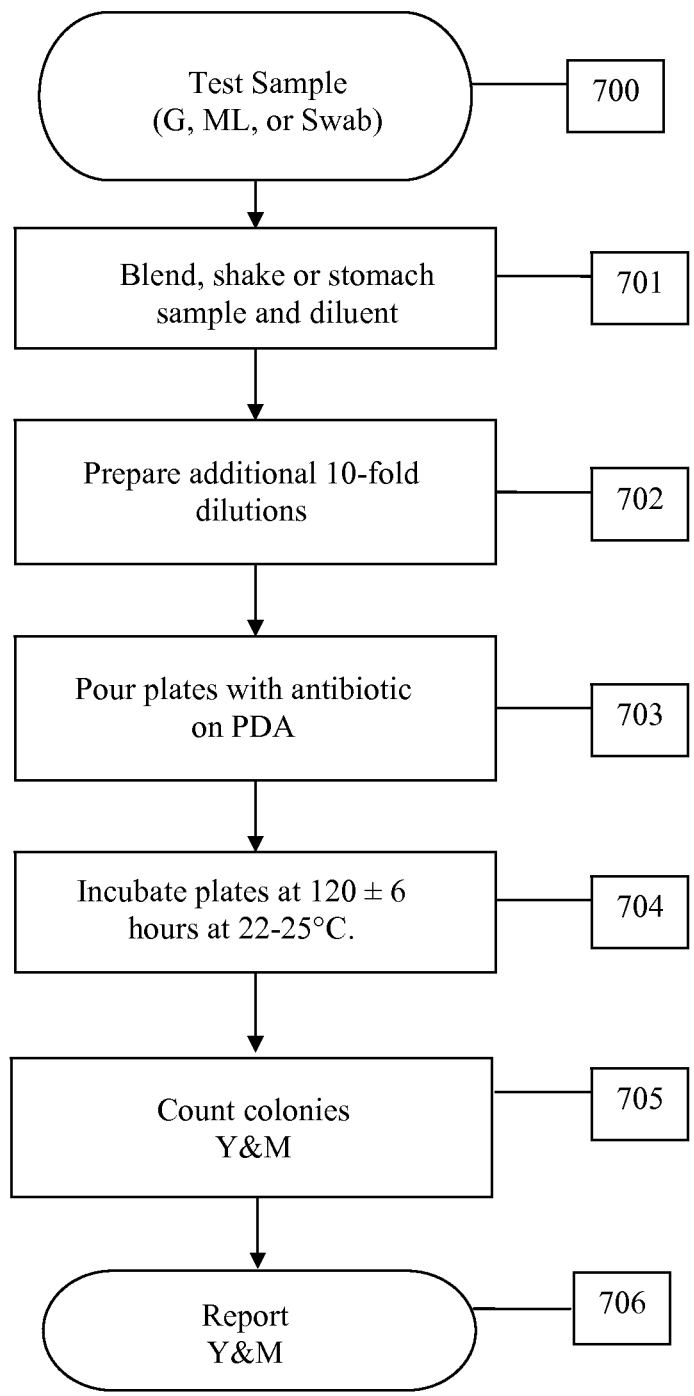
FIG. 6 provides a flowchart of yet another embodiment of a process suitable for use in connection with the presently claimed invention relating to yeast (Y) and mold (M) counts denoted as "Y & M".

FIG. 6 relates to an illustrative non-limiting process for determining whether a particular sample satisfies a particular yeast, mold and/or yeast and mold count sterility standard pursuant to FDA-BAM, $7^{th}$ Ed. and/or FDA-BAM, $8^{th}$ Ed. and/or according to procedures noted herein. In particular, a test sample (in grams G, or in milliliters of volume ML, or in a swab of the test sample) is provided as noted at box (700). The sample is then digested (stomach sample), blended, or shaken and diluent added as noted at box 701. Thereafter, a further additional 10-fold dilution (e.g., of the blended or stomached or homogenized and/or diluted sample) is formed pursuant to box (702). The dilutions are then poured with appropriate antibiotics of choice onto potato dextrose agar (PDA) as noted at box (703). Then plates are then incubated for an appropriate time and appropriate temperature (e.g., 120±6 hour from about 22 to about 25° C. See box (704). Thereafter, the appropriate yeast and/or mold colonies are counted as noted at box 705. And, using the relevant yeast or mold count ((Y) count) or (M) mold count)), the relevant counts are made and then the values used. See box (706) of FIG. 6.

Similarly as with FIG. 4, with respect to FIG. 6, after the incubation period noted at box (704), the yeast or mold are counted as noted at box (705). Using the value of the number of yeast or mold colonies present and counted, the value of the colony forming units per gram (cfu/g) of the test sample (for yeast or mold) is calculated. If appropriate, the (cfu/g) values per plate may be averaged over the 20 (or over however many plates that were plated, incubated and then counted).

In addition, a mean, median and standard deviation for each set of plates incubated and counted may be determined such that the relevant sterility determination may be confirmed (if falling within the set threshold for sterility used such as less than or equal to 10 cfu/g etc., for example) using the mean (cfu/g) count with a corresponding standard deviation of the same as would be considered appropriate by one of ordinary skill in the art. Also, all appropriate aseptic techniques, reagents and equipment should be used as would be done by one of ordinary skill in the art of conducting sterility and/or safety testing with respect to the relevant organism(s) being tested for or tested against (e.g., yeast and/or mold contamination, etc.).

Thereafter, pursuant to box (706), the calculated (cfu/g) value may be reported as either satisfying the corresponding sterility requirement or as failing such sterility requirement. Of course, those batches failing a given sterility requirement may be discarded or further sterilized to bring such failed batch into compliance. See for example the various sterility profiles described herein including those recited in the appended claims.

Materials (b) that may be added may be one or more of the amino acids described herein, may be one or more of the elements or minerals described herein, one or more of the other constituents described herein including, but not limited to, (1) monosaccharides; (2) mannose, (3) arabinose, (4) xylose, (5) N-acetylneuraminic acid, (6) N-acetylglucosamine, and (7) combinations thereof.

The composition formed may be an (SFSOM) including one or more of: N-acetylneuraminic acid; N-acetylgalactosamine; Glucose; Fucose; Galactose; Arabinose; Xylose; and Mannose.

The composition formed may be an (SFSOM) including one or more of: N-acetylneuraminic acid; N-acetylglucosamine; N-acetylgalactosamine; Glucose; Fucose; Galactose; Arabinose; Xylose; and Mannose. Each monosaccharide can be present in an amount from about 9 ppm to about 38,240 ppm.

The composition formed may be an (SFSOM) having a total monosaccharide content up to about 71,200 ppm including one or more of: N-acetylneuraminic acid; N-acetylgalactosamine; Glucose; Fucose; Galactose; Arabinose; Xylose; Mannose; and combinations thereof.

The chemical structures as shown above are represented by the formulas as indicated: N-acetylglucosamine (Formula 1), N-acetylneuraminic acid (Formula 2), Mannose (Formula 3), Arabinose (Formula 4), Glucose (Formula 5), Galactose (Formula 6), Fucose (Formula 7), Xylose (Formula 8), and N-acetylgalactosamine (Formula 9).

EXAMPLE 3

First Formulational Embodiment Process

According to this example, a sweetener of Formulation I may be made as follows:
- (a) Step 1—Similar to FIG. 1, box (10) and optionally box (15): Take fossilized soil (FS) from the ground and put it in a barrel.
- (b) Step 2—Similar to FIG. 1, box (20) and optionally box (15): Take water from a nearby well and drip in soil to extract the (FN).
- (c) Step 3—Similar to FIG. 1, boxes (25), (30), (35), (40), (45), (55) and loop back to box (20) until loop out to box (50) directly from box (45) or indirectly via box (55): Re-drip as necessary to complete the extraction: Result: 60 trace minerals; Monosaccharides; Amino acids, antioxidants at a certain pH.
- (d) Step 4—Similar to FIG. 1, box (50) to form Sterilized Liquid Extract (SLE): Heat the (FN) to 180° F. to sterilize.
- (e) Step 5—Similar to FIG. 1, proceed from box (60) to box (70) if decide to remove Iron (Fe) from SLE (sterilized liquid extract) of box (50); Step 5 is similar to the transition from FIG. 1 via box (70) to FIG. 2 box (200): In a lab (or suitably safe location with requisite safety equipment), add a sufficient amount of soluble phosphate (or its equivalent) to the (FN) before sterilization or to the (FN) after sterilization (FN)/(SLE) of box (50) in FIG. 1, of box (60) in FIG. 1, of box (70) in FIG. 1 to transition to box (200) of FIG. 2, in order to precipitate out the Iron (Fe) (if any is present) in the (FN)/(SLE) noted herein at box (50), at box (60), at box (70), and/or at box (200). Regarding Timing of Sterilization Certain Options Are/May Be Relevant. As noted, the sterilization procedure may be carried out at box (50), at box (60), at box (70), at box (200). As an alternative, the sterilization procedure may be carried out before box (50), before box (60), before box (70), and/or before box (200). As another alternative, the sterilization procedure may be carried out after box (50), after box (60), after box (70), and/or after box (200), if sufficient to render or provide a product safe for its intended use in a human and/or an animal and/or around humans and/or animals so as not be a danger and/or hazard to humans (e.g., men, women, children, toddlers, babies, pregnant women, elderly men, elderly women, immune-compromised persons or children, etc.) and/or animals. The same applies regardless of when the sterilization is conducted. Also, if a product is already sufficiently safe to use so that it does not have to be sterilized, then the sterilization step can be avoided so long as it is determined reliably that the product is safe for its intended use either in humans or animals as the case may be or safe for its intended use in a sub-population of humans and/or animals. Regarding Fe Removal Several Options Are/May Be Relevant. In the case of Fe removal, it may be that the relevant (LE) or (SLE) does not contain any Fe and therefore there is no need to remove any Fe. It may be that the amount of Fe present is so low that it is not necessary to remove any Fe at all. It may be that the amount of Fe present is so high that the Fe removal procedure may have to repeated to achieve the relevant Fe-free or low-Fe content of the particular (LE) or (SLE) being processed depending on the use of the Fe-free (LE) or (SLE) or of the low-Fe (LE) or (SLE). Regarding Removal of Fe alone and/or Removal of Fe and Other Elements and/or Minerals from the (LE) or (SLE) Several Options Are/May Be Relevant. To some extent, removal of Fe may just be one option to exercise. It may be important to remove elements and/or minerals that may be detrimental to the intended use, functionality, safety and/or efficacy of the (LE) or (SLE) being processed. For example, the (LE) or (SLE) may contain contaminants other the Fe or contaminants in the presence of Fe or in the absence of Fe. For example, it may be desirable to remove those minerals and/or elements and/or metals from an (LE) or (SLE) that are undesirable for one reason or another. For example, it may be that the presence of lead (Pb), mercury (Hg), arsenic (As), or some other mineral at a particular concentration may be unsuitable for use in conjunction with its intended use in a human, an animal or some sub-group of persons and/or animals. For example, it may be detrimental to have more than a particular level of hard water or soft water elements or minerals in a particular (LE) or (SLE). It may be detrimental to have a particular level of mercury (Hg) or led (Pb) or some other element or mineral in the (LE) or (SLE). In such case, it may be desirable to precipitate out or remove as many of the minerals or elements from the (LE) or (SLE). To remove any particular element or mineral or a compound that may be present in a given (LE) or (SLE) sample, appropriate processes may be instituted that provide an (LE) or (SLE) suitable for its intended use in a compositional embodiment, in a formulational embodiment, in an intermediate embodiment, etc. For example, it may be desirable to have an (LE) or (SLE) free of any one or more of the following elements down to or below the threshold limits defined by 0 (ppm)—threshold (ppm) as well as the variations of the same in TABLE 12 below:

TABLE 12

| Element | 0 (ppm)-threshold (ppm) range |
| --- | --- |
| Al | 0-23,900 |
| Sb | 0-44 |
| As | 0-6 |
| Ba | 0-1.6 |
| Be | 0-21.7 |
| Bi | 0-280 |
| B | 0-340 |
| Br | 0-5 |
| CA | 0-2,700 |
| C | 0-600 |
| Ce | 0-24 |
| Cs | 0-7 |
| Cl | 0-81 |

TABLE 12-continued

| Element | 0 (ppm)-threshold (ppm) range |
| --- | --- |
| Cr | 0-385 |
| Co | 0-75 |
| Cu | 0-13 |
| Dy | 0-51 |
| Er | 0-40 |
| F | 0-8 |
| Gd | 0-109 |
| Ga | 0-22 |
| Ge | 0-77 |
| Hf | 0-4 |
| Ho | 0-11 |
| In | 0-27 |
| Fe | 0-104,563 |
| La | 0-128 |
| Li | 0-9 |
| Lu | 0-6 |
| Mg | 0-9,400 |
| Mn | 0-520 |
| Nd | 0-280 |
| Ni | 0-104 |
| Os | 0-2 |
| P | 0-580 |
| K | 0-6 |
| Pr | 0-66 |
| Re | 0-11 |
| Rb | 0-630 |
| Ru | 0-8 |
| Sm | 0-78 |
| Sc | 0-24 |
| Se | 0-795 |
| Si | 0-310 |
| Ag | 0-5 |
| Na | 0-12 |
| Sr | 0-62 |
| S | 0-26,800 |
| Te | 0-2 |
| Tb | 0-9 |
| Tl | 0-17 |
| Th | 0-98 |
| Tm | 0-55 |
| Sn | 0-18 |
| Ti | 0-3 |
| V | 0-780 |
| Yb | 0-27 |
| Y | 0-260 |
| Zn | 0-1,850 |
| Zr | 0-5 |

(f) Step 6—Similar to box (205) of FIG. 2: Wait for the clear FN to separate from the metallic phosphate compounds. Here the soluble phosphate is expected to precipitate Fe out of the FN which may be either liquid extract (LE) or it may be a sterilized liquid extract (SLE) in addition to being fossilized nutrition (FN) if obtained from fossilized soil (FS). The (FN) may instead be simply be (N) meaning that it was an extract obtained not from fossilized soil (FS), but instead the extract was obtained from non-fossilized soil or just soil (S). If obtained from (S) the liquid extract would just be (LE)—prior to sterilization and would be a sterilized liquid extract (SLE) after sterilization irrespective of whether the (LE) was obtained from (FS) to yield (FN) or was obtained from (S) to yield (N).

(g) Step 7—Similar to box (210): Pour off the clear (FN) which is also denoted the (FNC) as the Fe has been removed to an acceptable level as noted in box (205) where the (FNC) is the supernatant and the precipitated Fe is settled or substantially settled to the bottom of the container if the precipitate is more dense than the relevant (LE) or (SLE).

(h) Step 8—Similar to box (215) where the amount of heat applied is just enough to dissolve 1 gram of disaccharide per 2 ml of water provide and sufficient to fully dissolve (or substantially dissolve) such disaccharide in the heated water: Heat distilled water to 180° F. or to a temperature (for a time) sufficient to dissolve all or substantially all of disaccharide (e.g., sucrose) to yield the disaccharide solution (DSS).

(i) Step 9—Similar to box (220) in conjunction with box (225) with the qualification that all or substantially all of the disaccharide should be or preferably should be sought to be dissolved in the water until the desired sweetness level (e.g., Brix is 65-75) of the (DSS) is obtained: Add a certain amount of sucrose and dissolve to appropriate level of sweetness. Typically the water added should be at a level of 2 ml of water for each gram of a disaccharide such as sucrose. If a different disaccharide (or other sweetener) is used that is even more sweet than sucrose, then greater or lesser amounts of water (than used with sucrose at a level of 2 ml water per 1 gm of sucrose) may be needed to arrive at a Brix sweetness value between 65-75. In case different disaccharide (or other sweetener) is used that is less sweet than sucrose, then lesser or greater amounts of water (than used with sucrose at a level of 2 ml water per 1 gm of sucrose) may be needed to arrive at a Brix sweetness value between 65-75.

(j) Step 10—Similar to box (230) once the desired Brix sweetness value is achieved (e.g., 65-75): When the desired level of sweetness is achieved, cool solution to room temperature. The method of cooling could vary. Note that while a Brix sweetness level of 65-75 is preferred, the Brix value could be varied to be higher or lower (e.g., Brix level could be 10-90, 15-85, 20-80, 25-75, 30-75, 35=75, 40-75, 45-75, 50-75, 55-75, 60-75, 65-75, 65-70, 70-75, 75-80, 85-90, or any value or sub-value within each specified range).

(k) Step 11—Similar to box (235) where the (FNC) of box (205) and/or box (210) (less the precipitated Fe) is added to the (DSS) solution of box (230) or to the (DSS) of Step 10 noted herein: Add an amount of (FNC). The end product could be affected by adding raw arabica, fibersol, mangosteen, acai berry, combinations thereof, and/or other beneficial carbohydrates or proven nutrients before and/or after this step, as well as during the next step. A combination of (FNC) and/or (FN) may be added to achieve the desired level of sweetness and/or nutritional value and/or combination of sweetness and nutritional value. Preferably all the ingredients in the final composition crystallized can be categorized as "natural" ingredients without the addition of artificial sweeteners and/or artificial ingredients so as to classify the end-product an "all natural" or "natural" nutrient, nutritional supplement, food, and/or sweetener.

(l) Step 12—similar to box (235) and/or box (240): Mix and crystallize using gentle heat, pressure, and time. Each factor may affect the result.

(m) Result: Various mono- and oligo-saccharides may be formed. Formation of mono- and oligo-saccharides including, but not limited to, one or more of Mannose, Xylose, Arabinose, Galactose, Fucose, Glucose, N-acetyl galactosamine, N-acetyl glucosamine, and N-acetyl neuraminic acid or a sub-combination thereof may occur. The final product may also contain certain amino acids, certain minerals or certain elements, certain poly-saccharides, certain anti-oxidants, certain oils, certain other sweeteners, certain other nutrients, and/or certain botanical products, etc.

EXAMPLE 4

Second Formulational Embodiment

According to one example, Formulation II may be made as noted below.

To the extent possible, the above-noted steps may or may not be the same as those recited in the above-noted First Formulational Embodiment reciting the above-noted Steps 1-12. In view of the same, consider the procedure described below pursuant to this Second Formulational Embodiment:

(a) Step 1: Take fossilized soil (FS) from the ground and put it in a barrel.
(b) Step 2: Take water from a nearby well and drip in soil to extract the (FN).
(c) Step 3: Redrip as necessary to complete the extraction: Result: 60 trace minerals; Monosaccharides; Amino acids, and antioxidants at a certain pH.
(d) Step 4: Heat the (FN) to 180° F. to sterilize.
(e) Step 5: In a lab, add an amount of a compound containing soluble phosphate to the (FN), precipitating the Iron (Fe) from the solution, as well as other elements.
(f) Step 6: Wait for the clear (FN) to separate from the metallic phosphate compounds.
(g) Step 7: Pour off the clear (FN).
(h) Step 8: Heat distilled water to 180° F.
(i) Step 9: Add a certain amount of sucrose and dissolve to appropriate level of sweetness.
(j) Step 10: When level of sweetness is achieved, cool solution to room temperature. The method of cooling could vary.
(k) Step 11: Add an amount of (FNC). The end product could be affected by adding raw arabica, fibersol, mangosteen, acai berry, and/or other beneficial carbohydrates or proven nutrients before and after this step, as well as during the next step.
(l) Step 12: Mix and crystallize using gentle heat, pressure, and time. Each factor may affect the result.
(m) Result: Various mono- and oligo-saccharides may be formed. Formation of mono- and oligo-saccharides including, but not limited to, one or more of Mannose, Xylose, Arabinose, Galactose, Fucose, Glucose, N-acetyl galactosamine, N-acetyl glucosamine, and N-acetyl neuraminic acid or a sub-combination thereof may occur. The final product may also contain certain amino acids, certain minerals or certain elements, certain poly-saccharides, certain anti-oxidants, certain oils, certain other sweeteners, certain other nutrients, and/or certain botanical products, etc.

All patents, patent applications, publications, and references cited herein are incorporated by reference in their entirety for all purposes.

Although a few embodiments have been shown and described, it would be appreciated by those skilled in the art that changes may be made to these embodiments without departing from the principles and spirit of the invention, or from the scope of which is defined in the claims and their equivalents.

What is claimed is:

1. An extract composition comprising sterile fossilized soil organic matter (SFSOM) extracted from fossilized soil wherein the (SFSOM) includes N-acetylglucosamine of Formula 1:

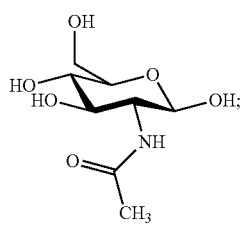

(Formula 1)

and mannose of Formula 3:

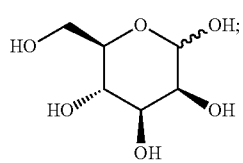

(Formula 3)

wherein the N-acetylglucosamine (NAG) is present at a concentration of from about 0.05 mg/1.0 gm to about 100 mg/1.0 gm, based on the total weight of the extract composition;

wherein the mannose (MANN) is present at a concentration of from about 0.05 mg/1.0 gm to about 100 mg/1.0 gm, based on the total weight of the extract composition;

wherein said (SFSOM) has a first sterile profile (i) of <100 cfu/gram aerobic plate count measured according to AOAC 990.12; and wherein components of the (SFSOM) including (NAG) and (MANN) are not isolated from the extract.

2. The extract composition of claim 1, wherein said (SFSOM) has a second sterile profile (ii) of <10 cfu/gram coliform count measured according to AOAC 991.14.

3. The extract composition of claim 2, wherein said (SFSOM) has a third sterile profile (iii) of <10 cfu/gram yeast measured according to FDA-BAM, 7th ed.

4. The extract composition of claim 2, wherein said (SFSOM) has a third sterile profile (iii-a) of <10 cfu/gram yeast measured according to FDA-BAM, 8th ed.

5. The extract composition of claim 3, wherein said (SFSOM) optionally has a fourth sterile profile (iv) of <10 cfu/gram mold measured according to FDA-BAM, 7th Edition.

6. The extract composition of claim 3, wherein said (SFSOM) has a fourth sterile profile (iv-a) of <10 cfu/gram mold measured according to FDA-BAM, 8th Edition.

7. The extract composition of claim 2, wherein said (SFSOM) optionally has a fourth sterile profile (iv-b) of ≦10 cfu/gram mold measured according to FDA-BAM, 7th Edition.

8. The extract composition of claim 2, wherein said (SFSOM) has a fourth sterile profile (iv-c) of ≦10 cfu/gram mold measured according to FDA-BAM, 8th Edition.

9. The extract composition of claim 1, further comprising one or more amino acids, or salts thereof, selected from the group consisting of: arginine, histidine, isoleucine, leucine, lysine, methionine, phenylalanine, serine, threonine, tryptophan, valine, alanine, aspartic acid, asparagine, cysteine, glutamic acid, glutamine, glycine, proline, and tyrosine.

10. The extract composition of claim 1 further comprising one or more of an element selected from the group consisting of, and at a corresponding concentration of about:

| Element | ppm |
|---------|-----|
| Al | 23,900 |
| Ga | 22 |
| Sm | 78 |
| Sb | 44 |
| Ge | 77 |
| Sc | 24 |
| As | 6 |
| Hf | 4 |
| Se | 795 |
| Ba | 1.6 |
| Ho | 11 |
| Si | 310 |
| Be | 21.7 |
| In | 27 |
| Ag | 5 |
| Bi | 280 |
| Fe | 104,563 |
| Na | 12 |
| B | 340 |
| La | 128 |
| Sr | 62 |
| Br | 5 |
| Li | 9 |
| S | 26,800 |
| Ca | 2,700 |
| Lu | 6 |
| Te | 2 |
| C | 600 |
| Mg | 9,400 |
| Tb | 9 |
| Ce | 24 |
| Mn | 520 |
| Tl | 17 |
| Cs | 7 |
| Nd | 280 |
| Th | 98 |
| Cl | 81 |
| Ni | 104 |
| Tm | 55 |
| Cr | 385 |
| Os | 2 |
| Sn | 18 |
| Co | 75 |
| P | 580 |
| Ti | 3 |
| Cu | 13 |
| K | 6 |
| V | 780 |
| Dy | 51 |
| Pr | 66 |
| Yb | 27 |
| Er | 40 |
| Re | 11 |
| Y | 260 |
| F | 8 |
| Rb | 630 |
| Zn | 1,850 |
| Gd | 109 |
| Ru | 8 |
| and Zr | 5. |

11. The extract composition of claim 1 further comprising one or more of an element selected from the group consisting of: Al, Sb, As, Ba, Be, Bi, B, Br, Ca, C, Ce, Cs, Cl, Cr, Co, Cu, Dy, Er, F, Gd, Ga, Ge, Hf, Ho, In, Fe, La, Li, Lu, Mg, Mn, Nd, Ni, Os, P, K, Pr, Re, Rb, Ru, Sm, Sc, Se, Si, Ag, Na, Sr, S, Te, Tb, Tl, Th, Tm, Sn, Ti, V, Yb, Y, Zn, and Zr.

12. The extract composition of claim 1 further comprising a member selected from the group consisting of a monosaccharide, an oligosaccharide, a disaccharide, an amino acid, humic acid, fulvic acid, humifulvic acid, a mineral and combinations thereof.

13. The extract composition of claim 12, wherein the composition has a glycemic index (GI) between about 35 and about 55.

14. The extract composition of claim 1 having a pH from about 1 to about 4.

15. The extract composition of claim 1 having a pH from about 1.7 to about 2.9.

16. A process for making sterile fossilized soil organic matter (SFSOM) extracted from fossilized soil wherein the (SFSOM) includes N-acetylglucosamine of Formula 1:

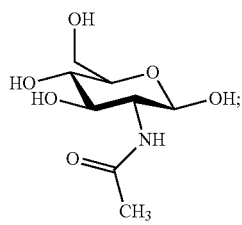

(Formula 1)

and mannose of Formula 3:

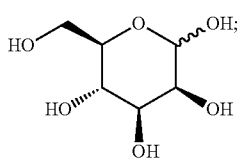

(Formula 3)

wherein the N-acetylglucosamine (NAG) is present at a concentration of from about 0.05 mg/1.0 gm to about 100 mg/1.0 gm, based on the total weight of the extract composition;

wherein the mannose (MANN) is present at a concentration of from about 0.05 mg/1.0 gm to about 100 mg/1.0 gm, based on the total weight of the extract composition; and wherein components of the (SFSOM) including (NAG) and (MANN) are not isolated from the extract;

said process comprising the steps of:
(a) extracting fossilized soil (FS) with an aqueous solvent to form a liquid extract including one or more of monosaccharides, amino acids, antioxidants, oligosaccharides, minerals or a combination thereof; and
(b) sterilizing the liquid extract such that said (SFSOM) has a first sterile profile (i) of <100 cfu/gram (SFSOM) of aerobic plate count measured according to AOAC 990.12.

17. The process of claim 16, wherein the (FS) is native to North America.

18. The process of claim 17 wherein the extracting step (a) comprises drip extraction with water; wherein the liquid extract has a pH from about 1 to about 4; wherein the minerals are selected from the group consisting of Al, Sb, As, Ba, Be, Bi, B, Br, Ca, C, Ce, Cs, Cl, Cr, Co, Cu, Dy, Er, F, Gd, Ga, Ge, Hf, Ho, In, Fe, La, Li, Lu, Mg, Mn, Nd, Ni, Os, P, K, Pr, Re, Rb, Ru, Sm, Sc, Se, Si, Ag, Na, Sr, S, Te, Tb, Tl, Th, Tm, Sn, Ti, V, Yb, Y, Zn, Zr and combinations thereof; and wherein the amino acids, or salts thereof, are selected from the group consisting of: arginine, histidine, isoleucine, leucine, lysine, methionine, phenylalanine, serine, threonine, tryptophan, valine, alanine, aspartic acid, asparagine, cysteine, glutamic acid, glutamine, glycine, proline, tyrosine, and combinations thereof.

19. The process of claim 16, wherein the sterilizing step (b) provides the (SFSOM) with a second sterile profile (ii) of <10 cfu/gram coliform count measured according to AOAC 991.14, and optionally a third sterile profile (iii) of <10 cfu/gram of yeast measured according to FDABAM, 7th Edition.

20. The process of claim 19, further comprising the steps of:
(c) adding an amount of soluble phosphate to a sterilized liquid extract having the first, second, and optionally third sterile profile sufficient to precipitate out iron from the sterilized liquid extract; and
(d) optionally separating out the precipitate from the sterilized liquid extract of step (c) to give a substantially clear sterilized liquid extract essentially free of dissolved Fe therein.

21. The process of claim 20, further comprising the steps of:
(e) adding a disaccharide to the sterilized liquid extract essentially free of dissolved Fe therein to yield a disaccharide solution;
(f) adding a source of xylose, glucose, or mixture thereof into the disaccharide solution;
(g) optionally mixing the disaccharide solution until the color of the disaccharide solution turns or is green; and
(h) optionally drying the disaccharide solution to give a green precipitate.

22. The process of claim 21, wherein the disaccharide comprises fructose and glucose optionally at a 50:50 (w/w) ratio.

23. The process of claim 21, wherein the source of xylose, glucose, or mixture thereof comprises raw arabica.

24. The process of claim 16, wherein said (SFSOM) exhibits an Oxygen Radical Absorbance Capacity (ORAC) rating of about 2,320 in micromole Trolox equivalent per liter units.

25. The process of claim 19, wherein the sterilizing step (b) provides the (SFSOM) with a third sterile profile (iii) of <10 cfu/gram of yeast measured according to FDA BAM, 7th ed., and optionally a fourth sterile profile (iv) of <10 cfu/gram of mold measured according to FDA-BAM, 7th Edition.

26. The process of claim 21, further comprising the steps of:
(i) adding an amount of a soluble phosphate to a sterilized liquid extract having the first, second, and optionally third sterile profile sufficient to precipitate out iron from the sterilized liquid extract; and
(j) optionally separating out the precipitate from the sterilized liquid extract (FNC) of step (c) to give a substantially clear sterilized liquid extract (FNC) essentially free of dissolved Fe therein; and
(k) optionally heating said (FNC) sufficient to have the first, second, and/or third sterile profile.

27. The process of claim 26, wherein said soluble phosphate is Potassium Phosphate Monobasic (PPM).

28. The process of claim 16, wherein the said sterilization step (b) further comprises heating the liquid extract to about 180° F., but not to exceed a temperature or a time that substantially destroys the constituent monosaccharides, minerals, amino acids, antioxidants or oligosaccharides in the extract.

29. The extract composition of claim 1, wherein the (SFSOM) contains no Fe or essentially no (Fe).

30. The process of claim 21, further comprising the step of:
(1) optionally adding fibersol, mangosteen, and/or acai berry to the disaccharide solution.

31. The process of claim 16, wherein one or more of raw arabica, fibersol, mangosteen, or acai berry is added to the liquid extract before or after said sterilization step(b).

* * * * *